United States Patent
Mao et al.

(10) Patent No.: US 10,011,570 B2
(45) Date of Patent: Jul. 3, 2018

(54) NUCLEIC ACID BINDING DYES WITH IMPROVED SAFETY

(71) Applicant: Biotium, Inc., Hayward, CA (US)

(72) Inventors: Fei Mao, Fremont, CA (US); Wai-Yee Leung, San Ramon, CA (US); Lori M. Roberts, Belmont, CA (US); Patrick Gordon McGarraugh, San Francisco, CA (US)

(73) Assignee: Biotium, Inc., Fremont, CA (US)

( * ) Notice: Subject to any disclaimer, the term of this patent is extended or adjusted under 35 U.S.C. 154(b) by 548 days.

(21) Appl. No.: 14/506,496

(22) Filed: Oct. 3, 2014

(65) Prior Publication Data

US 2015/0185182 A1    Jul. 2, 2015

Related U.S. Application Data

(60) Provisional application No. 61/886,612, filed on Oct. 3, 2013.

(51) Int. Cl.

| | |
|---|---|
| *C07D 221/12* | (2006.01) |
| *G01N 27/447* | (2006.01) |
| *C07D 417/06* | (2006.01) |
| *C09B 57/00* | (2006.01) |
| *C09B 15/00* | (2006.01) |
| *C09B 23/06* | (2006.01) |
| *C09B 23/04* | (2006.01) |

(52) U.S. Cl.
CPC ......... *C07D 221/12* (2013.01); *C07D 417/06* (2013.01); *C09B 15/00* (2013.01); *C09B 23/04* (2013.01); *C09B 23/06* (2013.01); *C09B 57/00* (2013.01); *G01N 27/44747* (2013.01)

(58) Field of Classification Search
CPC .................................................. C07D 221/12
USPC ................................ 546/10; 435/6.1; 544/2
See application file for complete search history.

(56) References Cited

U.S. PATENT DOCUMENTS

| | | | |
|---|---|---|---|
| 5,321,130 A | 6/1994 | Yue et al. | |
| 7,446,202 B2 | 11/2008 | Dallwig et al. | |
| 7,601,498 B2 | 10/2009 | Mao et al. | |
| 7,655,409 B2 | 2/2010 | Dallwig et al. | |
| 7,727,716 B2 | 6/2010 | Beaudet et al. | |
| 7,803,943 B2 * | 9/2010 | Mao | C09B 11/28 422/420 |
| 7,977,057 B2 | 7/2011 | Beaudet et al. | |

FOREIGN PATENT DOCUMENTS

CN        101531993 A  *  9/2009

OTHER PUBLICATIONS

Veselkov et al. (Journal of Chemical Physics, vol. 115, No. 5, 2001, pp. 2252-2266).*
Ames, et al. Methods for detecting carcinogens and mutagens with the *Salmonella*/mammalian-microsome mutagenicity test. Mutat Res. Dec. 1975;31(6):347-64.
Benson, et al. Heterodimeric DNA-binding dyes designed for energy transfer: stability and applications of the DNA complexes. Nucleic Acids Res. Dec. 11, 1993;21(24):5720-6.
Brooker, et al. Color and Constitution. V.1 The Absorption of Unsymmetrical Cyanines. Resonance as a Basis for a Classification of Dyes. J. Am. Chem. Soc. 1942; 64(2):199-210.
De Mesmaeker, et al. Backbone modifications for antisense oligonucleotides. Pure & Appl. Chem. 1997;69(3):437-440.
Deligeorgiev, et al. Intercalating cyanine dyes for nucleic acid detection. Recent Pat Mater Sci 2.1 (2009): 1-26.
Evenson, et al. 1H and 13C NMR assignments for the cyanine dyes SYBR Safe and thiazole orange. J Org Chem. Dec. 7, 2012;77(23):10967-71. doi: 10.1021/jo3021659. Epub Nov. 27, 2012.
Glazer, et al. Stable dye-DNA intercalation complexes as reagents for high-sensitivity fluorescence detection. Nature. Oct. 29, 1992;359(6398):859-61.
Markovits, et al. Ethidium dimer: a new reagent for the fluorimetric determination of nucleic acids. Markovits J, Rogues BP, Le Pecq JB.
Maron, et al. Revised methods for the *Salmonella* mutagenicity test. Mutat Res. May 1983;113(3-4):173-215.
McCann, et al. Detection of carcinogens as mutagens in the *Salmonella*/microsome test: assay of 300 chemicals. Proc Natl Acad Sci U S A. Dec. 1975;72(12):5135-5139.
National Toxicology Program (Aug. 15, 2005). Executive Summary Ethidium Bromide: Evidence for Possible Carcinogenic Activity.
Ohta, et al. Ethidium bromide and SYBR Green I enhance the genotoxicity of UV-irradiation and chemical mutagens in *E. coli*. Mutat Res. May 31, 2001;492(1-2):91-7.
SYBR Safe DNA Gel Stain White Paper. Life Technologies. 2003.
De Mesmaeker, et al. Backbone modifications for antisense oligonucleotides.Pure and Applied Chemistry. vol. 69, Issue 3, pp. 437-440.
Markovits, et al. Ethidium dimer: a new reagent for the fluorimetric determination of nucleic acids. Analytical Biochemistry. 1979; 94:259-264.
McCann, et al. Detection of carcinogens as mutagens in the *Salmonella*/microsome test: assay of 300 chemicals. Proc Natl Acad Sci U S A. Dec. 1975;72(12):5135-9.
National Toxicology Program (Aug. 15, 2005). Executive Summary Ethidium. Bromide: Evidence for Possible Carcinogenic Activity.

* cited by examiner

*Primary Examiner* — Jezia Riley
(74) *Attorney, Agent, or Firm* — Wilson Sonsini Goodrich & Roasti

(57) ABSTRACT

The invention provides compounds, including fluorescent nucleic acid dyes, and methods for use including nucleic acid detection. Further provided are kits, instruments and systems comprising compounds of the invention or adapted for use with compounds of the invention or other nucleic acid dyes.

23 Claims, 14 Drawing Sheets

Post nucleic acid gel staining with phenanthridium dyes

Post nucleic acid gel staining with Dye No. 9

Live cell staining

Glove permeability test

NUCLEIC ACID BINDING DYES WITH IMPROVED SAFETY

CROSS REFERENCE

This application claims the benefit of U.S. Provisional Application Ser. No. 61/886,612 filed on Oct. 3, 2013, which application is incorporated herein by reference in its entirety.

BACKGROUND OF THE INVENTION

Nucleic acids such as DNA and RNA are important biomolecules involved in genetic information storage and transmission from one generation to the next and in the routine functioning of all living organisms. As a result, nucleic acid detection is frequently conducted in life science research labs and has many practical applications, ranging from species identification to genetic disease screening, to pathogen detection and to forensic science, merely by way of example.

Among the different methods of nucleic acid detection, nucleic acid binding dyes are widely used because of the simplicity and high sensitivity offered (Deligeorgiev, et al. *Recent Patents on Materials Science* 2, 1-26(2009)). Nucleic acid binding dyes can be intrinsically nonfluorescent or only weakly fluorescent by themselves but may become highly fluorescent upon binding to nucleic acids, and thus may provide a high signal-to-noise ratio during detection. Binding of the dyes may take the mode of intercalation, where the dye may insert itself in between two adjacent nucleic acid base pair, or it may take the mode of minor groove binding, where the dye may reside in the minor groove of a double-stranded nucleic acid. Accordingly, the dyes may be termed as intercalators or minor groove binders, depending on the binding mode. Nucleic acid dyes may be extensively used in various practical applications. Some non-limiting examples may include nucleic acid detections, such as real-time qPCR for gene detection, visualization of cell nuclei, quantification of total nucleic acids in solutions, and staining of nucleic acids in gel matrix.

While nucleic acid dyes are highly useful, they may also pose serious safety issues for people who handle and dispose of them. Such issues may arise from the very DNA-binding nature of the dyes because the dyes' interaction with nucleic acids can interfere with the replication, transcription and translation of nucleic acids in cells (MacCnan, et al. *Proc Natl Acad Sci USA* 72(12), 5135(1975)). Moreover, nucleic acid dyes may greatly potentiate the DNA mutation caused by UV light or other known mutagens (Ohta et al. *Mutation Research* 492(1-2), 91(2001)). For these reasons, nucleic acid dyes can be potential mutagens and/or carcinogens. The safety issue is of special concern to nucleic acid gel staining because the amount of the dye solution used in the experiments may be large, for example, as much as 50 mL or higher, and because the experiments are routinely performed in many labs. One widely used gel stain is ethidium bromide, which is a known mutagen and highly suspected carcinogen (National Toxicology Program (Aug. 15, 2005). "Executive Summary Ethidium Bromide: Evidence for Possible Carcinogenic Activity"). Other dyes such as SYBR Safe, which have been alleged to be less mutagenic than ethidium bromide in Ames tests, may not represent an adequate solution because the increased cytotoxicity of SYBR Safe relative to ethidium bromide may make an assessment of SYBR Safe's mutagenicity at higher dye concentration difficult (SYBR Safe white paper, Life Technologies, 2003). Other approaches to improve safety have relied on the large physical size of the dyes without compromising the dyes' performance as gel stains. It is believed that the large molecular size may limit the cell membrane permeability of the dyes, thus reducing the chance for the dyes to interact with and hence cause damage to genomic DNA. Although such dyes may work very well in agarose-based nucleic acid gel staining, their large size may impede the dyes' diffusion into the more densely cross-linked polyacrylamide gels (PAGE gels) used for analyzing small nucleic acid fragments, and can result in relatively weak staining. Thus, there remains a need for safe and sensitive nucleic acid gel stains that overcome the drawbacks of the existing dyes.

SUMMARY OF THE INVENTION

In one aspect, the invention provides a nucleic acid binding dye for gel staining comprising a molecular weight less than 700 Da, exclusive of the mass of any counterion(s); an aromatic fluorescent core comprising one delocalized positive charge and no negative or localized charges; and at least one substituent covalently bound to the aromatic fluorescent core comprising an equal number of positive charges and negative charges in aqueous solution at pH 7; wherein the number of positive or negative charges is 1, 2, 3, 4, or 5.

In another aspect, the invention provides a nucleic acid binding dye characterized in that: a) it has a molecular weight of less than 700 Da, exclusive of the mass of any counterion(s); b) it lacks ability to penetrate the cellular membrane of a living eukaryotic cell as determined by fluorescent microscopy when the cell membrane is exposed to a concentration of 0.20 µM to 2.0 µM of the dye; c) remains soluble in distilled water at a concentration of up to 2.0 µM at about 25° C.; and d) tests negative for mutagenicity by the Ames test at a concentration no less than 2.0 µM. In some embodiments, the nucleic acid binding dye comprises at most one net positive charge (without considering any counter ions).

Also provided is a nucleic acid binding dye for staining nucleic acid embedded in a matrix comprising: a) nucleic acid binding dye having a molecular weight less than 700 Da, exclusive of the mass of any counterion(s); and b) a fluorescent core comprising at least one substituent; wherein the at least one substituent comprises a positive or negative charge; and wherein the overall charge of said one or more substituents is zero.

Further provided is a nucleic acid binding dye for gel staining with molecular weight less than 700 Da, exclusive of the mass of any counterion(s), wherein: i) the nucleic acid binding dye shows no cell permeability, as ascertained by fluorescence microscopy in a human cell at a concentration of 0.20 µM to 2.0 µM; ii) is fully water soluble at gel staining concentration; and iii) the nucleic acid binding dye does not show mutagenicity as determined in an Ames test at said concentration. In some embodiments, the nucleic acid binding dye comprises at most one net positive charge (without considering any counter ions).

Further provided, is a method of staining a nucleic acid embedded in a matrix or immobilized on a surface comprising: applying a fluorescent nucleic acid dye to said matrix or surface under conditions permitting formation of nucleic acid-dye complex, thereby staining a nucleic acid embedded in a gel wherein: i) the nucleic acid binding dye shows no cell permeability, as ascertained by fluorescence microscopy in a human cell at a concentration of 0.20 µM to 2.0 µM; and ii) complete water solubility at gel staining concentration; and iii) the nucleic acid binding dye does not show mutagenicity as determined in an Ames test at said concentration. In some embodiments, the nucleic acid binding dye comprises at most one net positive charge (without considering any counter ions).

Further provided, are compounds of Formula A1:

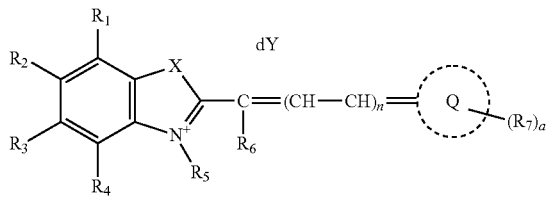

Formula A1 wherein:

$R_1$, $R_2$, $R_3$, $R_4$, and $R_6$ are independently selected from the group consisting of H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, or $C_1$-$C_6$ alkyl, when present, is optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$, —$NR_{29}(C=O)R_{30}$, —$NR_{31}S(=O)_2R_{32}$, or —$C(=O)NR_{33}R_{34}$;

each $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$ and $R_{35}$ is independently selected from the group consisting of H, $C_1$-$C_6$ alkyl, —$C(=O)R_{40}$, aryl, and heteroaryl; $R_{40}$ is $C_1$-$C_6$ alkyl;

X is O or S;

n is 0, 1 or 2;

Q is aryl or heteroaryl;

a is 0, 1, 2, 3 or 4;

$R_5$ is -L-$(Z)_m$ or $C_1$-$C_6$ alkyl, optionally substituted by at least one group independently selected from the group consisting of —$NR_{21}R_{22}$, —$NR_{21}R_{22}R_{35}$, —OH, halogen, aryl, and heteroaryl; or $R_5$ taken together with either $R_4$ or $R_6$ forms a 5- or 6-membered ring; each $R_7$ is independently -L-$(Z)_m$ or is independently selected from the group consisting of H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, or $C_1$-$C_6$ alkyl, when present, is optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$, —$NR_{29}(C=O)R_{30}$, —$NR_{31}S(=O)_2R_{32}$, or —$C(=O)NR_{33}R_{34}$;

Y is a water soluble counter ion; d is a number of Y groups sufficient to render the overall charge of the dye neutral; wherein at least one of $R_5$ or one of $R_7$ is -L-$(Z)_m$;

each L is independently a linker comprising 2-12 carbon atoms optionally comprising one or more N, O, or S atoms;

each Z is independently a group with a molecular weight of less than 450 and comprising one positive charge and one negative charge in neutral aqueous buffer.

In some embodiments of the compound of Formula A1: each $R_1$, $R_2$, $R_3$, and $R_4$ is independently selected from the group consisting of H, halo, aryl, heteroaryl, $C_1$-$C_3$ alkyl, $C_1$-$C_3$ alkoxy;

$R_6$ is H, $C_1$-$C_2$ alkyl, aryl, or heteroaryl;

each m is 1;

$R_5$ is -L-$(Z)_m$ or is $C_1$-$C_6$ alkyl optionally substituted by at least one group selected from the group consisting of an amino, alkylamino, dialkylamino, trialkylammonium, OH, halo, aryl, and heteroaryl; or $R_5$ taken together with either $R_4$ or $R_6$ forms a 5- or 6-membered ring;

each $R_7$ is independently -L-$(Z)_m$ or is independently selected from the group consisting of H, halo, aryl, heteroaryl, and $C_1$-$C_6$ alkyl, wherein said aryl, heteroaryl, $C_2$-$C_6$ alkenyl, or $C_1$-$C_6$ alkyl, when present, is optionally substituted with halo, aryl, heteroaryl, —$NR_{21}R_{22}$, $OR_{23}$, —$NR_{29}(C=O)R_{30}$, —$NR_{31}S(=O)_2R_{32}$, or —$C(=O)NR_{33}R_{34}$; and each $R_{21}$, $R_{22}$, $OR_{23}$, $R_{29}$, $R_{30}$, $R_{31}$, $R_{32}$, $R_{33}$, and $R_{34}$ is independently selected from the group consisting of H, $C_1$-$C_6$ alkyl, —$C(=O)R_{40}$, aryl, and heteroaryl; $R_{40}$ is $C_1$-$C_6$ alkyl.

In some embodiments of the compound of Formula A1, each Z is independently a group with a molecular weight less than 300 comprising one positive charge and one negative charge in neutral aqueous buffer.

In some embodiments of the compound of Formula A1, the positively charged group and negatively charged group are separated by 2, 3, 4, 5, or 6 chemical bonds.

In some embodiments of the compound of Formula A1, the positively charged group is selected from the group consisting of quaternized nitrogen, quaternized phosphorus, guanidine, amidine and substituted or unsubstituted amine group; and the negatively charged group is selected from the group consisting of carboxylate, carboxylic acid, sulfonate, sulfate, phosphonate, and phosphate.

In some embodiments of the compound of Formula A1, each Z is independently an amino acid.

In some embodiments of the compound of Formula A1, each Z comprises a single positively charged amine and a single negatively charged group selected from carboxylate and sulfonate.

In some embodiments of the compound of Formula A1, at least one -L$(Z)_m$ is Formula A21:

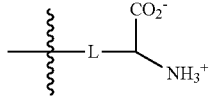

Formula A21

In some embodiments of the compound of Formula A21, at least one -L$(Z)_m$ is Formula A22:

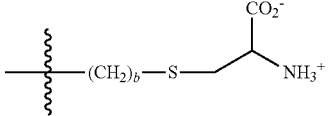

Formula A22 wherein each b is independently 2, 3, 4, 5, 6, 7 or 8.

In some embodiments of the compound of Formula A22, b is 3, 4, 5, or 6, for example b is 3.

In some embodiments of the compound of Formula A1 at least one -L$(Z)_m$ is Formula A23:

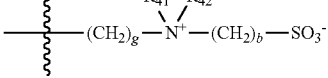

Formula A23 wherein each $R_{41}$ and $R_{42}$ is independently H or $C_1$-$C_8$ alkyl; and each g is independently 2, 3, 4, 5, 6, 7, or 8.

In some embodiments of the compound of Formula A1 at least one -L(Z)$_m$ is Formula A24:

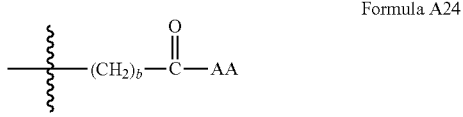

Formula A24 wherein AA is an amino acid; and
each b is independently 2, 3, 4, 5, 6, 7, or 8.

In some embodiments of the compound of Formula A24 at least one AA is selected from the group consisting of arginine, aspartic acid, glutamic acid, cysteine, threonine, tyrosine, lysine, and serine, wherein the amino acid is attached to the carbonyl group in Formula A24 in a manner such that the attached amino acid comprise a positively charge group and a negatively charged group.

In some embodiments of the compound of Formula A1 has the structure of Formula A3:

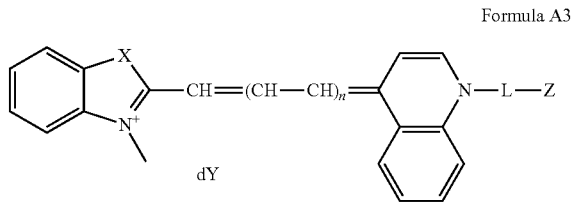

Formula A3 wherein X is O or S;
n is 0, 1 or 2;
Y is a water soluble counter ion; d is the number of Y groups sufficient to render the overall charge of the dye neutral;
L is a linker chain of 2-12 carbon atoms optionally comprising one or more N, O, or S atoms;
Z is a zwitterionic group with a molecular weight less than 450 comprising one positive charge and one negative charge in neutral aqueous buffer.

In some embodiments, a compound of the Formula A1 has the structure of Formula A4:

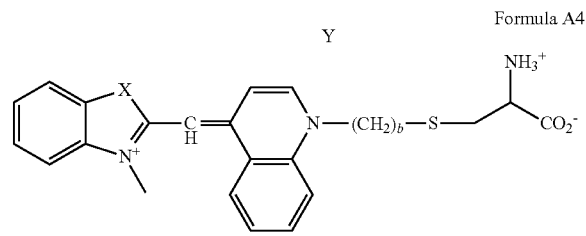

Formula A4 wherein X is O or S; b is an integer from 2 to 6 inclusive; Y is a water soluble anion.

In some embodiments, a compound of the Formula A1 is a compound in Table 1.

Further provided is a compound of Formula B1:

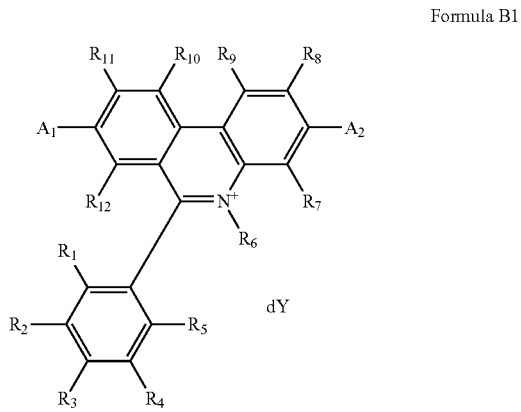

Formula B1 wherein:

$R_1$, $R_2$, $R_3$, $R_4$, and $R_5$ are each independently selected from the group consisting of H, halogen, —NR$_{21}$R$_{22}$ nitro (—NO$_2$), sulfonate (—SO$_3^-$), -L-(Z)$_m$, aryl, heteroaryl, $C_1$-$C_6$ alkyl, $C_1$-$C_6$ alkyl, wherein each aryl, heteroaryl, $C_1$-$C_6$ alkyl, when present, is optionally substituted with halo, aryl, heteroaryl, —NR$_{21}$R$_{22}$, OR$_{23}$, SR$_{24}$, —S(O)R$_{25}$, —S(O)$_2$R$_{26}$, —PR$_{27}$R$_{28}$;

each $R_{21}$, $R_{22}$, $R_{23}$, $R_{24}$, $R_{25}$, $R_{26}$, $R_{27}$, $R_{28}$, and $R_{29}$ is independently H, $C_1$-$C_3$ alkyl optionally substituted with halo or $C_1$-$C_3$ alkyl;

$R_6$ is $C_1$-$C_{12}$ alkyl, or is -L-(Z)$_m$;

each m is independently 0, 1, 2, or 3;

$R_7$, $R_8$, $R_9$, $R_{10}$, $R_{11}$ and $R_{12}$ are independently H, or a halogen substituent;

$A_1$ and $A_2$ are each independently —NR$_{21}$R$_{22}$;

Y is a water soluble counter ion; and d is a number of Y sufficient for balancing the charge of Formula B1;

each L is a linker chain of 2-12 carbon atoms optionally comprising one or more N, O or S atoms;

each Z is independently —NR$_{31}$R$_{32}$, —NR$_{33}$R$_{34}$R$_{35}$, or each Z is independently a group with a molecular weight of less than 450 and comprising one positive charge and one negative charge in neutral aqueous buffer; and each $R_{31}$, $R_{32}$, $R_{33}$, $R_{34}$, and $R_{35}$ is independently $C_1$-$C_7$ alkyl, aryl, heteroaryl wherein each aryl, heteroaryl, $C_1$-$C_7$ alkyl, when present is optionally substituted with halo, aryl, heteroaryl, —NR$_{21}$R$_{22}$, OR$_{23}$, SR$_{24}$, —S(O)R$_{25}$, —S(O)$_2$R$_{26}$, —PR$_{27}$R$_{28}$ and wherein (R$_{31}$ and R$_{32}$) or (R$_{34}$ and R$_{35}$) optionally connect to form a 3-, 4-, 5-, 6-, or 7-membered ring.

In some embodiments of the compound of Formula B1 at least one of $R_1$, $R_2$, $R_3$, $R_4$, and $R_5$ is sulfonate (—SO$_3^-$); $R_6$ is -L-(Z)$_m$; m is 1; Z is amine or quaternized nitrogen.

In some embodiments of the compound of Formula B1 at least one of $R_1$, $R_2$, $R_3$, $R_4$, $R_5$ and $R_6$ is -L-(Z)$_m$; Z is a group with a molecular weight less than 450 comprising one positive charge and one negative charge in neutral aqueous buffer.

In some embodiments the compound of Formula B1 has the structure of Formula B2:

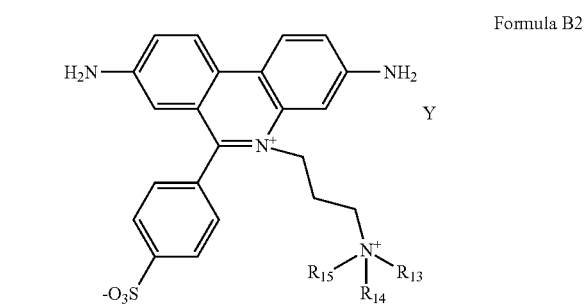

Formula B2 wherein $R_{13}$, $R_{14}$, and $R_{15}$ are each independently $C_1$-$C_4$ alkyl; and Y is an anion.

In some embodiments the compound of Formula B1 has the structure of Formula B3:

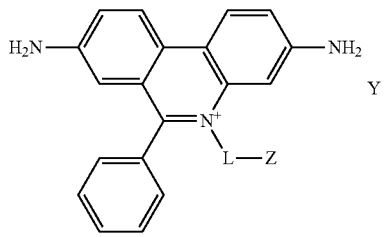

Formula B3 wherein:
L is a linker chain of 2-12 carbon atoms optionally comprising one or more N, O, or S atoms;
Z is a zwitterionic group with a molecular weight less than 450 comprising one positive charge and one negative charge in neutral aqueous buffer.

In some embodiments of the compound of Formula B3, -L-Z has the structure of Formula A21:

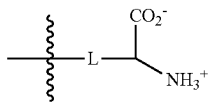

Formula A21

In some embodiments of the compound of Formula B3, -L-Z has the structure of Formula A22:

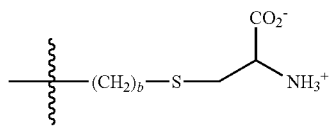

Formula A22 wherein b is 2, 3, 4, 5, 6, 7 or 8.

In some embodiments, a compound of the Formula B1 is a compound in Table 2.

Further provided is a compound of Formula C1:

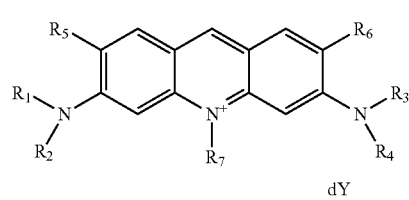

Formula C1 wherein:
$R_1$, $R_2$, $R_3$, $R_4$, are independently selected from H, aryl, heteroaryl, $C_2$-$C_6$ alkenyl, and $C_1$-$C_6$ alkyl, wherein said aryl, heteroaryl, $C_2$-$C_6$ alkenyl, and $C_1$-$C_6$ alkyl, when present, are optionally substituted with halo, aryl, or heteroaryl;
$R_5$ and $R_6$ are independently selected from H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, and $C_1$-$C_6$ alkyl, when present, are optionally substituted with halo, aryl, or heteroaryl;
$R_7$ is -L-$(Z)_m$;
m is 1, 2, 3, or 4;
Y is a water soluble counter ion; and d is the number of Y necessary for balancing the charge of Formula C1;
wherein, each L is a linker chain of 2-12 carbon atoms and which contains zero or more N or O or S atoms;
each Z is a group with a molecular weight less than 300 comprising one positive charge and one negative charge in neutral aqueous buffer.

In some embodiments of the compound of Formula C1, $R_1$, $R_2$, $R_3$, $R_4$, $R_5$ and $R_6$ are each independently selected from H and methyl.

In some embodiments of the compound of Formula C1, $R_1$, $R_2$, $R_3$, $R_4$, $R_5$ and $R_6$ are each independently selected from H and methyl and at least one -L-$(Z)_m$ is Formula A21:

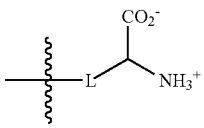

Formula A21

In some embodiments of the compound of Formula C1, $R_1$, $R_2$, $R_3$, $R_4$, $R_5$ and $R_6$ are each independently selected from H and methyl and at least one -L-$(Z)_m$ is Formula A22:

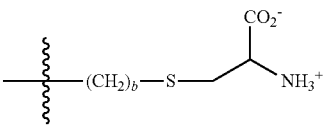

Formula A22 wherein each b is independently 2, 3, 4, 5, 6, 7 or 8.

In some embodiments of the compound of Formula C1, $R_1$, $R_2$, $R_3$ and $R_4$ are H; $R_5$ and $R_6$ are methyl, and -L-$(Z)_m$ is Formula A21.

In some embodiments of the compound of Formula C1, $R_1$, $R_2$, $R_3$ and $R_4$ are H; $R_5$ and $R_6$ are methyl, and -L-$(Z)_m$ is Formula A22.

In some embodiments of the compound of Formula C1, $R_1$, $R_2$, $R_3$ and $R_4$ are methyl; $R_5$ and $R_6$ are H, and -L-$(Z)_m$ is Formula A21.

In some embodiments of the compound of Formula C1, $R_1$, $R_2$, $R_3$ and $R_4$ are methyl; $R_5$ and $R_6$ are H, and -L-$(Z)_m$ is Formula A22.

In some embodiments, a compound of the Formula C1 is a compound in Table 3.

Also provided is a method of staining a nucleic acid embedded in a matrix or immobilized on a surface comprising the steps of: i) providing the nucleic acid sample; ii) providing a compound as described herein; iii) combining the sample and the compound; iv) incubating the combined sample and compound to form nucleic acid-dye complex for a time sufficient for the compound and nucleic acid to form a complex; v) illuminating the complex with a light and detecting the resulting fluorescence.

Further provided is a kit comprising: i) a compound as described herein; and ii) instructions instructing the use of the compound.

In some embodiments of the method, the nucleic acid binding dye is a compound of Formula A1, Formula B1, or Formula C1.

In some embodiments, the nucleic acid binding dye as described herein comprises at most one net positive charge (without considering any counter ions).

A method of staining a nucleic acid embedded in a matrix or immobilized on a surface comprising: applying a fluorescent nucleic acid dye as described herein to said matrix or surface under conditions permitting formation of nucleic acid-dye complex, thereby staining a nucleic acid embedded in a gel.

In some embodiments of the method, upon formation of said dye-nucleic acid complex yields visible bands indicative of size separation of individual fragments of nucleic acids from 10 base pairs to 150 base pairs.

Also provided is a complex of fluorescent nucleic acid dye as described herein and a nucleic acid.

Further provided is a precast agarose gel for the separation of nucleic acids comprising: from about 0.2% to about 4% agarose; the compound as described herein; and a buffer compatible with gel electrophoresis.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
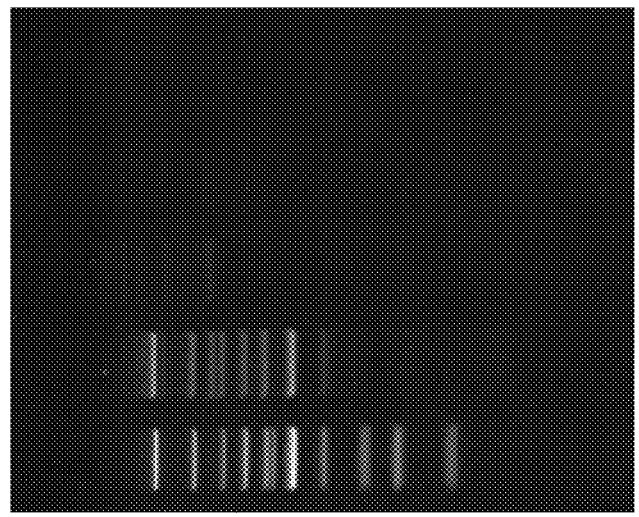
FIG. 1 shows the post nucleic acid gel staining with phenanthridium dyes of the invention. A): Two-fold dilutions of 1 kb DNA ladder (Biotium, 200 ng-25 ng) in 1% agarose gel stained with Dye No. 10 of Table 2 at 5 µM; B) Two-fold dilutions of low-molecular weight DNA ladder (NEB, 50-12.5 ng/lane) in 10% polyacrylamide gel stained with Dye No. 10 of Table 2 at 5 Exposure time for image capturing was 1.5 second.
Figure 1:
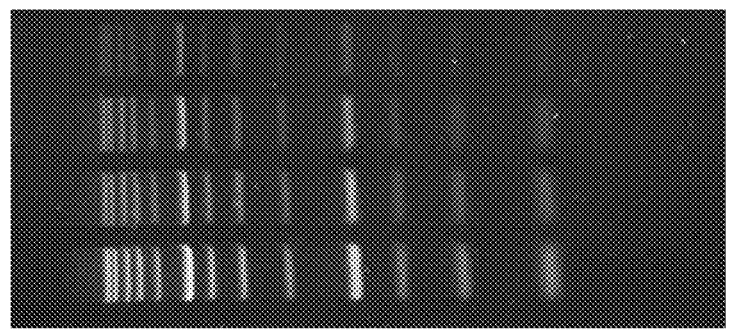
Figure 2:
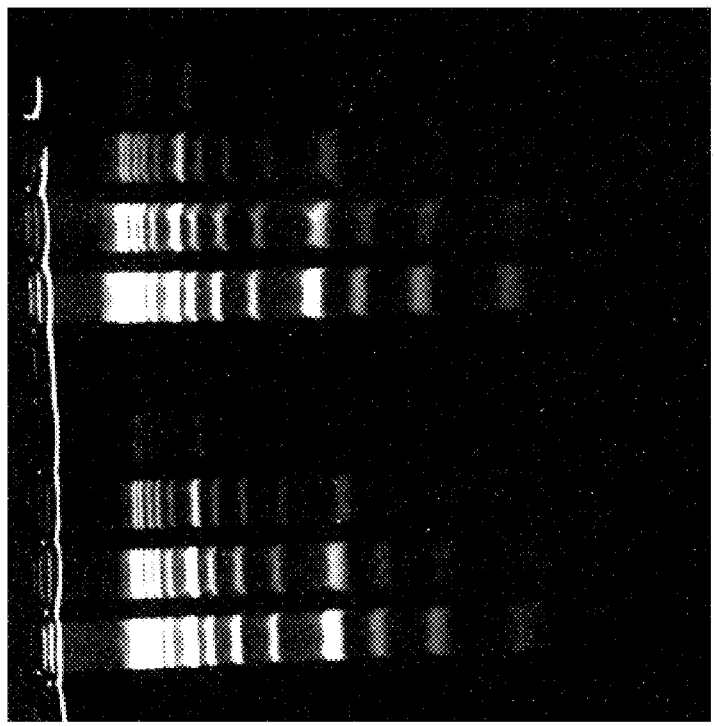
FIG. 2 shows the prestaining of agarose gels with propidium iodide (PI, left panel) and Dye No. 10 (right panel).
Figure 3:
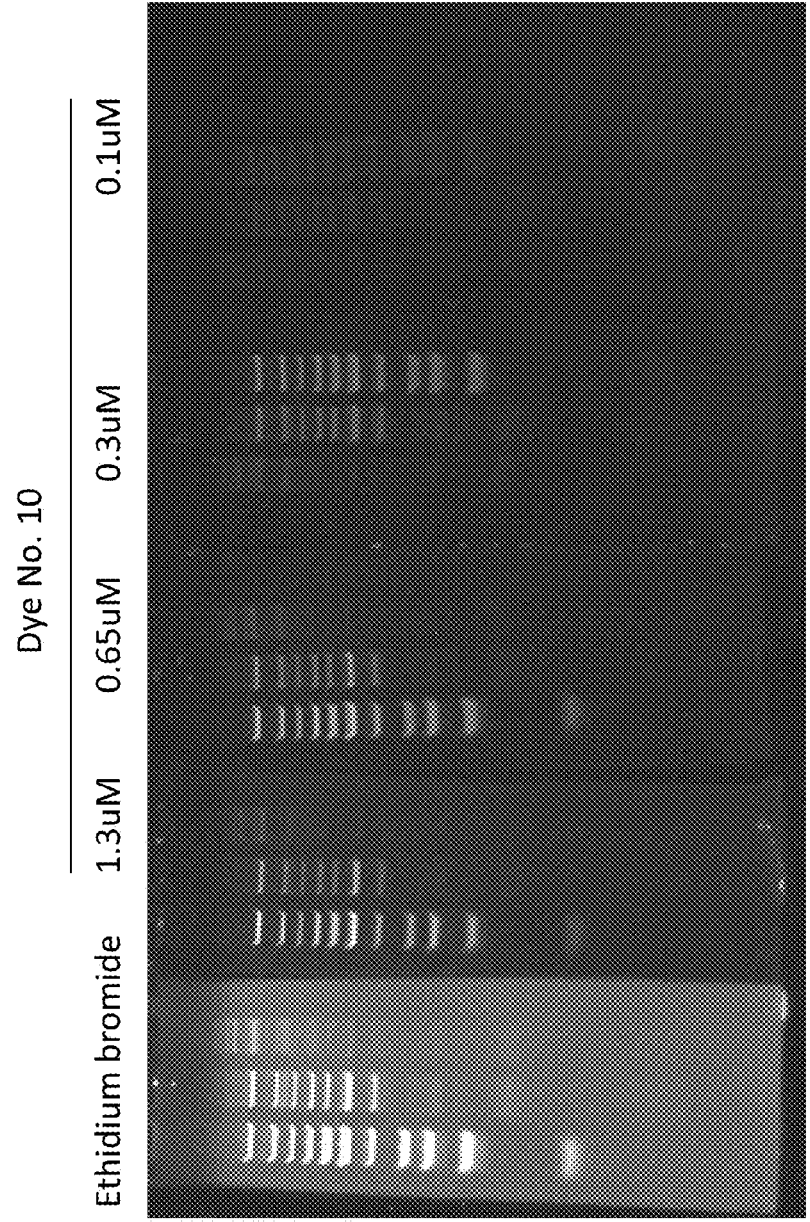
FIG. 3 shows the effect of dye concentration in post nucleic acid gel staining with Dye No. 10.
Figure 4:
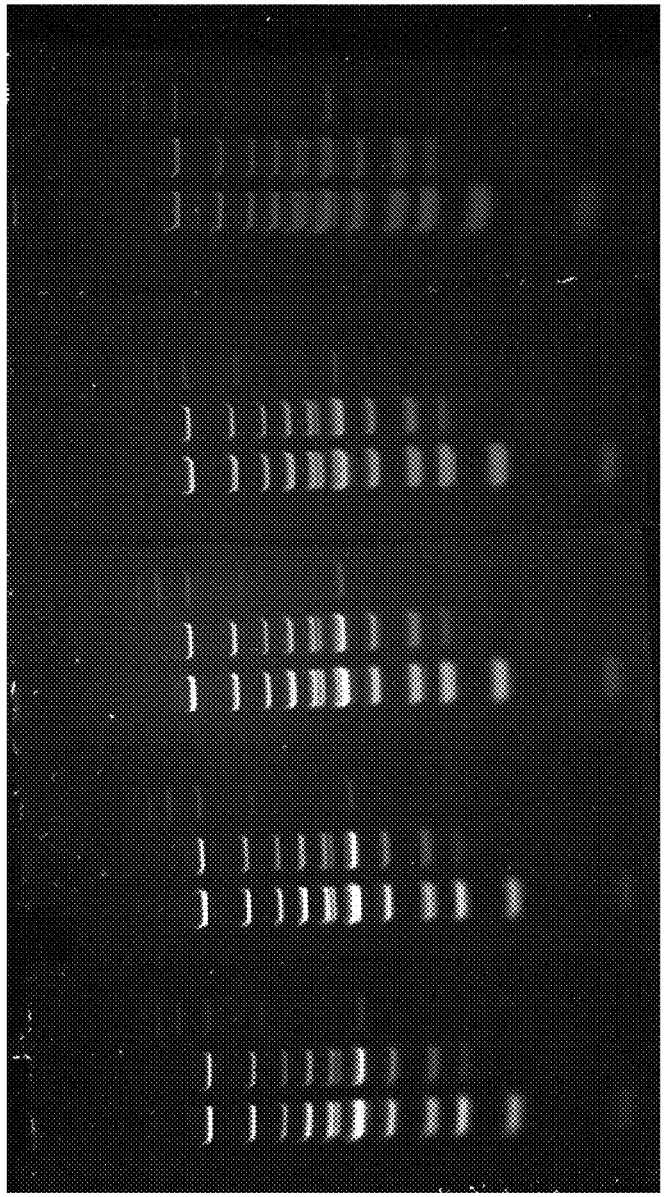
FIG. 4 shows the effect of dye concentration in post nucleic acid gel staining with Dye No. 4.

It will be understood that a word appearing herein in the singular encompasses its plural counterpart, and a word appearing herein in the plural encompasses its singular counterpart, unless implicitly or explicitly understood or stated otherwise. Further, it will be understood that for any given component described herein, any of the possible candidates or alternatives listed for that component, may generally be used individually or in any combination with one another, unless implicitly or explicitly understood or stated otherwise. Additionally, it will be understood that any list of such candidates or alternatives, is merely illustrative, not limiting, unless implicitly or explicitly understood or stated otherwise. Still further, it will be understood that any figure or number or amount presented herein is approximate, and that any numerical range includes the minimum number and the maximum number defining the range, whether the word "inclusive" or the like is employed or not, unless implicitly or explicitly understood or stated otherwise. Yet further, it will be understood that any heading employed is by way of convenience, not by way of limitation. Additionally, it will be understood that any permissive, open, or open-ended language encompasses any relatively permissive to restrictive language, less open to closed language, or less open-ended to closed-ended language, respectively, unless implicitly or explicitly understood or stated otherwise. Merely by way of example, the word "comprising" may encompass "comprising", "consisting essentially of", and/or "consisting of-type language.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

Various terms may be generally described, defined, and/or used herein to facilitate understanding. It will be understood that a corresponding general description, definition, and/or use of these various terms applies to corresponding linguistic or grammatical variations or forms of these various terms. It will also be understood that a general description, definition, and/or use, or a corresponding general description, definition, and/or use, of any term herein may not apply or may not fully apply when the term is used in a non-general or more specific manner. It will also be understood that the terminology used herein, and/or the descriptions and/or definitions thereof, for the description of particular embodiments, is not limiting. It will further be understood that embodiments described herein or applications described herein, are not limiting, as such may vary.

Definitions

As used herein, "alkyl" includes branched, straight-chain, and cyclic saturated aliphatic hydrocarbon groups. Alkyl groups specifically include methyl, ethyl, propyl, butyl, pentyl, hexyl, heptyl, octyl, nonyl, decyl, and so on, as well as cycloalkyls such as cyclopropyl, cyclobutyl, cyclopentyl, cyclohexyl, tetrahydronaphthalene, methylenecylohexyl, and so on. "Alkoxy" represents an alkyl group attached through an oxygen bridge. $C_2$ alkyl refers to an alkyl group with two total carbons. Similarly, $C_8$ alkyl refers to an alkyl group with eight total carbons.

The term "alkenyl" refers to a non-aromatic hydrocarbon group, straight, branched or cyclic, containing at least one carbon to carbon double bond. Alkenyl groups include, but are not limited to, ethenyl, propenyl, butenyl and cyclohexenyl. The straight, branched or cyclic portion of the alkenyl group may contain double bonds and may be substituted if a substituted alkenyl group is indicated. The attachment of an alkenyl group is generally via a $sp^2$ hybridized carbon.

As used herein, "aryl" refers to any stable monocyclic or polycyclic carbon ring of up to 7 atoms in each ring, wherein at least one ring is aromatic. Some non-limiting examples of aryl groups include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, tetrahydroquinoline, triazolyl, tetrazolyl, xanthenyl, and coumarinyl. In cases where the heteroaryl substituent is bicyclic and one ring is non-aromatic or contains no heteroatoms, it is understood that attachment is via the aromatic ring or via the heteroatom containing ring, respectively.

Alkyl, alkenyl, aryl or heteroaryl groups may optionally be substituted with at least one substituent selected from alkyl, alkenyl, halogen, —CN, —NO$_2$, —NR$_{81}$R$_{82}$, —OR$_{81}$, —NR$_{81}$S(=O)$_2$R$_{82}$, —C(=O)R$_{81}$, or —C(=O)NR$_{81}$R$_{82}$, wherein each of R$_{81}$ and R$_{82}$ is independently selected from H, alkyl, aryl or heteroaryl and when both R$_{81}$ and R$_{82}$ are present, they may in combination form a monocyclic or polycyclic, aromatic or heteroaromatic ring.

The terms "halo" or "halogen" are intended to include chloro, fluoro, bromo and iodo groups.

The term "aromatic" is used in its usual sense, including unsaturation that is essentially delocalized across multiple bonds, such as around a ring.

The term "substituent" refers to an atom, radical or chemical group which replaces a hydrogen in a substituted chemical group, radical, molecule, moiety or compound.

Unless otherwise stated, the term "radical", as applied to any molecule or compound, is used to refer to a part, fragment or group of the molecule or compound rather than to a "free radical". A radical may be linked to another moiety through a covalent bond.

The terms "polynucleotides", "nucleic acids", and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. "Polynucleotide" may also be used to refer to peptide nucleic acids (PNA), locked nucleic acids (LNA), threofuranosyl nucleic acids (TNA) and other unnatural nucleic acids or nucleic acid mimics. Other base and backbone modifications known in the art are encompassed in this definition. See, e.g. De Mesmaeker et al (1997) Pure & Appl. Chem., 69, 3, pp 437-440. Generally, the term "poly(amino acids)" may refer to polymers comprising natural or unnatural amino acid monomers covalently linked via peptide bonds. Poly(amino acids) may refer to proteins, peptides, and/or polypeptides, for example.

Generally, the term "immobilized" may be used in connection with a substance or substances, such as poly(amino acids), for example, that may be associated with a medium, such as a gel, a gel matrix, a surface, or a membrane, for example, such as any of same that may be associated with an electrophoretic process, for example. In general, while such a substance may be mobile during an electrophoretic process, such that it may move relative to the medium under the influence of a force or current, for example, it may be so mobile while still remaining associated with the medium. As such, in general, "immobilized" and associated terminology (such as immobilization, for example) may refer to the on-going association of a substance with a medium during and optionally following an electrophoretic process. Merely by way of example, an immobilized substance associated with a medium generally remains so associated during and optionally following an electrophoretic process, rather than entering into a solution associated with the electrophoretic process, for example, unless and until it becomes or is made to become disassociated with the medium, such as by intentional method or means, for example.

The term "PAGE", as used herein, comprises the technique of polyacrylamide gel electrophoresis and related methods of protein separation.

Generally, the terms "stain" and "dye" may be used interchangeably herein. These terms may refer to a molecule capable of absorbing light in the ultraviolet, visible, or infrared light spectra. In some embodiments, these terms refer to a molecule capable of absorbing light of a wavelength in a spectral range of wavelengths from about 200 nm to about 1,200 nm, inclusive, for example, such as from about 250 nm to about 1,200 nm, inclusive, for example. Generally, a difference between an excitation maximum and an emission maximum associated with a stain or a dye may be referred to as a Stokes shift.

Where a compound shown herein is a charged moiety, the compound may be associated with one or more counterions which balance the charge of the compound. When the compound is positively charged, a suitable counterion can be an anion, for instance a biologically compatible anion. Biologically compatible anions include, but are not limited to, halides (such as chloride, fluoride, iodide or bromide), sulfate, phosphate, acetate, trifluoroacetate, lactate, citrate, gluconate, or hydroxyethansulfate. When depicting a formula of a compound of the invention, the counterion may or may not be explicitly described for simplicity, even though it can be present as understood by a person skilled in the art.

A "mutagen" is a molecule or agent that can induce or increase the frequency of mutation in an organism and "mutagenicity" is the property of a molecule or agent that is mutagen. The mutagenicity of a molecule such as a dye can be measured with a variety of assays. Some assays to determine the cell permeability of a molecule or dye include, but are not limited to, the Ames test and mammalian cell genotoxicity tests, for example. A compound with mutagenicity can increase the rate of mutation in human cells. The rate of mutation in human cells can increase by 5%, 10%, 20% 50%, 100%, 1000% or more than 10000%. Exposure to a compound with mutagenicity can increase the rate of mutation of human DNA and can cause many health problems such as cancer for example.

A "complex" can be formed between a dye of the invention and a nucleic acid. The complex between the dye and the nucleic acid can be a molecular complex. A molecular complex can be an association between two or more molecules. The complex can form by the attractive bonding between the components of the complex—the dye and the nucleic acid. The complex can be an attractive interaction between the dye and the nucleic acid that results in a stable association in which the molecules are close to each other in space. The complex can be a loose association. The complex can be reversible. The complex can be the result of molecular bonding. The association can be the result of hydrogen bonding between the dye and the nucleic acid bases. The complex can be the result of covalent bonding. The complex can be weaker than a covalent bond. The complex can be the result of van der Waals attraction. The complex can be the result of the hydrophobic effect.

The property of a molecule to penetrate the cellular membrane of a cell is also called the cell permeability of the molecule. The cell permeability of a molecule can be measured with a variety of assays. Some assays to determine the cell permeability of a molecule or dye include, but are not limited to, direct measurements such as fluorescent microscopy, flow cytometry, or confocal microscopy and indirect methods such as PAMPA or Caco-2 permeability assay, for example. Flow cytometry and confocal microscopy can be forms of fluorescent microscopy. Confocal microscopy is an optical imaging technique that can be used to measure cell permeability of a molecule. Confocal microscopy can be used to reconstruct a three-dimensional structure of a cell that has been treated with fluorescent material. When cells are treated with both a molecule to be tested for permeability and a counterstain, the images can be compared to assess cell permeability of the molecule to be tested. To get an accurate assessment of cell permeability, the counterstain should not permeabilize the cell membrane or require a permeable cell membrane (such as methylene blue for example). The cells can be treated with a solution of the molecule to be measured at known concentration and the counterstain. The cells can then be imaged by scanning of the confocal microscopy instrument to measure the fluorescence of the molecule to be measured, and then again to measure the fluorescence of the counterstain. If the three-dimensional cellular structure defined by the counterstain contains the fluorescence from the molecule of interest, then the molecule can be deemed to have penetrated the cellular membrane of the cell or be deemed to have cellular permeability at the given concentration. Flow cytometry can be used to measure cell permeability of a molecule. In flow cytometry, light can be focused onto a stream of cells and can be fluorescence is measured. Flow cytometry can image a cell. Flow cytometry can scatter light of the internal components of cell. Measurement of fluorescence or in some cases light scatter can be used to determine if a molecule has permeated a cell or a population of cells.

Several indirect assays can be used to infer, estimate, or measure cell permeability of a molecule. Caco-2 can be used as an assay to determine the cell permeability of a molecule. The Caco-2 assay can be an indirect way to measure if a molecule has passed through a mono-layer of Caco-2 cells. PAMPA (parallel artificial membrane permeability assay) can be used as a non-cell based assay to predict the cell permeability of a molecule. The measurement from a PAMPA model can, in some cases, highly correlate with cell permeability.

The term "solubility" refers to the ability of a compound of the invention to be soluble in a solvent such as water. The solubility of a molecule in water can be influenced by several factors. The solubility of a molecule can be measured with a variety of assays. Some assays to determine the solubility of a molecule include, but are not limited to directly measuring the solubility, mixing the molecule in water and looking for undissolved molecule, measuring the concentration of the molecule and water and comparing the measurement to the calculated concentration, measuring the log P, or calculating the Flory-Huggins, Hildebrand, or Hansen solubility parameters. Several factors can influence the water solubility of a molecule. Some non-limiting examples of factors that can influence the solubility include for example, temperature of the water, pressure, salt concentration in the water, time of mixing between the water and the molecule. To be water soluble at a given concentration, pressure, and temperature can mean that after about 30 minutes of mixing the molecule in distilled water that contains no added salts or solutes, the concentration of the molecule dissolved in every aliquot of the water is equal or nearly equal to the expected concentration (calculated by moles of molecule added divided by amount of water) within the experimental error of the experiment.

Compounds of the Invention

Disclosed herein are novel nucleic acid binding dyes that may have the advantages of: 1) being nonmutagenic and noncytotoxic by being impermeable to cell membrane; 2) being physically small for penetration into dense PAGE gels; and 3) possessing binding affinity for sensitive nucleic acid detection and potentially offering dye removal to recover nucleic acid samples when desired.

In some embodiments, provided is a nucleic acid binding dye for gel staining comprising: a molecular weight less than 700 Da, exclusive of the mass of any counterion(s); an aromatic fluorescent core comprising one delocalized positive charge and no negative or localized charges; and at least one substituent covalently bound to the aromatic fluorescent core comprising J positive charges and K negative charges in aqueous solution at pH 7; wherein J is 1, 2, 3, 4, or 5; wherein K is 1, 2, 3, 4, or 5; and wherein J=K. In other embodiments, J and K are each 1, 2, or 3. In still other embodiments, J and K are 1 or 2. In other embodiments, J and K are 1. In some embodiments, the nucleic acid binding dye for the gel staining, exclusive of any counterion(s), has a molecular weight less than 1100, 1050, 1000, 950, 900, 850, 800, 750, 700, 650, 600, 575, 550, or 500 Da. In some embodiments, the dye, exclusive of any counterion(s), has a molecular weight from about 250 to about 800 Da. In some embodiments, the aromatic fluorescent core comprises a single positive charge delocalized around at least 1, 2, 3, or 4 aromatic rings inclusive. The aromatic fluorescent core can include, but are not limited to, cyanine, phenanthridium, or acridinium dye cores for example. Delocalization of charge can mean that the charge can be present on more than a single atom by resonance, tautomerization or through multiple bonds.

In some embodiments, provided is a nucleic acid binding dye characterized in that: a) it has a molecular weight of less than 700 Da, exclusive of the mass of any counterion(s); b) it lacks ability to penetrate the cellular membrane of a living eukaryotic cell as determined by fluorescent microscopy when the cell membrane is exposed to a concentration of 0.20 µM to 2.0 µM of the dye; c) remains soluble in an aqueous medium at a concentration of up to 2.0 µM at about 25° C.; d) tests negative for mutagenicity by the Ames test at a concentration no less than 2.0 µM. In some embodiments, the nucleic acid binding dye comprises at most one net positive charge (without considering any counter ions).

In some embodiments, provided is a nucleic acid binding dye embedded in a matrix comprising: a) nucleic acid binding dye having a molecular weight less than 700 Da, exclusive of the mass of any counterion(s); and b) a fluorescent core comprising at least one substituent; wherein the at least one substituent comprises a positive or negative charge; and wherein the overall charge of said one or more substituents is zero. The nucleic acid binding dye may be embedded in a matrix or immobilized on a surface, for example the nucleic acid may be embedded in a gel.

Also provided is a nucleic acid binding dye for gel staining having a molecular weight of less than 700 Da, exclusive of the mass of any counterion(s), wherein: i) the nucleic acid binding dye shows substantially no cell permeability, as ascertained by fluorescence microscopy in a human cell at a concentration of 0.20 µM to 2.0 µM; ii) is fully water soluble at gel staining concentration; and iii) the nucleic acid binding dye does not show mutagenicity as determined in an Ames test at said concentration. In some embodiments, the nucleic acid binding dye comprises at most one net positive charge (without considering any counter ions).

In some embodiments, dyes of the invention have the general structure of Formula A1, Formula B1, or Formula C1 below:

Formula A1

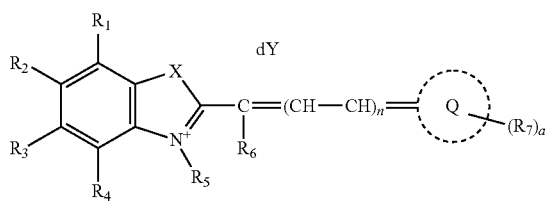

Formula B1

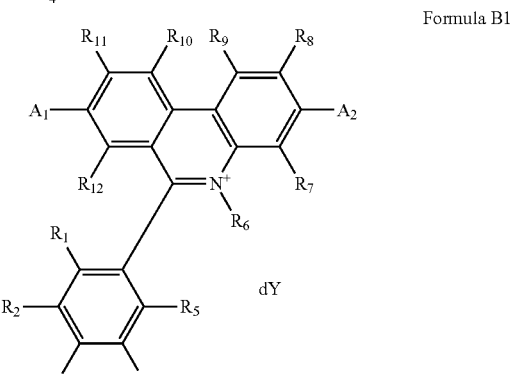

Formula C1

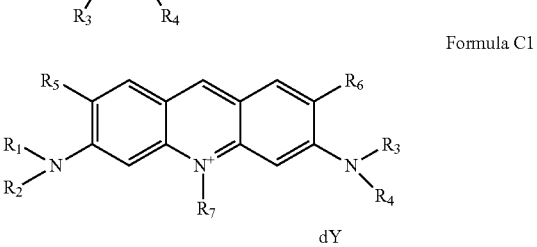

In some embodiments, the dye is an asymmetric cyanine dye having the general structure of Formula A1:

Formula A1

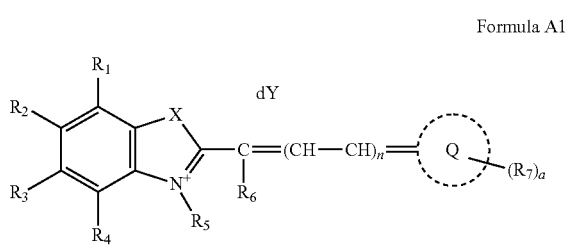

wherein:
$R_1$, $R_2$, $R_3$, $R_4$, and $R_6$ are independently selected from the group consisting of H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, or $C_1$-$C_6$ alkyl, when present, is optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$, —$NR_{29}(C=O)R_{30}$, —$NR_{31}S(=O)_2R_{32}$, or —$C(=O)NR_{33}R_{34}$;

each $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$ and $R_{35}$ is independently selected from the group consisting of H, $C_1$-$C_6$ alkyl, —C(=O)$R_{40}$, aryl, and heteroaryl; $R_{40}$ is $C_1$-$C_6$ alkyl;

X is O or S;

n is 0, 1 or 2;

Q is aryl or heteroaryl;

a is 0, 1, 2, 3 or 4;

$R_5$ is -L-(Z)$_m$ or $C_1$-$C_6$ alkyl, optionally substituted by at least one group independently selected from the group consisting of —NR$_{21}$R$_{22}$, —NR$_{21}$R$_{22}$R$_{35}$, —OH, halogen, aryl, and heteroaryl; or $R_5$ taken together with either $R_4$ or $R_6$ forms a 5- or 6-membered ring; each $R_7$ is independently -L-(Z)$_m$ or is independently selected from the group consisting of H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, or $C_1$-$C_6$ alkyl, when present, is optionally substituted with halo, aryl, heteroaryl, —NR$_{21}$R$_{22}$, OR$_{23}$, SR$_{24}$, —S(O)R$_{25}$, —S(O)$_2$R$_{26}$, —PR$_{27}$R$_{28}$, —NR$_{29}$(C=O)R$_{30}$, —NR$_{31}$S(=O)$_2$R$_{32}$, or —C(=O)NR$_{33}$R$_{34}$;

Y is a water soluble counter ion; d is a number of Y groups sufficient to render the overall charge of the dye neutral;

wherein at least one of $R_5$ or one of $R_7$ is -L-(Z)$_m$;

each L is independently a linker comprising 2-12 carbon atoms optionally comprising one or more N, O, or S atoms;

each Z is independently a group with a molecular weight of less than 450 Da and comprising one positive charge and one negative charge in neutral aqueous buffer.

In some embodiments, the dye is an asymmetric cyanine dye having the general structure of Formula A1 wherein:

each $R_1$, $R_2$, $R_3$, and $R_4$ is independently selected from the group consisting of H, halo, aryl, heteroaryl, $C_1$-$C_3$ alkyl, $C_1$-$C_3$ alkoxy;

$R_6$ is H, $C_1$-$C_2$ alkyl, aryl, or heteroaryl;

each m is 1;

$R_5$ is -L-Z or is $C_1$-$C_6$ alkyl optionally substituted by at least one group selected from the group consisting of an amino, alkylamino, dialkylamino, trialkylammonium, OH, halo, aryl, and heteroaryl; or $R_5$ taken together with either $R_4$ or $R_6$ forms a 5- or 6-membered ring;

each $R_7$ is independently -L-(Z)$_m$ or is independently selected from the group consisting of H, halo, aryl, heteroaryl, and $C_1$-$C_6$ alkyl optionally substituted with halo, aryl, heteroaryl, —NR$_{21}$R$_{22}$, OR$_{23}$, —NR$_{29}$(C=O)R$_{30}$, —NR$_{31}$S(=O)$_2$R$_{32}$, or —C(=O)NR$_{33}$R$_{34}$;

each $R_{21}$, $R_{22}$, OR$_{23}$, $R_{29}$, $R_{30}$, $R_{31}$, $R_{32}$, $R_{33}$, and $R_{34}$ is independently selected from the group consisting of H, $C_1$-$C_6$ alkyl, —C(=O)R$_{40}$, aryl, and heteroaryl; $R_{40}$ is $C_1$-$C_6$ alkyl.

In some embodiments wherein the dye has the structure of Formula A1, $R_1$, $R_2$, $R_3$, and $R_4$ is independently selected from the group consisting of $C_1$-$C_3$ alkyl, $C_1$-$C_3$ alkoxy, halogen atoms, aryl and heteroaryl; $R_6$ is selected from the group consisting of H, $C_1$-$C_2$ alkyl, aryl and heteroaryl; X is O or S; n is 0, 1 or 2; Q is an aryl or heteroaryl; a is 0, 1, 2, 3 or 4; $R_5$ is a $C_1$-$C_6$ alkyl optionally substituted by at least one group selected from the group consisting of an amino, alkylamino, dialkylamino, trialkylammonium, hydroxy, halogen atoms aryl and heteroaryl, or $R_5$ covalently connects with either $R_4$ or $R_6$ to form a 5- or 6-membered ring, or R5 is a -L-(Z)$_m$; each $R_7$ is independently selected from the group consisting of H, halogen atoms, aryl, heteroaryl, amino, alkyl amino, dialkyl amino, alkyoxy and alkyl, wherein the alkyl or alkyl portion of the alkyl amino, dialkyl amino and alkyoxy is optionally substituted, or $R_7$ is a -L-(Z)$_m$; Y is a water soluble counter ion; and d is the number of Y necessary for balancing the charge of Formula A1; and either $R_5$ or at least one $R_7$ must be a -L-(Z)$_m$.

In some embodiments wherein the dye of the invention has the structure of Formula A1, $R_1$ is selected from the group consisting of H, halo, azido, nitro, cyano, aryl, heteroaryl, $C_2$-$C_6$ alkenyl, and $C_1$-$C_6$ alkyl optionally substituted with halo, aryl, heteroaryl, —NR$_{21}$R$_{22}$, OR$_{23}$, SR$_{24}$, —S(O)R$_{25}$, —S(O)$_2$R$_{26}$, —PR$_{27}$R$_{28}$, —NR$_{29}$(C=O)R$_{30}$, —NR$_{31}$S(=O)$_2$R$_{32}$, or —C(=O)NR$_{33}$R$_{34}$. In some embodiments, $R_1$ is selected from the group consisting of H, halo, azido, nitro, cyano, aryl, heteroaryl, $C_2$-$C_6$ alkenyl, and $C_1$-$C_6$ alkyl. In some embodiments, $R_1$ is selected from the group consisting of H, halo, aryl, heteroaryl, $C_1$-$C_3$ alkyl, and $C_1$-$C_3$ alkoxy. In other embodiments, $R_1$ is selected from the group consisting of H, halo, $C_1$-$C_3$ alkyl. In still other embodiments, $R_1$ is H or halo. In some embodiments, $R_1$ is H.

In some embodiments wherein the dye of the invention has the structure of Formula A1, $R_2$ is selected from the group consisting of H, halo, azido, nitro, cyano, aryl, heteroaryl, $C_2$-$C_6$ alkenyl, and $C_1$-$C_6$ alkyl optionally substituted with halo, aryl, heteroaryl, —NR$_{21}$R$_{22}$, OR$_{23}$, SR$_{24}$, —S(O)R$_{25}$, —S(O)$_2$R$_{26}$, —PR$_{27}$R$_{28}$, —NR$_{29}$(C=O)R$_{30}$, —NR$_{31}$S(=O)$_2$R$_{32}$, or —C(=O)NR$_{33}$R$_{34}$. In some embodiments, $R_2$ is selected from the group consisting of H, halo, azido, nitro, cyano, aryl, heteroaryl, $C_2$-$C_6$ alkenyl, and $C_1$-$C_6$ alkyl. In some embodiments, $R_2$ is selected from the group consisting of H, halo, aryl, heteroaryl, $C_1$-$C_3$ alkyl, and $C_1$-$C_3$ alkoxy. In other embodiments, $R_2$ is selected from the group consisting of H, halo, $C_1$-$C_3$ alkyl. In still other embodiments, $R_2$ is H or halo. In some embodiments, $R_2$ is H.

In some embodiments wherein the dye of the invention has the structure of Formula A1, $R_3$ is selected from the group consisting of H, halo, azido, nitro, cyano, aryl, heteroaryl, $C_2$-$C_6$ alkenyl, and $C_1$-$C_6$ alkyl optionally substituted with halo, aryl, heteroaryl, —NR$_{21}$R$_{22}$, OR$_{23}$, SR$_{24}$, —S(O)R$_{25}$, —S(O)$_2$R$_{26}$, —PR$_{27}$R$_{28}$, —NR$_{29}$(C=O)R$_{30}$, —NR$_{31}$S(=O)$_2$R$_{32}$, or —C(=O)NR$_{33}$R$_{34}$. In some embodiments, $R_3$ is selected from the group consisting of H, halo, aryl, heteroaryl, $C_1$-$C_3$ alkyl, and $C_1$-$C_3$ alkoxy. In other embodiments, $R_3$ is selected from the group consisting of H, halo, $C_1$-$C_3$ alkyl. In still other embodiments, $R_3$ is H or halo. In some embodiments, $R_3$ is H.

In some embodiments wherein the dye of the invention has the structure of Formula A1, $R_4$ is selected from the group consisting of H, halo, azido, nitro, cyano, aryl, heteroaryl, $C_2$-$C_6$ alkenyl, and $C_1$-$C_6$ alkyl optionally substituted with halo, aryl, heteroaryl, —NR$_{21}$R$_{22}$, OR$_{23}$, SR$_{24}$, —S(O)R$_{25}$, —S(O)$_2$R$_{26}$, —PR$_{27}$R$_{28}$, —NR$_{29}$(C=O)R$_{30}$, —NR$_{31}$S(=O)$_2$R$_{32}$, or —C(=O)NR$_{33}$R$_{34}$. In some embodiments, $R_4$ is selected from the group consisting of H, halo, aryl, heteroaryl, $C_1$-$C_3$ alkyl, and $C_1$-$C_3$ alkoxy. In other embodiments, $R_4$ is selected from the group consisting of H, halo, $C_1$-$C_3$ alkyl. In still other embodiments, $R_4$ is H or halo. In some embodiments, $R_4$ is H.

In some embodiments wherein the dye of the invention has the structure of Formula A1, $R_6$ is selected from the group consisting of H, halo, azido, nitro, cyano, aryl, heteroaryl, $C_2$-$C_6$ alkenyl, and $C_1$-$C_6$ alkyl optionally substituted with halo, aryl, heteroaryl, —NR$_{21}$R$_{22}$, OR$_{23}$, SR$_{24}$, —S(O)R$_{25}$, —S(O)$_2$R$_{26}$, —PR$_{27}$R$_{28}$, —NR$_{29}$(C=O)R$_{30}$, —NR$_{31}$S(=O)$_2$R$_{32}$, or —C(=O)NR$_{33}$R$_{34}$. In some embodiments, $R_6$ is selected from the group consisting of H, halo, aryl, heteroaryl, $C_1$-$C_3$ alkyl, and $C_1$-$C_3$ alkoxy. In other embodiments, $R_6$ is selected from the group consisting of H, halo, $C_1$-$C_3$ alkyl. In still other embodiments, $R_6$ is H or halo. In some embodiments, $R_6$ is H.

In some embodiments wherein the dye of the invention has the structure of Formula A1, $R_1$, $R_2$, $R_3$, $R_4$, and $R_6$ are each independently selected from the group consisting of of H, halo, azido, nitro, cyano, aryl, heteroaryl, $C_2$-$C_6$ alkenyl, and $C_1$-$C_6$ alkyl optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$, —$NR_{29}(C=O)R_{30}$, —$NR_{31}S(=O)_2R_{32}$, or —$C(=O)NR_{33}R_{34}$. In some embodiments, $R_1$, $R_2$, $R_3$, $R_4$, and $R_6$ are each independently selected from the group consisting of H, halo, aryl, heteroaryl, $C_1$-$C_3$ alkyl, and $C_1$-$C_3$ alkoxy. In other embodiments, $R_1$, $R_2$, $R_3$, $R_4$, and $R_6$ are each independently selected from the group consisting of H, halo, and $C_1$-$C_3$ alkyl. In still other embodiments, $R_1$, $R_2$, $R_3$, $R_4$, and $R_6$ are each H.

In some embodiments wherein the dye of the invention has the structure of Formula A1 Formula B1 or Formula C1, each $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$ and $R_{35}$ is independently selected from the group consisting of H, $C_1$-$C_6$ alkyl, —$C(=O)R_{40}$, aryl, and heteroaryl. In other embodiments, each $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$ and $R_{35}$ is independently selected from the group consisting of H, $C_1$-$C_6$ alkyl, aryl, and heteroaryl. In still other embodiments, each $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$ and $R_{35}$ is independently H or $C_1$-$C_6$ alkyl.

In some embodiments wherein the dye of the invention has the structure of Formula A1, $R_{40}$, when present, is $C_1$-$C_6$ alkyl optionally substituted with —$NR_{21}R_{22}$, $OR_{23}$, $SR_{24}$, —$S(O)R_{25}$, —$S(O)_2R_{26}$, —$PR_{27}R_{28}$, —$NR_{29}(C=O)R_{30}$, —$NR_{31}S(=O)_2R_{32}$, or —$C(=O)NR_{33}R_{34}$; wherein each $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$ and $R_{35}$ is independently selected from the group consisting of H, $C_1$-$C_6$ alkyl, aryl, and heteroaryl. In other embodiments, $R_{40}$ is $C_1$-$C_6$ alkyl.

In some embodiments wherein the dye of the invention has the structure of Formula A1, X is O or S. In other embodiments, X is O. In still other embodiments, X is S.

In some embodiments wherein the dye of the invention has the structure of Formula A1, n is 0, 1 or 2. In other embodiments, n is 0 or 1. In other embodiments, n is 0. In still other embodiments, n is 1. In some embodiments, n is 2.

In some embodiments, Q is aryl or heteroaryl. In other embodiments, Q is aryl. In still other embodiments, Q is heteroaryl. In some embodiments, Q is a quinoline group. For example, the quinoline group can be

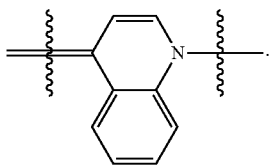 [SMILES: *N1C=CC(=*)c2ccccc21]

In some embodiments, -Q-$(R_7)_a$

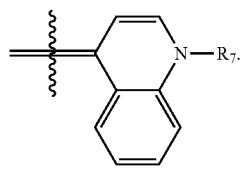

In some embodiments, a is 0, 1, 2, 3 or 4. In some embodiments, a is 0, 1, or 2. In other embodiments, a is 0 or 1. In still other embodiments, a is 1. In some embodiments, a is 0.

In some embodiments, $R_5$ is -L-$(Z)_m$ or is $C_1$-$C_6$ alkyl, optionally substituted by at least one group independently selected from the group consisting of —$NR_{21}R_{22}$, —$NR_{21}R_{22}R_{35}$, —OH, halogen, aryl, and heteroaryl; or $R_5$ taken together with either $R_4$ or $R_6$ forms a 5- or 6-membered ring. In some embodiments, R5 is -L-$(Z)_m$ or is $C_1$-$C_6$ alkyl, optionally substituted by at least one group independently selected from the group consisting of —$NR_{21}R_{22}$, —$NR_{21}R_{22}R_{35}$, —OH, halogen, aryl, and heteroaryl. In other embodiments, $R_5$ taken together with either $R_4$ or $R_6$ forms a 5- or 6-membered ring. In still other embodiments, $R_5$ is -L-$(Z)_m$. In some embodiments, $R_5$ is $C_1$-$C_6$ alkyl, optionally substituted by at least one group independently selected from the group consisting of —$NR_{21}R_{22}$, —$NR_{21}R_{22}R_{35}$, —OH, halogen, aryl, and heteroaryl. In other embodiments, $R_5$ is $C_1$-$C_3$ alkyl. $R_5$ can be methyl. In other embodiments, R5 is Formula A21, Formula A22, Formula A23, or Formula A24. In some embodiments, $R_5$ is Formula A21.

In some embodiments, each $R_7$ is independently -L-$(Z)_m$ or is independently selected from the group consisting of H, halo, azido, nitro, cyano, aryl, heteroaryl, $C_2$-$C_6$ alkenyl, and $C_1$-$C_6$ alkyl optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$, —$NR_{29}(C=O)R_{30}$, —$NR_{31}S(=O)_2R_{32}$, or —$C(=O)NR_{33}R_{34}$. In other embodiments, each $R_7$ is -L-$(Z)_m$. In some embodiments, each $R_7$ is or is independently selected from the group consisting of H, halo, azido, nitro, cyano, aryl, heteroaryl, $C_2$-$C_6$ alkenyl, and $C_1$-$C_6$ alkyl optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$, —$NR_{29}(C=O)R_{30}$, —$NR_{31}S(=O)_2R_{32}$, or —$C(=O)NR_{33}R_{34}$. In other embodiments, each $R_7$ is independently selected from the group consisting of H, halo, azido, nitro, cyano, aryl, heteroaryl, $C_2$-$C_6$ alkenyl, and $C_1$-$C_6$ alkyl. In some embodiments, each $R_7$ is independently selected from the group consisting of H, halo, azido, nitro, cyano, aryl, heteroaryl, $C_2$-$C_6$ alkenyl, and $C_1$-$C_6$ alkyl. In other embodiments, each $R_7$ is independently selected from the group consisting of H, halo, azido, nitro, cyano. In still other embodiments, each $R_7$ is independently selected from the group consisting of H, halo, aryl, heteroaryl, $C_1$-$C_3$ alkyl, and $C_1$-$C_3$ alkoxy. $R_7$ can be H. In some embodiments, at least $R_5$ or one of $R_7$ is -L-$(Z)_m$. In some embodiments, $R_5$ is -L-$(Z)_m$, and each $R_7$ is H. In other embodiments, $R_7$ is -L-$(Z)_m$ and $R_5$ is methyl.

In some embodiments wherein the dye of the invention has the structure of Formula A1 Formula B1 or Formula C1, Y is a water soluble counter ion. Y can be counter ion that allows the ionic complex to dissolve in water at a concentration of about 2 µM. In some embodiments, Y can be any counter ion. Some examples of Y include, but are not limited to, $F^-$, $Br^-$, $Cl^-$, $I^-$, $ClO_4^-$, $PF_6^-$, $BF_4^-$, $SO_4^{2-}$, $HSO_4^-$, $H_2PO_4^-$, $HPO_4^{2-}$, acetate, lactate, gluconate, citrate and trifluoroacetate, for example. In some embodiments, each Y is a selected from the group consisting of $F^-$, $Cl^-$, $Br^-$, $I^-$, and $ClO_4^-$. In other embodiments, Y is $I^-$.

In some embodiments wherein the dye of the invention has the structure of Formula A1 Formula B1 or Formula C1, d is the number of Y groups sufficient to render the overall charge of the dye neutral. In some embodiments, d is 1. In other embodiments, d is 2. In some embodiments dY is selected from the group consisting of $F^-$, $Cl^-$, $Br^-$, $I^-$, $ClO_4^-$, $PF_6^-$, $BF_4^-$, $HSO_4^-$ and $H_2PO_4^-$.

In some embodiments wherein the dye of the invention has the structure of Formula A1, Formula B1, or Formula C1, each m is independently 1, 2, 3, or 4. In other embodiments, each m is independently 1 or 2. In some embodiments, each m is 1.

In some embodiments wherein the dye of the invention has the structure of Formula A1, Formula B1, or Formula C1, L is a linker chain of 2-12 carbon atoms optionally comprising one or more N, O, or S atoms. In other embodiments, L is a $C_2$-$C_{12}$ alkyl optionally comprising one or more heteroatoms selected from N, O, or S. L may be a substantially neutral linker comprising 2-12 nonhydrogen atoms. As used herein, the term "substantially neutral" refers to a group which has substantially no charge in relevant conditions. For example, in a pH 7 aqueous solution at least about 90% of a dye of formula 1A may have an uncharged L group. This can require that L does not comprise any significantly acidic or basic groups or quarternized ammonium groups, such as carboxylic acid (carboxylate) group, phosphoric acid (phosphate) group, sulfuric acid (sulfonate) group, amine groups and ammonium group for example. In some embodiments, L is a completely neutral linker.

In some embodiments wherein the dye of the invention has the structure of Formula A1, Formula B1, or Formula C1, each Z is independently a group with a molecular weight less than 450 Da comprising one positive charge and one negative charge in neutral aqueous buffer. Z can be a zwitterionic moiety, which is generally a chemical moiety comprising a single positively charged group and a single negatively charged group. In some embodiments, Z can comprise a positively charged group and negatively charged group that are separated by 2 to 6 chemical bonds. In some embodiments, Z comprises two positive charges and two negative charges. In some embodiments, Z comprises a positive and a negative charge that are each independently either a formal charge on a single atom or a formal charge dispersed over more than one atom. A formal charge can be dispersed over more than one atom through resonance or a formal charge can be dispersed over a group of atoms through tautomerism, for example.

In some embodiments wherein the dye of the invention has the structure of Formula A1, Formula B1, or Formula C1, each Z is independently a group with a molecular weight less than about 450, 400, 350, 300, 275, 250, 225, 200, 150, or 70 Da comprising one positive charge and one negative charge in neutral aqueous buffer. In some embodiments wherein the dye of the invention has the structure of Formula A1, Formula B1, or Formula C1, each Z is independently a group with a molecular weight less than about 800, 750, 700, 650, 600, 550, 500, 450, 400, 350, 300, 275, 250, 225, 200, 150, or 70 Da comprising one positive charge and one negative charge in neutral aqueous buffer. In some embodiments, Z has a molecular weight less than 600. In some embodiments, Z has a molecular weight less than 450. In some embodiments, Z has a molecular weight less than 300.

In some embodiments wherein the dye of the invention has the structure of Formula A1, Formula B1, or Formula C1, the positively charged group and negatively charged group are separated by 2, 3, 4, 5, or 6 chemical bonds. In some embodiments, the positively charged and negatively charged groups are separated by less than 7 bonds. In some embodiments, the positively and negatively charged groups may be close together in 3D space. In other embodiments, the positively and negatively charged groups are uncharged in solid form and become charged in an aqueous solution at a range of about pH 4 to about pH 9 and more commonly around pH 7, for example.

In some embodiments wherein the dye of the invention has the structure of Formula A1, Formula B1, or Formula C1, the positively charged group may be any group selected from the group consisting of quarternized nitrogen, quarternized phosphorus, guanidine, amidine and substituted or unsubstituted amine group. Guanidine, amidine and substituted or unsubstituted amine groups are generally basic and can be protonated to give rise to a positive charge within physiological pH range, which are generally from about pH 4 to about pH 9 and more commonly around pH 7, for example. When charged or protonated, they are generally referred to as guanidinium, amidinium and ammonium, respectively. In general, the protonated and unprotonated forms of these groups can be in rapid equilibrium. For the purpose of the present invention, the protonated and unprotonated forms of these groups are equivalent and their corresponding terms will be used interchangeably.

In some embodiments wherein the dye of the invention has the structure of Formula A1, Formula B1, or Formula C1, the negatively charged group may be any group selected from the group consisting of carboxylate, sulfonate, sulfate, phosphonate, and phosphate. Similarly, these negatively charged groups may be protonated within physiological pH range to become electrically neutral, where again the two forms of the chemical group are in rapid equilibrium. Thus, the protonated and unprotonated forms of these groups are considered equal as well for the purpose of the invention.

In some embodiments, Z comprises a single positively charged group selected from amines (substituted or unsubstituted) and a single negatively charged group selected from carboxylate and sulfonate.

In some embodiments, each Z can independently comprise an amino acid. The amino acid can be a natural amino acid. The set of natural amino acids includes A, R, N, D, C, E, Q, G, H, I, L, K, M, F, P, S, T, W, Y, V, U, and O. In some embodiments, each Z can independently be arginine, histidine, spartic acid, glutamic acid, cysteine, threonine, asparagine, glutamine, tyrosine, lysine, or serine. In some embodiments, each Z can independently comprise an unnatural amino acid, for instance any $C_1$-$C_{12}$ alkyl group comprising a carboxylic acid and a basic nitrogen. Some non-limiting examples include p-azidophenylalanine, pyrrolysine, alpha-methylnorvaline, ornithine, beta-alanine, gamma aminobutyric acid, aminoisobutyric acid for example. In some embodiments, each Z can independently comprise an unnatural or a natural amino acid.

In some embodiments wherein the dye of the invention has the structure of Formula A1, Formula B1, or Formula C1, at least one -L(Z)$_m$ has the structure of Formula A21:

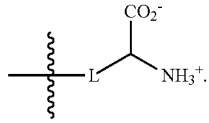

Formula A21

In other embodiments, at least one -L(Z)$_m$ has the structure of Formula A21; wherein L is a neutral linker comprising 1 to 12 carbon atoms optionally comprising one or more N, O, or S atoms.

In some embodiments wherein the dye of the invention has the structure of Formula A1, Formula B1, or Formula C1, at least one -L(Z)$_m$ has the structure of Formula A22:

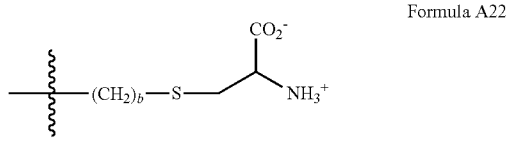

Formula A22 and each b is independently 2, 3, 4, 5, 6, 7 or 8. In some embodiments, each b is independently 3, 4, 5, or 6. In some embodiments, b is 3.

In some embodiments wherein the dye of the invention has the structure of Formula A1, Formula B1, or Formula C1, at least one -L(Z)$_m$ has the structure of Formula A23:

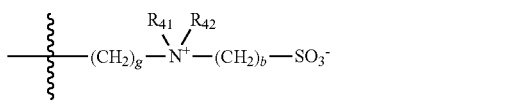

Formula A23 and each $R_{41}$ and $R_{42}$ is independently H or $C_1$-$C_8$ alkyl, and each g is independently 2, 3, 4, 5, 6, 7, or 8.

In some embodiments wherein the dye of the invention has the structure of Formula A1, Formula B1, or Formula C1, at least one -L(Z)$_m$ has the structure of Formula A24:

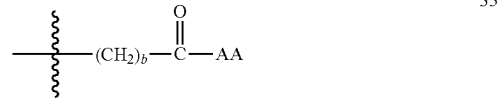

Formula A24 and AA is an amino acid; and each b is independently 2, 3, 4, 5, 6, 7, or 8. In some embodiments, b is 3, 4, 5, or 6. In some embodiments, b is 3. In some embodiments, at least one AA is selected from the group consisting of arginine, aspartic acid, glutamic acid, cysteine, threonine, tyrosine, lysine, and serine, wherein the amino acid is attached to the carbonyl group in Formula A24 in a manner such that the attached amino acid comprise a positively charge group and a negatively charged group.

In some embodiments wherein the dye of the invention has the structure of Formula A1, Formula B1, or Formula C1, each -L(Z)$_m$ is selected from a group consisting of Formula A21, Formula A22, Formula A23, and Formula A24.

In some embodiments, the asymmetric cyanine dye has the structure of Formula A2:

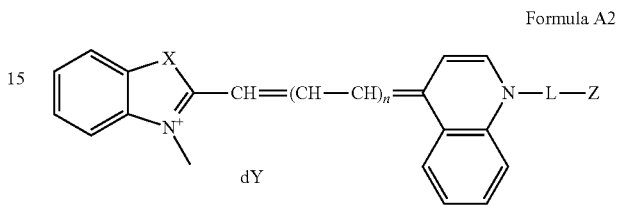

Formula A2 wherein X is O or S; n is 0, 1 or 2; d and Y are as defined herein; -L-Z is -L-(Z)$_m$ wherein m is 1; and L and Z are as defined herein. In some embodiments, -L-Z has the structure of Formula A21 above. In other embodiments, -L-Z has the structure of Formula A22.

In another embodiment, the asymmetric cyanine dye has the following structure:

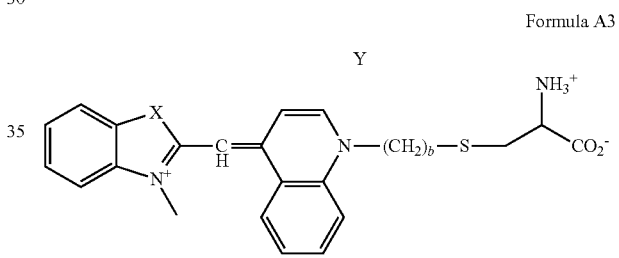

Formula A3 wherein X is O or S; b is selected from the group consisting of 2, 3, 4, 5, and 6; and Y is a water soluble monovalent anion. In some embodiments, X is S and b is 3.

Some non-limiting examples of dyes according to Formula A1, A2 and A3 are listed in Table 1:

TABLE 1

Asymmetric cyanine dyes

| Dye No. | structure |
|---|---|
| 1 | 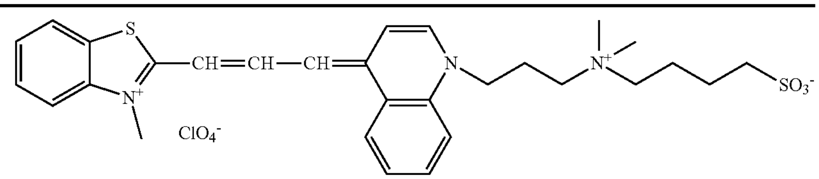 |
| 2 | 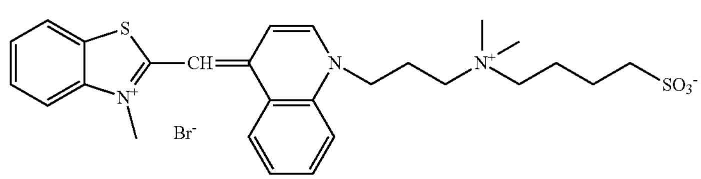 |

TABLE 1-continued
Asymmetric cyanine dyes
| Dye No. | structure |
|---|---|
| 3 | 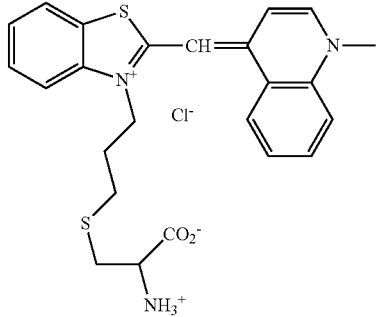 |
| 4 | 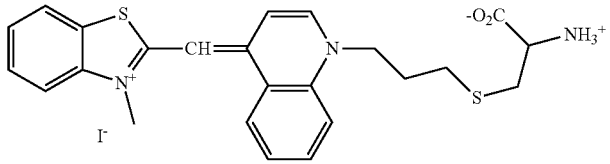 |
| 5 | 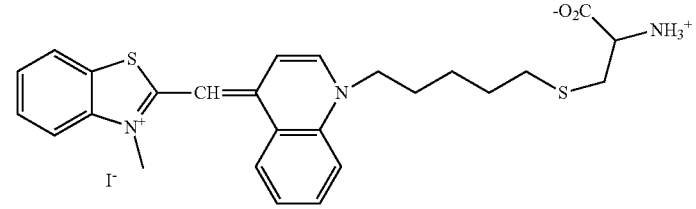 |
| 6 | 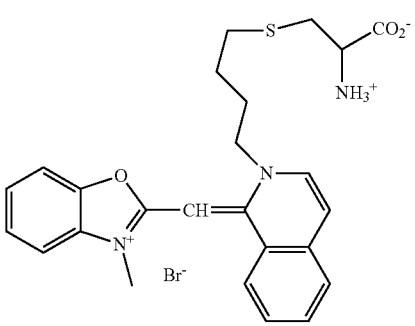 |
| 7 | 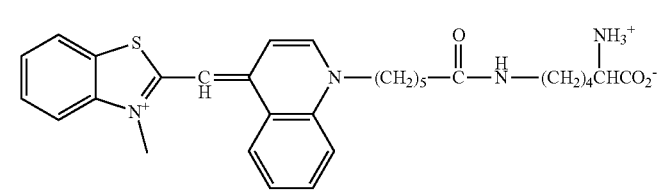 |

TABLE 1-continued

Asymmetric cyanine dyes

| Dye No. | structure |
|---|---|
| 8 | 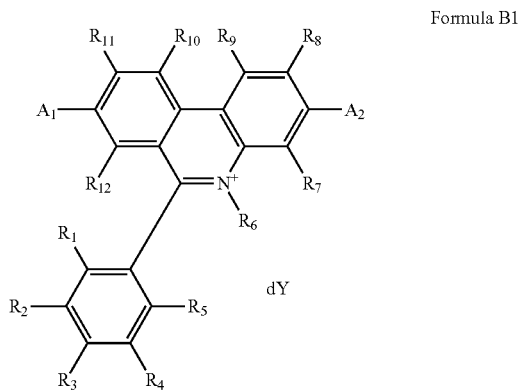 |

Further provided is a phenanthridium dye having the structure of Formula B1:

Formula B1 wherein:

$R_1$, $R_2$, $R_3$, $R_4$, and $R_5$ are each independently selected from the group consisting of H, halogen, $-NR_{21}R_{22}$, nitro ($-NO_2$), sulfonate ($-SO_3^-$), $-L-(Z)_m$, aryl, heteroaryl, $C_1$-$C_6$ alkyl, $C_1$-$C_6$ alkyl, wherein each aryl, heteroaryl, $C_1$-$C_6$ alkyl, $C_1$-$C_6$ alkyl, when present, is optionally substituted with halo, aryl, heteroaryl, $-NR_{21}R_{22}$, $OR_{23}$, $SR_{24}$, $-S(O)R_{25}$, $-S(O)_2R_{26}$, $-PR_{27}R_{28}$;

each $R_{21}$, $R_{22}$, $R_{23}$, $R_{24}$, $R_{25}$, $R_{26}$, $R_{27}$, $R_{28}$, and $R_{29}$ is independently H, $C_1$-$C_3$ alkyl optionally branched or optionally substituted with halo or $C_1$-$C_3$ alkyl;

$R_6$ is $C_1$-$C_{12}$ alkyl, or is -L-$(Z)_m$;

m is 0, 1, 2, or 3;

$R_7$, $R_8$, $R_9$, $R_{10}$, $R_{11}$ and $R_{12}$ are independently H, or a halogen substituent;

$A_1$ and $A_2$ are each independently $-NR_{21}R_{22}$;

Y is a water soluble counter ion; and d is a number of Y sufficient for balancing the charge of Formula B1;

each L is a linker chain of 2-12 carbon atoms optionally comprising one or more N, O or S atoms;

each Z is independently $-NR_{31}R_{32}$, $-N^+R_{33}R_{34}R_{35}$, or each Z is independently a group with a molecular weight of less than 450 and comprising one positive charge and one negative charge in neutral aqueous buffer; and each $R_{31}$, $R_{32}$, $R_{33}$, $R_{34}$, and $R_{35}$ is independently $C_1$-$C_7$ alkyl, aryl, heteroaryl wherein each aryl, heteroaryl, $C_1$-$C_7$ alkyl, when present is optionally substituted with halo, aryl, heteroaryl, $-NR_{21}R_{22}$, $OR_{23}$, $SR_{24}$, $-S(O)R_{25}$, $-S(O)_2R_{26}$, $-PR_{27}R_{28}$ and wherein ($R_{31}$ and $R_{32}$) or ($R_{34}$ and $R_{35}$) optionally connect to form a 3-, 4-, 5-, 6-, or 7-membered ring.

In some embodiments wherein the dye of the invention has the structure of Formula B1, $R_1$ is selected from the group consisting of H, halogen, azido, cyano, $-NR_{21}R_{22}$, nitro ($-NO_2$), sulfonate ($-SO_3^-$), -L-$(Z)_m$, aryl, heteroaryl, $C_1$-$C_6$ alkyl, wherein each aryl, heteroaryl, $C_1$-$C_6$ alkyl, when present, is optionally substituted with halo, aryl, heteroaryl, $-NR_{21}R_{22}$, $OR_{23}$, $SR_{24}$, $-S(O)R_{25}$, $-S(O)_2R_{26}$, $-PR_{27}R_{28}$. In other embodiments, $R_1$ is selected from the group consisting of H, halogen, azido, cyano, $-NR_{21}R_{22}$, nitro ($-NO_2$), sulfonate ($-SO_3^-$), -L-$(Z)_m$, aryl, heteroaryl, $C_1$-$C_6$ alkyl. In still other embodiments, $R_1$ is selected from the group consisting of H, halogen, nitro ($-NO_2$), sulfonate ($-SO_3^-$), -L-$(Z)_m$, aryl, heteroaryl, $C_1$-$C_6$ alkyl. In some embodiments, $R_1$ is selected from the group consisting of H, halogen, azido, cyano, nitro ($-NO_2$), sulfonate ($-SO_3^-$), and $C_1$-$C_6$ alkyl. In some embodiments, $R_1$ is H. In other embodiments, $R_1$ is -L-$(Z)_m$.

In some embodiments wherein the dye of the invention has the structure of Formula B1, $R_1$ is selected from the group consisting of H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, or $C_1$-$C_6$ alkyl, when present, is optionally substituted with halo, aryl, heteroaryl, $-NR_{21}R_{22}$, $OR_{23}$, $SR_{24}$, $-S(O)R_{25}$, $-S(O)_2R_{26}$, $-PR_{27}R_{28}$, $-NR_{29}(C=O)R_{30}$, $-NR_{31}S(=O)_2R_{32}$, or $-C(=O)NR_{33}R_{34}$; wherein each $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$ and $R_{35}$ is independently selected from the group consisting of H, $C_1$-$C_6$ alkyl, $-C(=O)R_{40}$, aryl, and heteroaryl; $R_{40}$ is $C_1$-$C_6$ alkyl.

In some embodiments wherein the dye of the invention has the structure of Formula B1, $R_2$ is selected from the group consisting of H, halogen, azido, cyano, $-NR_{21}R_{22}$, nitro ($-NO_2$), sulfonate ($-SO_3^-$), -L-$(Z)_m$, aryl, heteroaryl, $C_1$-$C_6$ alkyl, wherein each aryl, heteroaryl, $C_1$-$C_6$ alkyl, when present, is optionally substituted with halo, aryl, heteroaryl, $-NR_{21}R_{22}$, $OR_{23}$, $SR_{24}$, $-S(O)R_{25}$, $-S(O)_2R_{26}$, $-PR_{27}R_{28}$. In other embodiments, $R_2$ is selected from the group consisting of H, halogen, azido, cyano, $-NR_{21}R_{22}$, nitro ($-NO_2$), sulfonate ($-SO_3^-$), -L-$(Z)_m$, aryl, heteroaryl, $C_1$-$C_6$ alkyl. In still other embodiments, $R_2$ is selected from the group consisting of H, halogen, nitro (—$NO_2$), sulfonate (—$SO_3^-$), -L-$(Z)_m$, aryl, heteroaryl, $C_1$-$C_6$ alkyl. In some embodiments, $R_2$ is selected from the group consisting of H, halogen, azido, cyano, nitro (—$NO_2$), sulfonate (—$SO_3^-$), and $C_1$-$C_6$ alkyl. In some embodiments, $R_2$ is H. In other embodiments, $R_2$ is -L-$(Z)_m$.

In some embodiments wherein the dye of the invention has the structure of Formula B1, $R_2$ is selected from the group consisting of H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, or $C_1$-$C_6$ alkyl, when present, is optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$, —$NR_{29}$(C=O)$R_{30}$, —$NR_{31}S(=O)_2R_{32}$, or —C(=O)$NR_{33}R_{34}$; wherein each $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$ and $R_{35}$ is independently selected from the group consisting of H, $C_1$-$C_6$ alkyl, —C(=O)$R_{40}$, aryl, and heteroaryl; $R_{40}$ is $C_1$-$C_6$ alkyl.

In some embodiments wherein the dye of the invention has the structure of Formula B1, $R_3$ is selected from the group consisting of H, halogen, azido, cyano, —$NR_{21}R_{22}$, nitro (—$NO_2$), sulfonate (—$SO_3^-$), -L-$(Z)_m$, aryl, heteroaryl, $C_1$-$C_6$ alkyl, wherein each aryl, heteroaryl, $C_1$-$C_6$ alkyl, when present, is optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$. In other embodiments, $R_3$ is selected from the group consisting of H, halogen, azido, cyano, —$NR_{21}R_{22}$, nitro (—$NO_2$), sulfonate (—$SO_3^-$), -L-$(Z)_m$, aryl, heteroaryl, $C_1$-$C_6$ alkyl. In still other embodiments, $R_3$ is selected from the group consisting of H, halogen, nitro (—$NO_2$), sulfonate (—$SO_3^-$), -L-$(Z)_m$, aryl, heteroaryl, $C_1$-$C_6$ alkyl. In some embodiments, $R_3$ is selected from the group consisting of H, halogen, azido, cyano, nitro (—$NO_2$), sulfonate (—$SO_3^-$), and $C_1$-$C_6$ alkyl. In some embodiments, $R_3$ is H. In other embodiments, $R_3$ is -L-$(Z)_m$. In some embodiments, $R_3$ is sulfonate (—$SO_3^-$).

In some embodiments wherein the dye of the invention has the structure of Formula B1, $R_3$ is selected from the group consisting of H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, or $C_1$-$C_6$ alkyl, when present, is optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$, —$NR_{29}$(C=O)$R_{30}$, —$NR_{31}S(=O)_2R_{32}$, or —C(=O)$NR_{33}R_{34}$; wherein each $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$ and $R_{35}$ is independently selected from the group consisting of H, $C_1$-$C_6$ alkyl, —C(=O)$R_{40}$, aryl, and heteroaryl; and $R_{40}$ is $C_1$-$C_6$ alkyl.

In some embodiments wherein the dye of the invention has the structure of Formula B1, $R_4$ is selected from the group consisting of H, halogen, azido, cyano, —$NR_{21}R_{22}$, nitro (—$NO_2$), sulfonate (—$SO_3^-$), -L-$(Z)_m$, aryl, heteroaryl, $C_1$-$C_6$ alkyl, wherein each aryl, heteroaryl, $C_1$-$C_6$ alkyl, when present, is optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$. In other embodiments, $R_4$ is selected from the group consisting of H, halogen, azido, cyano, —$NR_{21}R_{22}$, nitro (—$NO_2$), sulfonate (—$SO_3^-$), -L-$(Z)_m$, aryl, heteroaryl, $C_1$-$C_6$ alkyl. In still other embodiments, $R_4$ is selected from the group consisting of H, halogen, nitro (—$NO_2$), sulfonate (—$SO_3^-$), -L-$(Z)_m$, aryl, heteroaryl, $C_1$-$C_6$ alkyl. In some embodiments, $R_4$ is selected from the group consisting of H, halogen, azido, cyano, nitro (—$NO_2$), sulfonate (—$SO_3^-$), and $C_1$-$C_6$ alkyl. In some embodiments, $R_4$ is H. In other embodiments, $R_4$ is -L-$(Z)_m$. In some embodiments, $R_4$ is sulfonate (—$SO_3^-$).

In some embodiments wherein the dye of the invention has the structure of Formula B1, $R_4$ is selected from the group consisting of H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, or $C_1$-$C_6$ alkyl, when present, is optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$, —$NR_{29}$(C=O)$R_{30}$, —$NR_{31}S(=O)_2R_{32}$, or —C(=O)$NR_{33}R_{34}$; wherein each $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$ and $R_{35}$ is independently selected from the group consisting of H, $C_1$-$C_6$ alkyl, —C(=O)$R_{40}$, aryl, and heteroaryl; and $R_{40}$ is $C_1$-$C_6$ alkyl.

In some embodiments wherein the dye of the invention has the structure of Formula B1, $R_5$ is selected from the group consisting of H, halogen, azido, cyano, —$NR_{21}R_{22}$, nitro (—$NO_2$), sulfonate (—$SO_3^-$), -L-$(Z)_m$, aryl, heteroaryl, $C_1$-$C_6$ alkyl, wherein each aryl, heteroaryl, $C_1$-$C_6$ alkyl, when present, is optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$. In other embodiments, $R_5$ is selected from the group consisting of H, halogen, azido, cyano, —$NR_{21}R_{22}$, nitro (—$NO_2$), sulfonate (—$SO_3^-$), -L-$(Z)_m$, aryl, heteroaryl, $C_1$-$C_6$ alkyl. In still other embodiments, $R_5$ is selected from the group consisting of H, halogen, nitro (—$NO_2$), sulfonate (—$SO_3^-$), -L-$(Z)_m$, aryl, heteroaryl, $C_1$-$C_6$ alkyl. In some embodiments, $R_5$ is selected from the group consisting of H, halogen, azido, cyano, nitro (—$NO_2$), sulfonate (—$SO_3^-$), and $C_1$-$C_6$ alkyl. In some embodiments, $R_5$ is H. In other embodiments, $R_5$ is -L-$(Z)_m$. In some embodiments, $R_5$ is sulfonate (—$SO_3^-$).

In some embodiments wherein the dye of the invention has the structure of Formula B1, $R_5$ is selected from the group consisting of H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, or $C_1$-$C_6$ alkyl, when present, is optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$, —$NR_{29}$(C=O)$R_{30}$, —$NR_{31}S(=O)_2R_{32}$, or —C(=O)$NR_{33}R_{34}$; wherein each $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$ and $R_{35}$ is independently selected from the group consisting of H, $C_1$-$C_6$ alkyl, —C(=O)$R_{40}$, aryl, and heteroaryl; and $R_{40}$ is $C_1$-$C_6$ alkyl.

In some embodiments wherein the dye of the invention has the structure of Formula B1, $R_1$, $R_2$, $R_3$, $R_4$ and $R_5$ are each independently H or sulfonate (—$SO_3^-$). In other embodiments, $R_1$, $R_2$, $R_3$, $R_4$ and $R_5$ are each H. In still other embodiments, $R_1$, $R_2$, $R_4$ and $R_5$ are H and $R_3$ is sulfonate (—$SO_3^-$).

In some embodiments wherein the dye of the invention has the structure of Formula B1, each $R_{21}$, $R_{22}$, $R_{23}$, $R_{24}$, $R_{25}$, $R_{26}$, $R_{27}$, $R_{28}$, and $R_{29}$ is independently H, $C_1$-$C_3$ alkyl optionally substituted with halo or $C_1$-$C_3$ alkyl. In some embodiments, each $R_{21}$, $R_{22}$, $R_{23}$, $R_{24}$, $R_{25}$, $R_{26}$, $R_{27}$, $R_{28}$, and $R_{29}$ is independently H or $C_1$-$C_3$ alkyl. In some embodiments, each $R_{21}$, $R_{22}$, $R_{23}$, $R_{24}$, $R_{25}$, $R_{26}$, $R_{27}$, $R_{28}$, and $R_{29}$ is independently H or $C_1$-$C_6$ alkyl.

In some embodiments wherein the dye of the invention has the structure of Formula B1, $R_6$ is $C_1$-$C_{12}$ alkyl, or is -L-$(Z)_m$. In other embodiments, $R_6$ is $C_1$-$C_{12}$ alkyl. In some embodiments, $R_6$ is $C_1$-$C_6$ alkyl. In other embodiments, $R_6$ is $C_1$-$C_3$ alkyl. In some embodiments, $R_6$ is methyl. In other embodiments, $R_6$ is -L-$(Z)_m$.

In some embodiments wherein the dye of the invention has the structure of Formula B1, $R_7$, $R_8$, $R_9$, $R_{10}$, $R_{11}$ and $R_{12}$ are independently H or halogen. In some embodiments, $R_7$, $R_8$, $R_9$, $R_{10}$, $R_{11}$ and $R_{12}$ are H. In some embodiments, at least one of $R_7$, $R_8$, $R_9$, $R_{10}$, $R_{11}$ and $R_{12}$ is halogen.

In some embodiments, $A_1$ and $A_2$ are each independently —$NR_{21}R_{22}$. In some embodiments, A1 and A2 are each —$NH_2$. In some embodiments, each $R_{21}$ and $R_{22}$ is H. In other embodiments, each $R_{21}$ and $R_{21}$ is independently H, $C_1$-$C_3$ alkyl optionally substituted with halo or $C_1$-$C_3$ alkyl.

In some embodiments, Y is a water soluble counter ion; and d is a number of Y sufficient for balancing the charge of Formula B1 as provided herein.

In some embodiments where the dye of the invention is of Formula B1, each Z is independently —$NR_{31}R_{32}$, —$N^+R_{33}R_{34}R_{35}$, or each Z is independently a group with a molecular weight of less than 450 and comprising one positive charge and one negative charge in neutral aqueous buffer. In some embodiments, each Z is independently —$NR_{31}R_{32}$ or —$N^+R_{33}R_{34}R_{35}$. In some embodiments, each Z is —$NR_{31}R_{32}$. In other embodiments, Z is —$N^+R_{33}R_{34}R_{35}$. In some embodiments, Z is selected from an amino group, a dialkyl amino group, a trialkylamonium group, and a heterocycle comprising a tetravalent nitrogen atom. Z can be a positively charged alkyl ammonium group. In other embodiments, each Z is independently a group with a molecular weight of less than 450 and comprising one positive charge and one negative charge in neutral aqueous buffer.

In some embodiments where the dye of the invention is of Formula B1, each $R_{31}$, $R_{32}$, $R_{33}$, $R_{34}$, and $R_{35}$ is independently $C_1$-$C_7$ alkyl, aryl, heteroaryl wherein each aryl, heteroaryl, $C_1$-$C_7$ alkyl, when present is optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$ and wherein ($R_{31}$ and $R_{32}$) or ($R_{34}$ and $R_{35}$) optionally connect to form a 3-, 4-, 5-, 6-, or 7-membered ring. $R_{31}$ and $R_{32}$ can connect to form a 3-, 4-, 5-, 6-, or 7-membered ring. $R_{34}$ and $R_{34}$ can connect to form a 3-, 4-, 5-, 6-, or 7-membered ring. In other embodiments $R_{31}$, $R_{32}$, $R_{33}$, $R_{34}$, and $R_{35}$ are each independently $C_1$-$C_7$ alkyl optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$.

In another embodiment, the dye of the invention is of Formula B1 wherein: at least one of $R_1$, $R_2$, $R_3$, $R_4$, and $R_5$ is sulfonate (—$SO_3^-$); $R_6$ is -L-$(Z)_m$; m is 1; and Z is amine or quaternized nitrogen.

In some embodiments, the dye of the invention is of Formula B1, wherein: at least one of $R_1$, $R_2$, $R_3$, $R_4$, $R_5$ and $R_6$ is -L-$(Z)_m$; and Z is a group with a molecular weight less than 450 comprising one positive charge and one negative charge in neutral aqueous buffer.

In some embodiments, each of $R_1$, $R_2$, $R_3$, $R_4$, and $R_5$ is independently selected from the group consisting of H, alkyl, amino, nitro, halogen atoms, sulfonate (—$SO_3^-$) and -L-Z; R6 is a substituted or unsubstituted alkyl, or is -L-Z; $R_7$, $R_8$, $R_9$, $R_{10}$, $R_{11}$ and $R_{12}$ are independently H or a halogen substituent; A1 and A2 are independently substituted or unsubstituted amino; Y is a water soluble counter ion; and d is the number of Y necessary for balancing the charge of formula B1.

L is a substantially neutral linker as defined for Formula A1 above. Z is an amine, a quarternized nitrogen or a zwitterionic moiety as defined previously herein. Here the quarternized nitrogen may be a trialkylammonium group or a quarternized nitrogen-containing heterocycle. In general, the quarternized nitrogen is a trialkylammonium group.

In another embodiment, one of $R_1$, $R_2$, $R_3$, $R_4$ and $R_5$ is a sulfonate and $R_6$ is -L-Z where Z is an amine or a quarternized nitrogen.

Further provided are phenanthridium dyes having the structure of Formula B2:

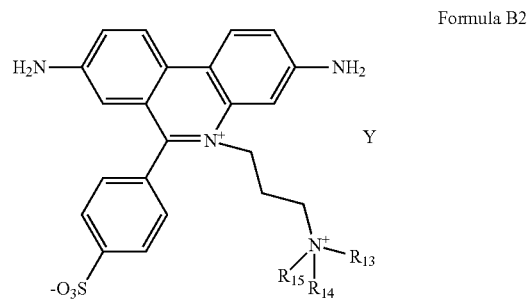

Formula B2 wherein each of $R_{13}$, $R_{14}$ and $R_{15}$ is independently a $C_1$-$C_4$ alkyl; Y is a water soluble counter ion. In some embodiments, $R_{13}$ is methyl and $R_{14}$ and $R_{15}$ are ethyl.

In some embodiments, a dye has the structure of Formula B1, where one of $R_1$, $R_2$, $R_3$, $R_4$, $R_5$ and $R_6$ is -L-$(Z)_m$. In some embodiments, the phenanthridium dye has the following Formula:

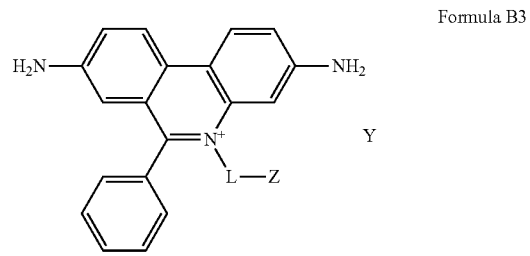

Formula B3 wherein L is linker chain of 2-12 carbon atoms optionally comprising one or more N, O or S atoms and Z is as defined previously herein. In some embodiments, -L-Z has the structure of Formula A21. In other embodiments, -L-Z has the structure of Formula A22 above.

Some non-limiting examples of phenanthridium dyes according to Formula B1, B2 and B3 are listed in Table 2 below:

TABLE 2

Phenanthridium dyes

| Dye No. | Structure |
|---|---|
| 9 | 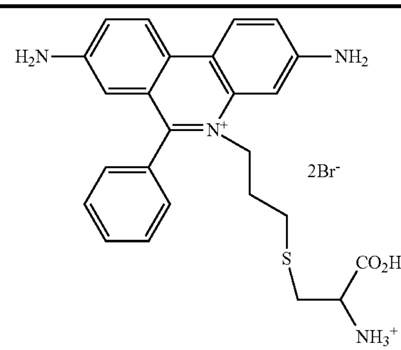 |

TABLE 2-continued

Phenanthridium dyes

| Dye No. | Structure |
|---|---|
| 10 | 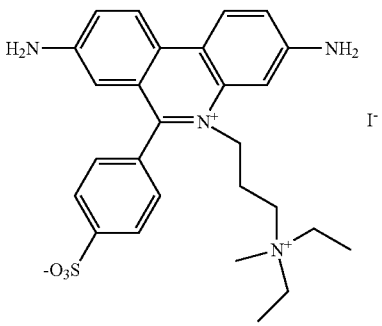 |
| 11 | 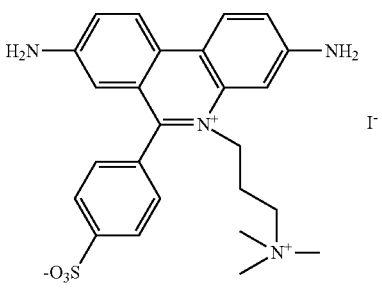 |
| 12 | 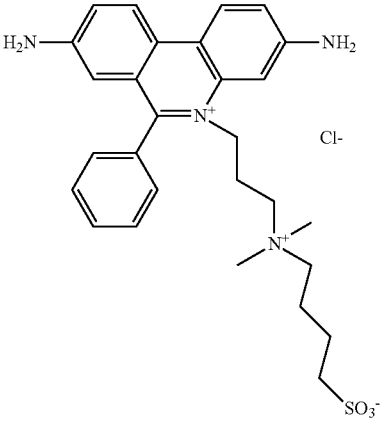 |

Also provided is an acridinium dye having the following Formula:

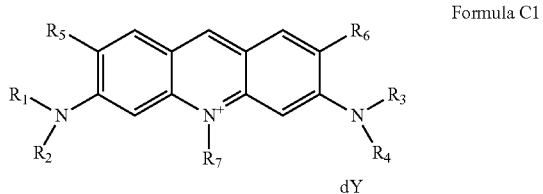

Formula C1 wherein:
$R_1$, $R_2$, $R_3$, $R_4$, are independently selected from H, aryl, heteroaryl, $C_2$-$C_6$ alkenyl, and $C_1$-$C_6$ alkyl, wherein said aryl, heteroaryl, $C_2$-$C_6$ alkenyl, and $C_1$-$C_6$ alkyl, when present, are optionally substituted with halo, aryl, or heteroaryl; $R_5$ and $R_6$ are independently selected from H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, and $C_1$-$C_6$ alkyl, when present, are optionally substituted with halo, aryl, or heteroaryl;

$R_7$ is -L-(Z)$_m$;

m is 1, 2, 3, or 4;

Y is a water soluble counter ion; and d is the number of Y necessary for balancing the charge of Formula C1;

wherein, each L is a linker chain of 2-12 carbon atoms and which contains zero or more N or O or S atoms;

each Z is a group with a molecular weight less than 300 comprising one positive charge and one negative charge in neutral aqueous buffer.

In some embodiments of the dye of the Formula C1, $R_1$, $R_2$, $R_3$, $R_4$, $R_5$ and $R_6$ are independently H or $C_1$-$C_3$ alkyl. In other embodiments, $R_1$, $R_2$, $R_3$, $R_4$, $R_5$ and $R_6$ are independently H or methyl. In still other embodiments, $R_1$, $R_2$, $R_3$ and $R_4$ are methyl; $R_5$ and $R_6$ are H; and -L-Z has the structure of Formula A21. In some embodiments, $R_1$, $R_2$, $R_3$ and $R_4$ are methyl; $R_5$ and $R_6$ are H; and -L-Z has the structure of Formula A22. In some embodiments, $R_1$, $R_2$, $R_3$ and $R_4$ are H; $R_5$ and $R_6$ are methyl; and -L-Z has the structure of Formula A21. In other embodiments, $R_1$, $R_2$, $R_3$ and $R_4$ are H; $R_5$ and $R_6$ are methyl; and -L-Z has structure of Formula A22 above.

In some embodiments wherein the dye of the invention has the structure of Formula C1, $R_1$ is selected from H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, and $C_1$-$C_6$ alkyl, when present, are optionally substituted with halo, aryl, or heteroaryl. In other embodiments, $R_1$ is selected from H, aryl, heteroaryl, $C_2$-$C_6$ alkenyl, and $C_1$-$C_6$ alkyl. In still other embodiments, $R_1$ is selected from H and $C_1$-$C_3$ alkyl. In some embodiments, $R_1$ is H or methyl. In other embodiments, $R_1$ is methyl. In some embodiments, $R_1$ is H.

In some embodiments wherein the dye of the invention has the structure of Formula C1, $R_2$ is selected from H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, and $C_1$-$C_6$ alkyl, when present, are optionally substituted with halo, aryl, or heteroaryl. In other embodiments, $R_1$ is selected from H, aryl, heteroaryl, $C_2$-$C_6$ alkenyl, and $C_1$-$C_6$ alkyl. In still other embodiments, $R_1$ is selected from H and $C_1$-$C_3$ alkyl. In some embodiments, $R_2$ is H or methyl. In other embodiments, $R_2$ is methyl. In some embodiments, $R_2$ is H.

In some embodiments wherein the dye of the invention has the structure of Formula C1, $R_3$ is selected from H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, and $C_1$-$C_6$ alkyl, when present, are optionally substituted with halo, aryl, or heteroaryl. In other embodiments, $R_3$ is selected from H, aryl, heteroaryl, $C_2$-$C_6$ alkenyl, and $C_1$-$C_6$ alkyl. In still other embodiments, $R_3$ is selected from H and $C_1$-$C_3$ alkyl. In some embodiments, $R_3$ is H or methyl. In other embodiments, $R_3$ is methyl. In some embodiments, $R_3$ is H.

In some embodiments wherein the dye of the invention has the structure of Formula C1, $R_4$ is selected from H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, and $C_1$-$C_6$ alkyl, when present, are optionally substituted with halo, aryl, or heteroaryl. In other embodiments, $R_4$ is selected from H, aryl, heteroaryl, $C_2$-$C_6$ alkenyl, and $C_1$-$C_6$ alkyl. In still other embodiments, $R_4$ is selected from H and $C_1$-$C_3$ alkyl. In some embodiments, $R_4$ is H or methyl. In other embodiments, $R_4$ is methyl. In some embodiments, $R_4$ is H.

In some embodiments wherein the dye of the invention has the structure of Formula C1, $R_5$ is selected from H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, and $C_1$-$C_6$ alkyl, when present, are optionally substituted with halo, aryl, or heteroaryl. In other embodiments, $R_5$ is selected from H, halo, azido, nitro, cyano, aryl, heteroaryl, $C_2$-$C_6$ alkenyl, and $C_1$-$C_6$ alkyl. In still other embodiments, $R_5$ is selected from H and $C_1$-$C_3$ alkyl. In some embodiments, $R_5$ is H or methyl. In other embodiments, $R_5$ is methyl. In some embodiments, $R_5$ is H.

In some embodiments wherein the dye of the invention has the structure of Formula C1, $R_6$ is selected from H, halo, azido, nitro, cyano, aryl, heteroaryl, $C_2$-$C_6$ alkenyl, and $C_1$-$C_6$ alkyl, wherein said aryl, heteroaryl, $C_2$-$C_6$ alkenyl, and $C_1$-$C_6$ alkyl, when present, are optionally substituted with halo, aryl, or heteroaryl. In other embodiments, $R_6$ is selected from H, halo, azido, nitro, cyano, aryl, heteroaryl, $C_2$-$C_6$ alkenyl, and $C_1$-$C_6$ alkyl. In still other embodiments, $R_6$ is selected from H and $C_1$-$C_3$ alkyl. In some embodiments, $R_6$ is H or methyl. In other embodiments, $R_6$ is methyl. In some embodiments, $R_6$ is H.

Some non-limiting examples of dyes according to Formula C1 are listed in table 3 below.

TABLE 3

Acridinium dyes

| Dye No. | Structure |
| --- | --- |
| 13 | [structure: acridinium core with two dimethylamino groups, N+ with propyl chain to S-CH2-CH(NH3+)(CO2-); counterion I-] |
| 14 | [structure: acridinium core with two dimethylamino groups, N+ with alkyl chain to C(=O)-NH-(CH2)3-CH(NH3+)(CO2-); counterion I-] |
| 15 | [structure: acridinium core with two dimethylamino groups, N+ with propyl chain to N+(CH3)-(CH2)4-SO3-; counterion I-] |

Figure 12:
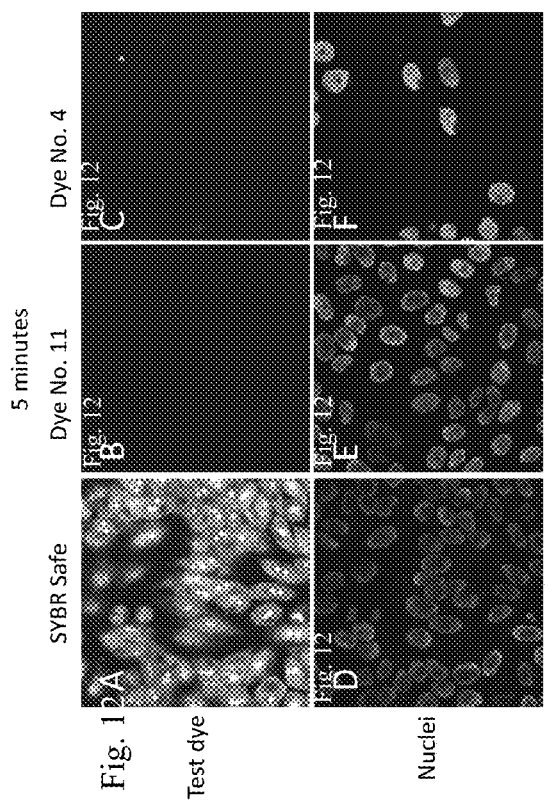
FIG. 12 shows the live cell staining of Dye No. 4, Dye No. 11, SYBR Safe and Hoechst 33342.
Figure 12:
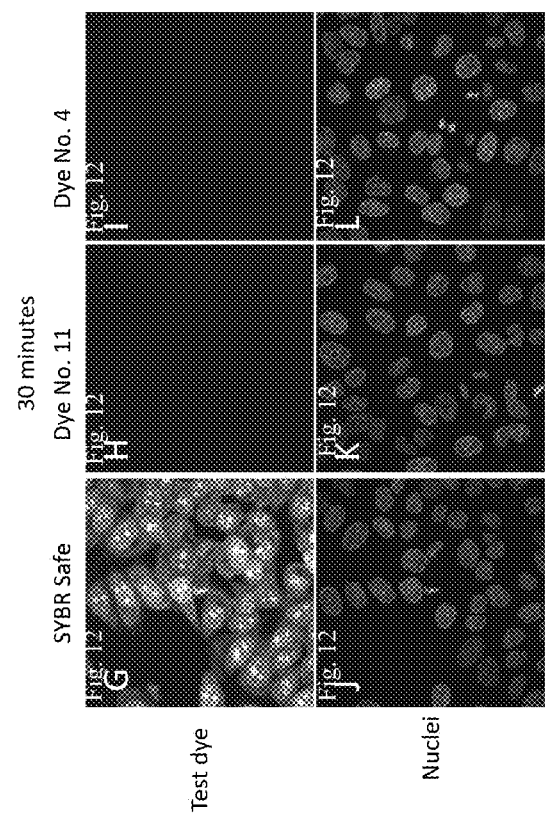

One advantage of the nucleic acid binding dyes of the invention is their improved safety. Nucleic acid binding dyes are inherently hazardous and sometimes very dangerous because of their potential to cause gene mutation in cells. Thus, many DNA binding dyes or nucleic acid binding dyes are either known carcinogens or treated as potential mutagens. For this reason, handling nucleic acid dyes usually requires special caution. Moreover, disposal of dye waste can also be costly. Other dyes commonly marketed as safe alternatives to ethidium bromide (including SYBR Safe; see, e.g. U.S. Pat. Nos. 7,727,716 and 7,977,057; and Evenson, et al. J Org Chem 77(23), 10967(2012) have failed to solve these problems. While SYBR Safe has been promoted as a safe nucleic acid gel stain based on a number of cell and animal toxicity tests (SYBR Safe gel stain white paper), the upper limits of the manufacturer-defined "safe dye concentration range" produced in several of the tests, such as Ames test and mammalian cell genotoxicity tests, are actually well below the 1× working concentration of the dye used in gel staining (See Example 30 for determination of SYBR Safe 1× concentration). Even at concentration below the 1× working concentration, SYBR Safe showed dose-dependent mutagenicity in some bacterial strains in the Ames test. Moreover, the dye showed cytotoxicity at very low concentration, which made the determination of mutagenicity information at higher dye concentrations not possible. Although the dye's acute oral toxicity was found to be low, the test was based on data obtained from merely 3 rats, which hardly yields any statistical significance. These results suggest that SYBR Safe may not be safe at its normal working concentration. Further SYBR Safe enters into cells rapidly, where fluorescence microscopy study revealed that the dye was largely localized in the cell nucleus area (FIG. 12). A study by Ohta, et al. to compare ethidium bromide and SYBR Green in their possible synergistic effect with UV light or other known mutagen in causing cell mutation, the authors found that both SYBR Green and ethidium bromide can worsen cellular mutation caused by UV light or the other known mutagens, but SYBR Green is nearly 100 times more powerful (Ohta, et al. Mutat Res 492, 91(2001)). In summary, these studies suggest that traditional genotoxocity tests alone may not be sufficient to fully assess the potential hazard of a nucleic acid binding chemical; cell membrane permeability of the chemical must also be considered because the chemical's entrance into cells is a prerequisite for genotoxicity.

While cell membrane permeability can be decreased by an increase in the charge of dyes, there are significant practical problems with this approach. One problem is the dyes' tight DNA binding, resulting from the high positive charge, which helps attract the negatively charge nucleic acid. One major application of these high affinity dyes is for high sensitivity nucleic acid detection (Markovits, et al. *Analytical Biochemistry* 94, 259(1979); U.S. Pat. No. 5,321,130). While the dyes can still be used as gel stains in some applications (Nucleic acid Research, 21, 5720(1993); Nature, 359, 859 (1992)), they are not suitable in applications where nucleic acid sample recovery is needed following the gel staining. In the latter applications, dye removal may be essential for any downstream analysis, such as cloning, PCR and sequencing. Relatively loosely bound dyes on nucleic acid can normally be removed during gel extraction. On the other hand, a high affinity dye may be difficult to remove, which can cause inaccurate analysis results due to the dye's interference. A second problem relates to the potential toxicity of the dyes once they are in the cells. Although these highly positively charged dyes may have low cell membrane permeability, it does not mean that they do not get into cells at all, especially under some conditions, such as high dye concentration, elevated temperature or the presence certain organic solvents, such as DMSO, which may facilitate the dye's entrance into cells. When a small number of the dyes do get into cells, they may pose even greater danger than less positively charged dyes. Finally, nucleic acid migration in gel matrix can slow down significantly in the presence of a high affinity dye. This may preclude the dye's use in precast gel staining because impeding the migration of nucleic acid will sacrifice the resolution of the separating nucleic acid bands.

Figure 10:
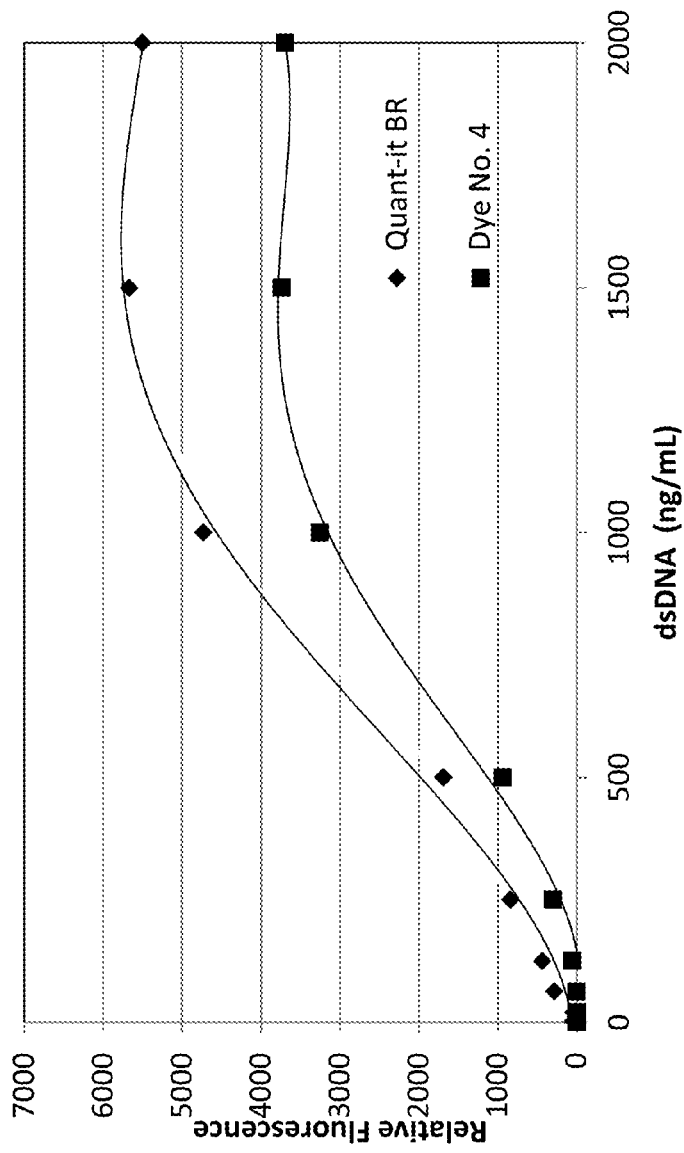
FIG. 10 shows the comparison between Dye No. 4 and Compound 25 of U.S. Pat. No. 7,655,409 in DNA detection in solution.
Figure 11:
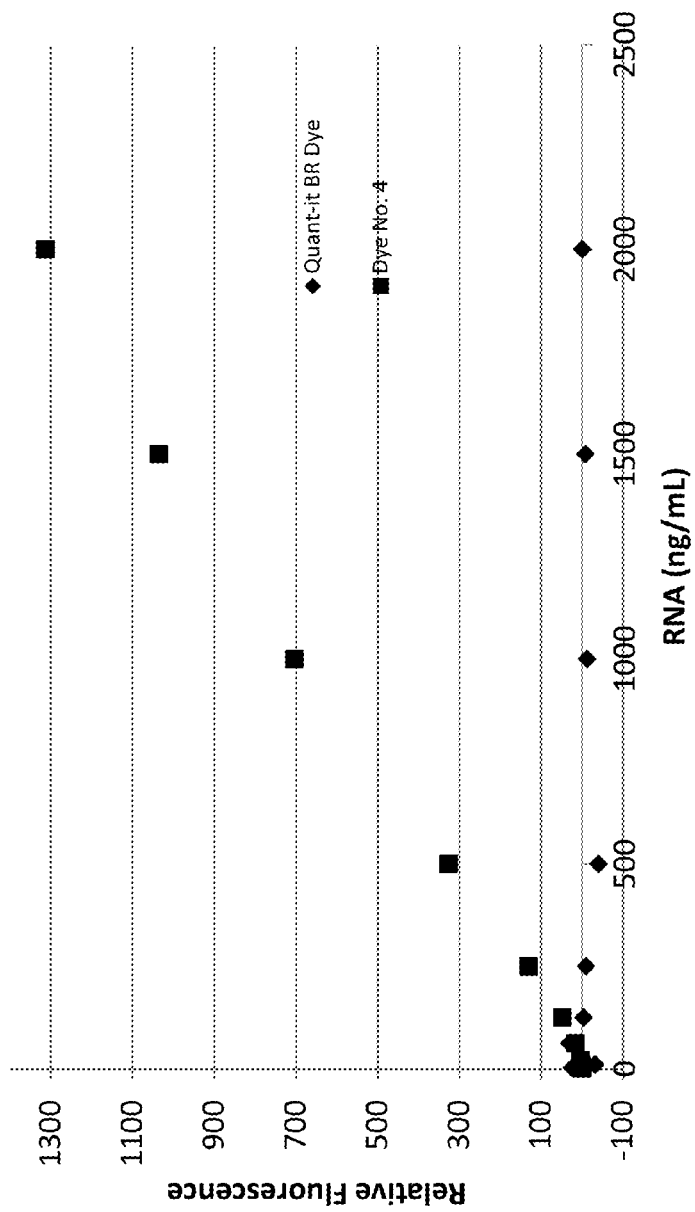
FIG. 11 shows the comparison between Dye No. 4 and Compound 25 of U.S. Pat. No. 7,655,409 in RNA detection in solution.

In some embodiments, dyes of the invention comprise a substituent comprising a zwitterionic moiety, where the positive charge and negative charge of the zwitterionic moiety are in close physical proximity. The zwitterionic moiety is superior to either positively charged or negatively charged substituents alone in that it provides the nucleic acid dye comprising the moiety optimal binding affinity for sensitive detection and sufficient polarity for reducing the dye's cell membrane permeability. Furthermore, unlike other dyes such as the dyes of U.S. Pat. No. 7,446,202, which have high selectivity for dsDNA in the presence of RNA, the asymmetric cyanine dyes of the invention do not greatly discriminate between dsDNA and RNA (FIGS. 10 and 11), suggesting that zwitterionic moiety and a negatively charged group alone affect the binding mechanism of nucleic acid dyes differently. It is advantageous for a single dye to be able to detect both DNA and RNA in gels by offering application versatility.

Figure 5:
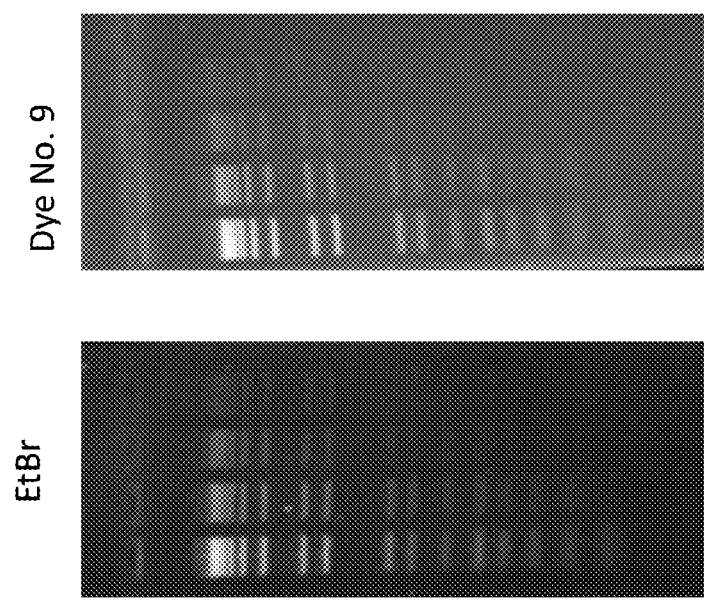
FIG. 5 shows the post staining of agarose gels with phenanthridium dye comprising a zwitterionic moiety (Dye No. 9 of Table 2). Two-fold dilutions of 1 kb DNA ladder (200 ng-25 ng per lane) were separated on 1% agarose TBE gels and then post-stained for 30 minutes in water with 5 µM Dye No. 9 or 0.5 ug/mL ethidium bromide (EtBr) as a reference.
Figure 6:
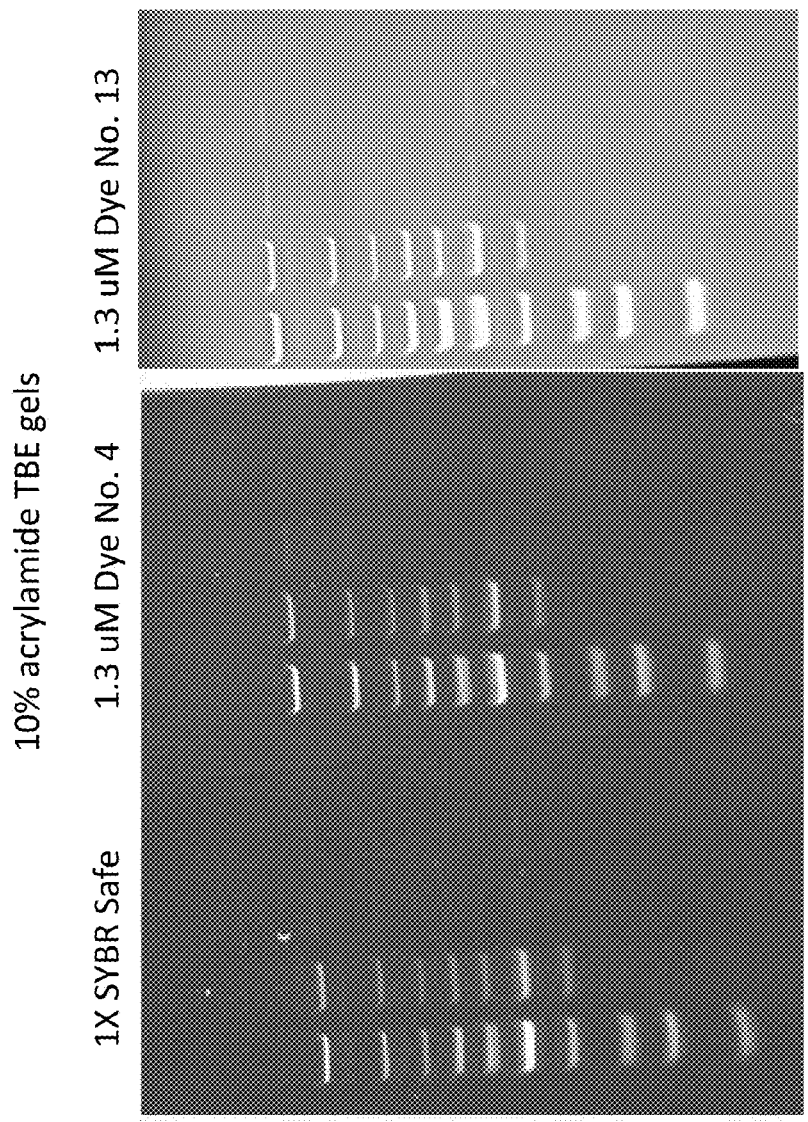
FIG. 6 shows the post staining of 10% polyacrylamide gels with SYBR Safe at 1×, Dye No. 4 at 1.3 µM and Dye No. 13 at 1.3 µM, respectively. Two-fold dilutions of low molecular weight DNA ladder (200 ng-50 ng per lane) were separated on 10% polyacrylamide TBE gels. Gels were post-stained for 30 minutes with each dye. Gels were imaged using a UV transilluminator and SYBR Safe filter with a 1.5 second exposure time.
Figure 7:
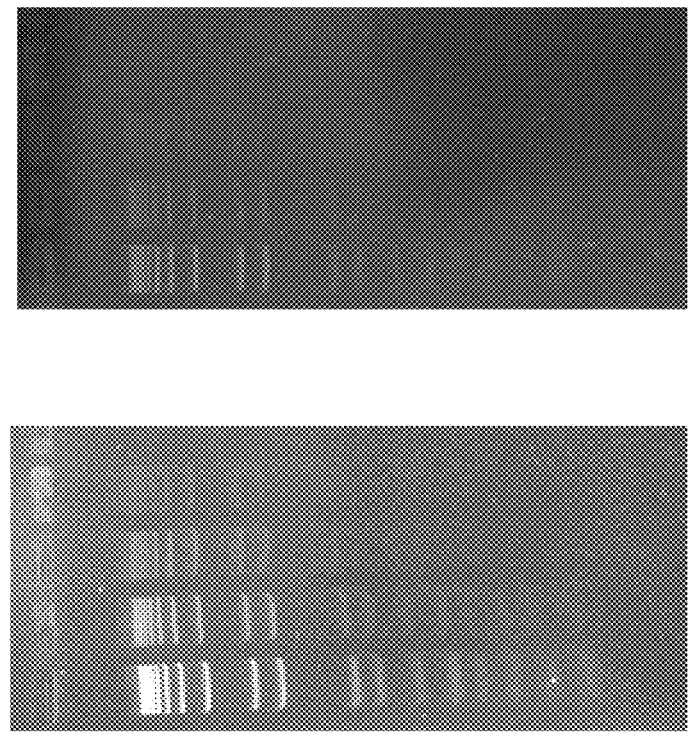
FIG. 7 shows post nucleic acid gel staining with sulfonated EtBr
Figure 8:
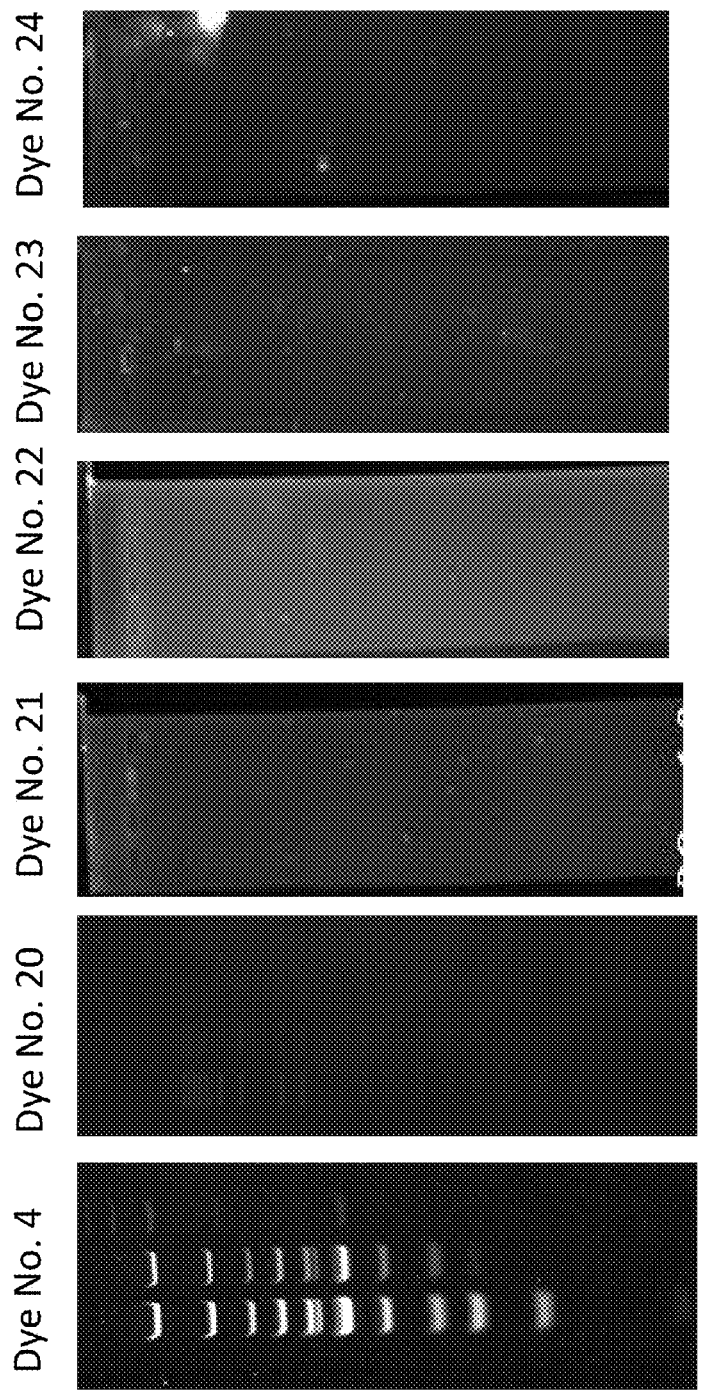
FIG. 8 shows the post staining of agarose gels with Dye No. 4 and various asymmetric cyanine dyes comprising one or more negative charge, respectively. Two-fold dilutions of 1 kb DNA ladder (200 ng-25 ng per lane) were separated on 1% agarose TBE gels and then post-stained for 30 minutes in water with 1.35 µM of an indicated asymmetric cyanine dye at 1.35 µM in water. See example 1 for staining and imaging procedures and see Examples 22, 25, 27, 28 and 29 for the structures of other asymmetric cyanine dyes comprising a negative substituent (Dye Nos 20-24).
Figure 9:
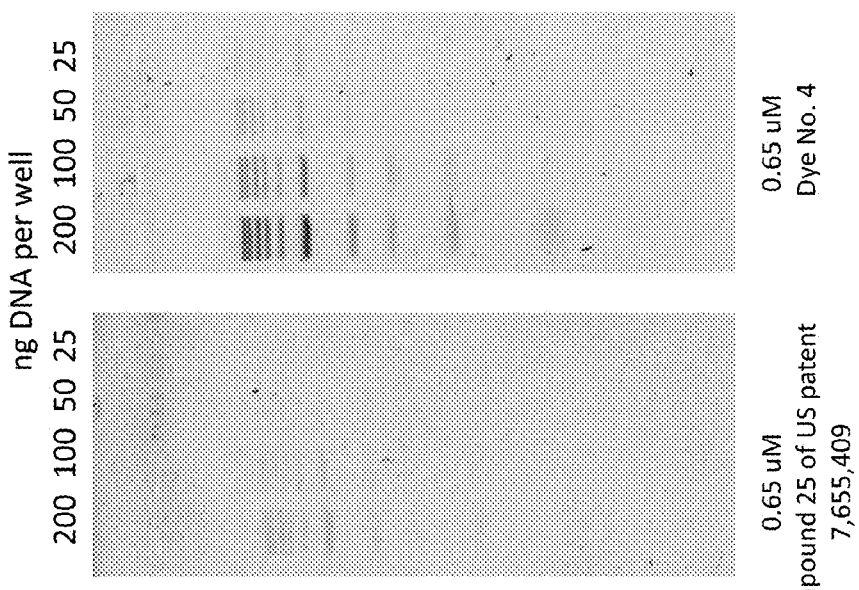
FIG. 9 shows the post staining of agarose gels with Dye No. 4 of Table 1 and Compound 25 of U.S. Pat. No. 7,655,409.
Figure 14:
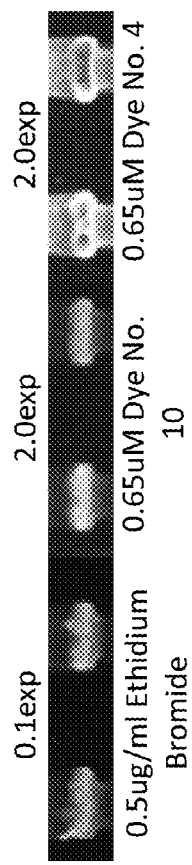
FIG. 14 shows agarose gel images demonstrating lack of dye carry over after gel extraction for nucleic acid samples in gel stained with dyes of the invention. A) nucleic acid samples post stained with EtBr, Dye No. 10 and Dye No. 4, respectively; B) nucleic acid samples after gel extraction with additional dye staining to show lack of dye carry over; and C) nucleic acid sample after gel extraction stained with GelRed (Biotium, Inc.) to show the presence of the samples.
Figure 14:
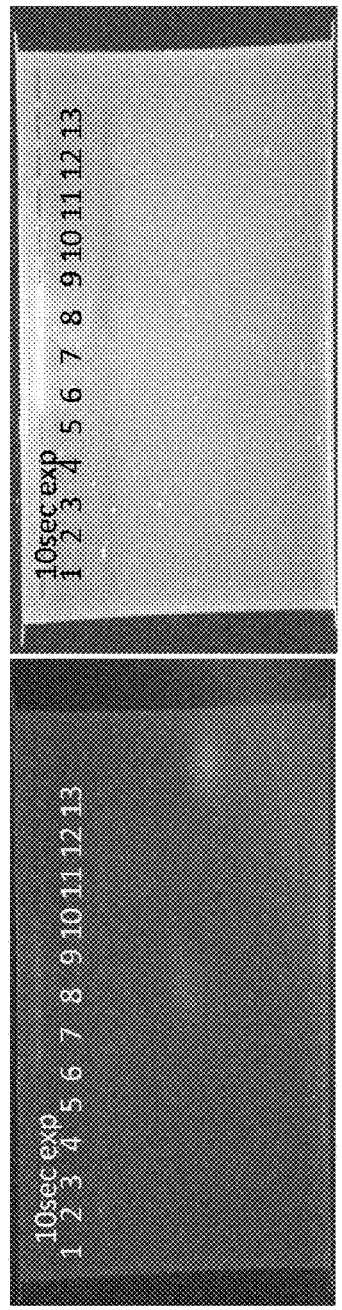
Figure 14:
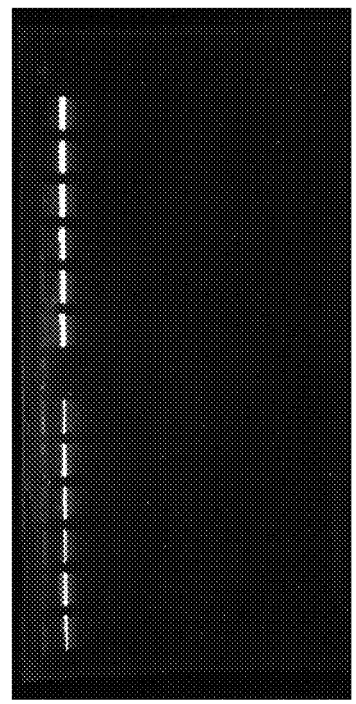

Zwitterionic moieties can also be present in phenanthridium dyes (FIG. 5) and acridinium dyes (FIG. 6) of the invention. Zwitterionic moieties as described herein can be successfully applied by anyone skilled in the art to any other nucleic acid binding dyes to achieve the benefits described in the invention. Nucleic acid dyes comprising a zwitterionic moiety may possess the proper nucleic acid binding affinity sufficiently high enough for sensitive nucleic acid detection in a gel matrix but not too high to make dye removal difficult when nucleic acid sample recovery is necessary. As an example, FIG. 14 shows that nucleic acid samples in gels stained with dyes of the inventions can be recovered using a gel extraction kit without any dye carryover. Equally importantly, the zwitterionic moiety provides the necessary polarity to render the dyes cell membrane impermeable, thereby reducing the dyes' toxicity.

The safety of the dyes of the invention have been evaluated using a number of methods. To assess the dyes' genotoxicity, Dye No. 4 and Dye No. 10 were chosen as examples to be subjected to Ames test, an industry standard test in which a subject chemical is examined for its ability to cause mutation in bacteria. The dyes were tested in 5 different bacterial strains and at various concentrations. Furthermore, to examine if the dyes are toxic after being metabolized, the tests were run in the presence and absence of S9 fraction (a pork liver enzyme extract), respectively. As shown by the results summarized in Example 9, Dye No. 4 and Dye No. 10 are nonmutagenic within the entire concentration range tested and in all five bacterial strains in the presence or absence of the S9 fraction. Moreover, no apparent cytotoxicity was observed either with the dyes even at the highest dye concentration. The upper limit of the dye concentration tested is 12 times of the typical dye concentration (0.65 uM) used in nucleic acid gel staining, thus providing sufficient safety margin for the dyes' handling and disposal. This is in contrast to SYBR Safe, for which the highest dye concentration declared safe by the manufacturer is actually below the 1× working concentration used in gel staining and furthermore a weak dose-dependent mutagenic toxicity was observed at below the 1× working concentration in four of the bacterial strains tested (*SYBR Safe DNA Gel Stain White Paper,* 2003).

A major contributing factor to the relatively low toxicity of dyes of the invention may be their low cell membrane permeability. As examples, when incubated with live cells at their normal working concentration used in gel staining, Dye No. 4 and Dye No. 11 of the invention did not produce any cellular staining at all while SYBR Safe stained cells rapidly, with most of the staining concentrated in the cell nuclear area (FIG. 12). A nucleic acid binding dye that can readily enter cells can cause cell damage in a number of ways, including damages of mitochondrial DNA and nuclear DNA and the interference of the natural DNA repair mechanism in cells (Ohta, 'et al. *Mutation Research* 492(1-2), 91(2001)). Thus, the cell staining data corroborate with the Ames test results and, more importantly, may suggest that the nonmutagenic property of the dyes observed in the Ames test can be extended to other cell lines.

Figure 13:
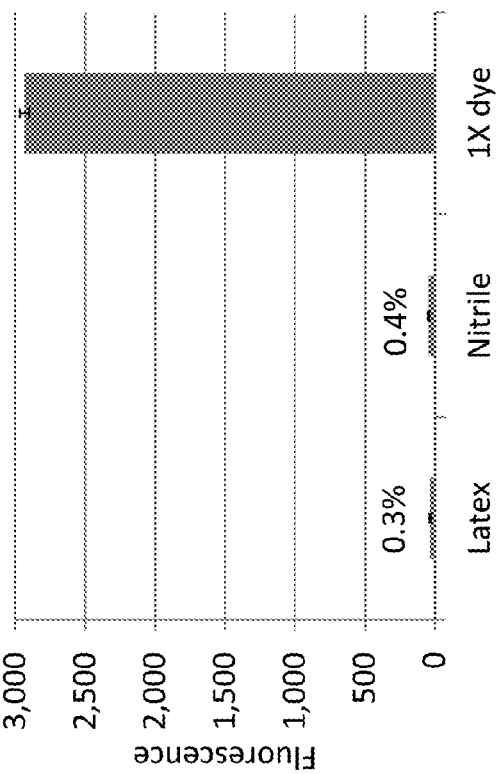
FIG. 13 shows the glove penetration test of Dye No. 4 and Dye No. 11.
Figure 13:
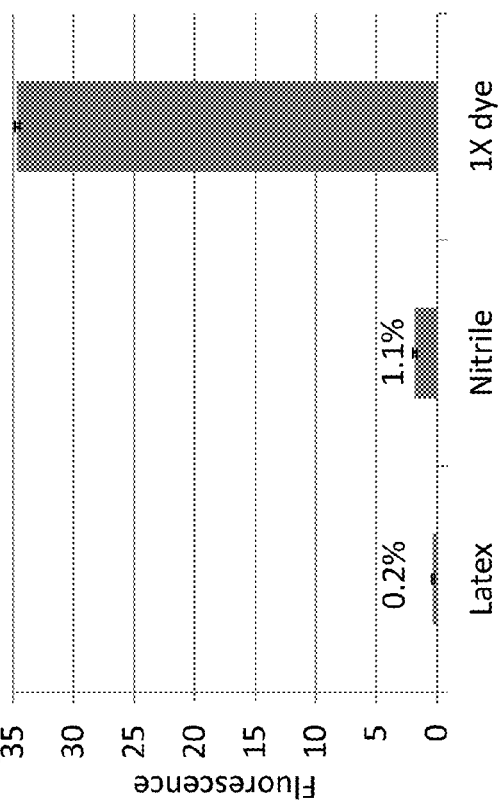

To further evaluate the safety of the dyes of the invention, the Dye No. 4 and Dye No. 11 were subject to glove penetration test, in which a concentrated dye solution (i.e., 5× of the typical concentration used in gel staining) is placed into a finger of a latex glove submerged in a small volume of a buffer and the optical density of the buffer at the dye's absorption wavelength is measured after 48 hours of incubation. As shown in FIG. 13, no significant amount of either Dye No. 4 or Dye No. 11 was leaked through the glove. This property of the dyes provides additional protection to the dye user during the application and disposal of the dyes.

Uses of the Dyes

The dyes of the invention can be useful for detecting nucleic acids, such as DNA or RNA. In particular, the dyes are useful for detecting nucleic acids embedded in a gel matrix (i.e., nucleic acid gel staining) with reduced hazard to the dye users during the handling and disposal of the dyes. Furthermore, the dyes possess nucleic acid binding affinity that can provide sensitive nucleic acid detection and at the same time facilitate dye removal following the detection when it is necessary to recover the nucleic acid sample.

In some embodiments, provided is a method of staining a nucleic acid embedded in a matrix or immobilized on a surface comprising the steps of: i) providing the nucleic acid sample; ii) providing a compound described herein (for example according to formula A1, B1 or C1); iii) combining the sample and compound for a time sufficient for the compound and nucleic acid to form a complex; iv) illuminating the complex with light and detecting the resulting fluorescence.

In some embodiments, provided is a method of staining a nucleic acid embedded in a matrix or immobilized on a surface comprising applying a fluorescent nucleic acid dye to said matrix or surface under conditions permitting formation of nucleic acid-dye complex, thereby staining a nucleic acid embedded in a matrix or immobilized on a surface, wherein: i) the nucleic acid binding dye shows no cell permeability, as ascertained by fluorescence microscopy in a human cell at a concentration of 0.20 µM to 2.0 µM; and ii) substantially complete water solubility at gel staining concentration; and iii) the nucleic acid binding dye does not show mutagenicity as determined in an Ames test at said concentration.

In some embodiments, provided is a method of staining a nucleic acid embedded in a matrix or immobilized on a surface comprising: applying a fluorescent nucleic acid dye of Formula A1, Formula B1, or Formula C1 to said matrix or said surface under conditions permitting formation of nucleic acid-dye complex, thereby staining said nucleic acid embedded in a gel. In some embodiments, upon formation of the dye-nucleic acid complex, visible bands appear that are indicative of size separation of individual fragments of nucleic acids from 10 base pairs to 150 base pairs. In other embodiments, the fragments of nucleic acids are from about 10 to about 130 or from about 10 to about 100 base pairs.

In some embodiments, the nucleic acid sample is embedded in a gel matrix. The gel matrix may comprise an agarose gel, a polyacrylamide gel or the like. In some embodiments, provided is a premixed agarose or polyacrylamide gel for the separation of nucleic acids comprising a compound of the invention. Agarose gels and polyacrylamide gels are widely used for electrophoretically separating nucleic acids. Agarose gels and polyacrylamide gels may have various densities as determined by the amount of agarose or polyacrylamide in the gels. For example, agarose gels for nucleic acid separation may comprise from about 0.2% to about 4% agarose, more typically from about 0.7% to about 2% agarose. Agarose gels can comprise 0.2% to 2% agarose. In another embodiment, the invention provides a precast agarose gel comprising from about 0.2% to about 4% agarose, a dye of the invention at 0.1 uM to 2 uM concentration and a buffer compatible with gel electrophoresis.

Similarly, polyacrylamide gels may comprise from about 4% to about 20% polyacrylamide in the gels. Polyacrylamide gels may comprise from about 10% to about 20% or from about 15% to about 20% polyacrylamide. Low density gels are primarily for separating high molecular weight nucleic acids while high density gels are more suitable for separating small nucleic acid fragments. Polyacrylamide gels are generally useful for separating small oligonucleotides, single stranded DNA and RNA fragments. For example, polyacrylamide gels can be used to analyze nucleic acid fragments as small as PCR primers, which can have from about 15 bases to about 30 bases. However, nucleic acid in dense gel matrix can be difficult to detect because many nucleic acid binding dyes may be slow to diffuse into the gel matrix to interact with the nucleic acid. For this reason, dimeric nucleic acid binding dyes, including those described in U.S. Pat. No. 7,601,498, may be physically too large to stain polyacrylamide gels. The dyes of the invention are generally monomeric and small in size and as a result can be used for staining both agarose gels and polyacrylamide gels.

In some embodiments, the step of combining the sample and the dye may take place after a gel electrophoresis to separate a nucleic acid sample is completed. This can be carried out by placing a gel comprising electrophoretically separated nucleic acid sample in a bath comprising a dye of the invention, where the gel is submerged in the dye solution to allow the dye to diffuse into the gel matrix and interact with the nucleic acid. This method of gel staining is sometimes referred to as post nucleic acid gel staining or post staining of nucleic acid gels.

In some embodiments, the step of combining the sample and the dye may take place during an gel electrophoresis as a nucleic acid sample is being separated. The dye may be in the electrophoresis buffer where it can diffuse into the gel matrix to combine with the nucleic acid. In other embodiments, the dye is pre-embedded in the gel matrix prior to the gel electrophoresis so that the nucleic acid can readily combine with the dye as the nucleic acid migrate in the gel matrix under the electric field. This latter method is commonly referred to as pre-cast nucleic acid gel staining. The gel comprising the pre-embedded nucleic acid binding dye is typically referred to as pre-cast nucleic acid gel. In some cases, the combining of the nucleic acid sample and the dye may comprise a combination of using a precast gel comprising a dye of the invention and adding the same dye or a different dye to the electrophoresis buffer.

In some embodiments, the provided dye is an asymmetric cyanine dye having the structure of formula A1, the structure of formula A2, and in some embodiments the structure of A3.

In other embodiments, the provided dye is a phenanthridium dye having the structure of formula B1. In some embodiments the structure of formula B2 or B3. In some embodiments, the dye has the structure of formula B2.

In still other embodiments, the provided dye has the structure of formula C1.

The incubation time necessary for the dye and nucleic acid to form the fluorescent complex may range from very little time, such as in the case of precast nucleic acid gel staining, where the migrating nucleic acid can nearly instantly interact with the dye pre-embedded in the gel matrix, to as long as 1 hour or longer time, such as in the case of post nucleic acid gel staining, where it may take time for the dye in the bath solution to diffuse into the gel matrix. In some embodiments, the incubation time for post nucleic acid gel staining is from about 5 minutes to about 2 hours, or from about 15 minutes to about 1 hour, or from about 20 minutes to about 40 minutes, or about 15, 20, 30, or 40 minutes.

The illumination and detection step may be carried out concurrently with the gel electrophoresis process when a precast gel comprising a dye of the invention is used. For example, there are commercially available gel electrophoresis instruments that are also equipped with a fluorescence imaging unit, permitting one to monitor the process of electrophoretic separation of a nucleic acid sample. Alternatively, the illumination and detection step may be carried out as a separate step following the completion of the gel electrophoresis. If a precast gel comprising a dye of the invention is used for the gel electrophoresis, the illumination and detection may be carried out following the gel electrophoresis step. If a regular gel that does not have a dye of the invention pre-embedded in the gel is used for the gel electrophoresis, a separate step of combining the dye and the nucleic acid sample and an incubation step as described above for the post gel staining method must proceed the illumination and detection step.

As an optional procedure, prior to the illumination and detection, the gel may be subject to a de-staining step by washing or rinsing the gel with a buffer or water to remove any nonspecifically stained dye. The destaining procedure may reduce background fluorescence and thus improve the signal-to-noise ratio of the detection. However, the dyes of the invention generally do not require the de-staining procedure because of the dyes' low intrinsic fluorescence.

The source of illumination may be a UV light with wavelength in range of 200 nm-350 nm. The dyes of the invention typically can have sufficient absorption in the UV light wavelength range. Thus UV light can be used as a common excitation source for all dyes of the invention. Alternatively, a visible light with wavelength closely matching the peak absorption wavelength of a dye of the invention can be used as the illumination source. In some cases, if sample recovery is desired, excitation with a visible light may be preferred over UV excitation because UV light may damage nucleic acid. Moreover, visible light is also generally safer than UV light to the dye user. For these reasons, various visible light-emitting diode (LED) lights have been increasingly used as excitation source for fluorescent dyes.

Various examples of nucleic acid gel staining using dyes of the invention and other reference dyes are shown in FIGS. 1-9.

The present invention also provides a staining solution comprising a dye according to the invention. In some embodiments, the dye concentration may be the dye's working concentration, typically referred to as 1× concentration. The solvent in the 1× staining solution is generally an aqueous solvent, such as water. In other embodiments, the staining solution may be in the form of a concentrated stock solution that can be readily diluted to the 1× working solution. The concentrated stock solution provides advantages for storage and shipping. In general, the dye in the stock solution is at least 2 times, 5 times, 10 times, 100 times, 1,000 times or 10,000 times concentrated relative to its working concentration. In some embodiments, the dye is 10,000 times concentrated relative to working concentration. The solvent in the stock solution may be an organic solvent, such as DMSO or DMF, or an aqueous solvent. In some embodiments, the solvent is water, which has the best safety advantage. In some embodiments, the staining solution may further comprise one or more agents selected from the group consisting of a loading dye for tracking gel electrophoresis, a high density chemical that facilitates sample loading into the wells of gels, a pH buffer agent and a detergent that facilitates the dissolution of the nucleic acid dye.

In some embodiments, provided is a kit comprising: i) a compound described herein; and ii) instructions instructing the use of the compound.

EXAMPLES

Example 1: Post Staining of Agarose Gels

Two-fold dilutions of 1 kb DNA ladder (Biotium, 200 ng-25 ng) or low-molecular weight DNA ladder (NEB, 50-12.5 ng/lane) were separated on 1% agarose/1×TBE gels in 1× TBE at 110 V for 90 minutes. Gels were post-stained with dyes at indicated concentrations in 50 mL staining solution with rocking for 30 minutes at room temperature, protected from light. The staining solutions were prepared by adding a dye stock solution in DMSO to water. Gels staining was imaged on a GelDoc-iT imaging system (UVP) using a UV transilluminator and either an ethidium bromide filter (for dyes of Formula B1, B2 or B3) or a SYBR Green filter (for dyes of Formula A1, A2, A3, or C1). The results show that dyes of the invention have excellent sensitivity in detecting nucleic acids in either agarose gels or polyacrylamide gels via post gel staining. In particular, dyes of the invention can readily penetrate dense polyacrylamide gels. See FIG. 1 and FIG. 5.

Example 2: Prestaining of Agarose Gels

Two-fold dilutions of 1 kb DNA ladder (200 ng-25 ng per lane) were mixed with propidium iodide (PI) or Dye No, 10 in DNA loading buffer at the final concentrations indicated and separated on 1% agarose TBE gels containing no additional DNA dye. Gels were imaged using a UV transilluminator with ethidium bromide filter with 3 seconds exposure time. The results show that despite the extra negative charge Dye No. 10 is as bright as PI for prestaining of gels. See FIG. 2.

Example 3: Effect of Dye Concentration in Post Staining of Agarose Gels

To determine the effective dye concentration for post nucleic acid gel staining, various concentrations of Dye No. 10 and Dye No. 4 were used to stain electrophoretically separated DNA ladders in 1% agarose gels as described in Example 1. As the data show, dye concentration as low as 0.3-0.65 uM can be used for the staining. Use of low dye concentration in the staining, coupled with the dyes' low cell membrane permeability (See below), makes the dyes safer to handle. See FIG. 3 and FIG. 4.

Example 4: Post Staining of Polyacrylamide Gels

Two-fold dilutions of low molecular weight DNA ladder (NEB, 200 ng-50 ng per lane) were separated on 10% or 15% acrylamide TBE gels. Gels were post-stained for 30 minutes with an indicated dye and indicated concentration in water. Gels were imaged using a UV transilluminator and ethidium bromide filter (for phenanthridium-based dyes) or SYBR filter (for asymmetric cyanine- or acridinium-based dyes) with a 1.5 second exposure time. See FIG. 6.

Example 5: Comparison of Dye No. 4 and Compound 25 of U.S. Pat. No. 7,446,202 in Post Staining of Agarose Gels Compound 25 of U.S. Pat. No. 7,446,202 is an asymmetric cyanine dye comprising a negatively charged substituent. The dye is described to be a sensitive dsDNA binding dye useful for selective dsDNA quantitation in solution. In this experiment, this dye is compared with the asymmetric cyanine dye Dye No. 4 of the present invention in detecting dsDNA in agarose gel. 1 kb DNA ladder (Biotium) was loaded on a 1% agarose/1×TBE gel at 200, 100, 50, or 25 ng per lane in duplicate and separated by electrophoresis at 100V. The gel was cut in half, and each half was stained for 30 minutes at room temperature with either 0.65 uM Quant-iT Broad Range dsDNA dye (Life Technologies) in water or 0.65 uM Dye No. 4 in water, then imaged on a UVP GelDoc-iT system using a UV transilluminator and SYBR Green filter, with 2 second exposure time. The image colors were inverted to improve clarity in reproduction. The gel stained with Dye No. 4 shows significantly higher signal than the gel stained with Compound 25.

Example 6: Comparison Between Compound 25 of U.S. Pat. No. 7,446,202 and Dye No. 4 of Table 1 in their Nucleic Acid Binding Profile Compound 25 of U.S. Pat. No. 7,446,202 and Dye No. 4 were compared in nucleic acid detection in solution. Calf Thymus DNA (Sigma) was used to titrate 2 uM Dye No. 4 or 1.3 uM Compound 25 of U.S. Pat. No. 7,446,202 in TE buffer. The fluorescence of the solution was measured on a fluorescence microplate reader (200 uL volume/well and 5 minutes incubation time). Same optical setting was used for both dyes as the two dyes have nearly identical spectral profile. The data show that Compound 25 of U.S. Pat. No. 7,446,202 is highly selective for dsDNA whereas Dye No. 4 binds to both dsDNA and RNA, suggesting that the nucleic acid binding mechanisms of the two dyes are fundamentally different. See FIGS. 8-10.

Example 7: Live Cell Staining

Dye No. 4, Dye No. 9 and SYBR Safe are tested for their cell membrane permeability. HeLa cells were incubated with 1× Sybr Safe, 0.65 uM Dye No 4 and 0.65 uM Dye No. 11 in cell culture medium at 37 C. Hoechst 33342 (1 ug/mL) was included to stain DNA with blue fluorescence. Cells were imaged after 5 minutes and 30 minutes incubation on the appropriate fluorescence channel (FITC for Sybr Safe and Dye No. 4, and Cy3 for Dye No. 10) on a Zeiss LSM 700 confocal microscope.

After 5 minutes (A) and 30 minutes (G) incubation with 1× Sybr Safe, cells showed bright green fluorescent staining in the cytoplasm and nucleus. In contrast, no staining was detectable after 5 minutes (B, C) or 30 minutes (H, I) of incubation with Dye No. 4 or 0.65 uM Dye No. 11, indicating that unlike Sybr Safe, these dyes do not readily penetrate cell membranes. Hoechst staining for the same microscopic field is shown below each image (D-F, J-L). See FIG. 11.

Example 8: Glove Permeability Test

Glove fingers from latex and nitrile gloves were filled with 5 mL of 1×TAE buffer and immersed in a 20 mL glass scintillation vial containing 10 mL of 1×TAE buffer containing 3.25 uM Dye No. 11 or Dye No. 4 at 3.25 uM, which is 5× the optimal concentration used for staining gels (0.65 uM). A solution of 3.25 uM dye was stored in a glass vial without glove material to monitor the degree of dye adsorption to the glass and the glove material. After 48 hours, aliquots of solution from inside the glove finger, outside the glove finger, and from the stored dye solution were transferred to wells of a black 96-well plate containing 20 ug dsDNA per well to enhance dye fluorescence. Fluorescence was measured using a SpectraMax Gemini fluorescence plate reader at the optimal excitation and emission settings for each dye. After 48 hours of continuous exposure to dye solution, a minimal amount of dye was detectable inside of the glove fingers. The percentages shown on the graphs represent the percentage of 5× dye that was detected inside the glove finger. See FIG. 12.

Example 9: Mutagenicity Test of Dye No. 4 and Dye No. 10

To assess the mutagenicity of Dye No. 4 and Dye No. 10, standard Ames tests were performed by BioReliance Corporation (Rockville, Md.). Stock solutions of Dye No. 10 and Dye No. 4 in water were submitted to BioReliance for bacterial reverse mutation assay. The tester strains used were *Salmonella typhimurium* histidine auxotrophs TA98, TA100, TA1535, and TA1537 and *Escherichia coli* WP2 uvrA. Exposure to mutagens causes these strains to revert from auxotrophy to prototrophy. Reversion of strains TA98 and TA1535 is caused by frameshift mutations. Reversion of strain TA1535 and *E. coli* reversion is caused by base pair substitution. Reversion of strain TA100 is caused by both frame shift and base pair substitution mutations.

Compounds were tested in the assay as described by Ames et al. (Ames, B N, Mcann, J, and Yamasaki, E. (1975). Methods for detecting carcinogens and mutagens with the *Salmonella*/mammalian microsome mutagenicity test. Mut Res 31: 347-364) and updated by Maron and Ames (Maron, D M and Ames, B N. (1983). Revised methods for the *Salmonella* mutagenicity test. Mut Res 113: 173-215). The compounds were tested at eight dose levels along with vehicle control and positive control compounds in the presence and absence of Aroclor-induced rat liver S9 fraction. Rat liver S9 activation is used to simulate conversion of non-mutagenic compound to mutagenic metabolites by exposed cells or tissues. All dose levels and controls were tested in duplicate. The assay was carried out for 48-72 hours at 37 C. Plates were examined for compound precipitate and colonies were counted using an automated colony counter or manually. For a compound to be evaluated as positive for mutagenicity, it must cause a dose-related increase in the mean revertants per plate of at least one tester strain over a minimum of two increasing concentrations of test article. Data sets for strains TA1537 and TA1537 were judged positive if the increase in mean revertants at the peak of the dose is equal to or greater than three times the vehicle control. Data sets for strains TA98, TA100, and WP2 uvrA were deemed positive if the increase in mean revertants was greater than two times the vehicle control.

The dose levels tested of Dye No. 10 and Dye No. 4 were 0.1, 0.3, 0.65, 1.3, 2.5, 5, 7.5, and 10 uM per plate. The highest dose tested corresponds to approximately 15-fold higher than the optimal concentration used for staining gels (0.65 uM). No precipitation, toxicity, or mutagenicity was observed for either compound at any of the doses tested, with or without S9 activation. Based on these results, of Dye No. 10 and Dye No. 4 were deemed to be non-toxic and non-mutagenic at concentrations well above the typical working concentration.

Example 10: Title 22 Toxicity Test Results for Hazardous Waste Characterization Stock solutions of Dye No. 11 and Dye No. 4 at 0.65 uM each in water were submitted to Nautilus Environmental (San Diego, Calif.) for California Title 22 toxicity testing for hazardous waste characterization. The solutions were tested at 750, 500, and 250 mg/L plus lab control in *Pimephales promelas* (Fathead minnow) in two replicates of 10 fish each according to the California Department of Fish and Game 1988 Acute Procedures. Samples must results in greater than 50% survival at 500 mg/L (median lethal concentration or $LC_{50}$>500 mg/L) to be classified as "not hazardous." Both dye solutions resulted in a median lethal concentration ($LC_{50}$ value)>750 mg/L; therefore both dye solutions passed and can therefore be classified as non-hazardous to aquatic life under CCR Title 22 regulations.

Example 11: Gel Extraction of Nucleic Acids in Agarose Gels

For dye carryover testing, approximately 5 ug linearized plasmid DNA was run on a 1% agarose/1×TBE gel in 1×TBE at 100 V for 30 minutes. Gels were post-stained with dyes in 50 mL staining solution with rocking for 40 minutes at room temperature, protected from light. Gel staining was imaged on a GelDoc-iT imaging system (UVP) using a UV transilluminator and either an ethidium bromide or a SYBR Green filter. Fragments were excised and purified using silica spin column based gel extraction kits. Approximately 250-500 ng purified DNA from each sample was run on a 1% agarose/1×TBE gel in 1× TBE at 100V for 40 minutes. The gels were then imaged at various exposure times to check for dye carryover on a GelDoc-iT imaging system (UVP) using a UV transilluminator and either an ethidium bromide or a SYBR Green filter. Afterwards, the gel was post-stained with 3× GelRed in 50 mL staining solution with rocking for 30 minutes at room temperature, protected from light, and imaged again using the same system to verify even loading of purified DNA samples.

Results are shown in FIG. 13. Panel A shows nucleic acid samples in gels post stained with EtBr, Dye No. 10 and Dye No. 4, respectively. Panel B shows images of the extracted samples. Approximately 250 ng (Lanes 1-6) or 500 ng (lanes 8-13) purified DNA from each sample was run on a 1% agarose/1×TBE gel in 1×TBE at 100V for 40 minutes. The gels were then imaged at various exposure times (10 second exposure shown here) to check for dye carryover. Lanes 1, 2, 8, and 9 contain samples from the gel originally stained with Ethidium Bromide, lanes 3, 4, 10, and 11 contain samples from the gel originally stained with Dye No. 10, and lanes 5, 6, 12, and 13 contain samples from the gel originally stained with Dye No. 4. Samples 1, 3, 5, 8, 10, and 12 were purified using Biotium's DNA Gel Extraction Kit, and samples 2, 4, 6, 9, 11, and 13 were purified using the Qiagen QuiQuick Gel Extraction Kit. Lane 7 was not loaded with any sample. Gels were exposed for up to 12 seconds at a time with no visible dye carryover. Faint lines on each indicate visualization of the loading dyes included in the loading buffer. Panel C shows the same gel as in Panel B but stained with GelRed to verify that the sample loading was even. See FIG. 13.

Example 12: Preparation of Sulfonated EtBr

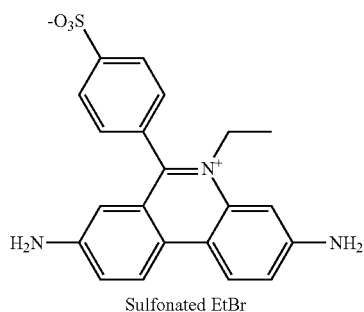

Sulfonated EtBr

To 30% fuming sulfuric acid (5 mL) at 0° C. was add ethidium bromide (0.5 g, 1.26 mmol)(Aldrich cat#: E8751-25G) portionwise over a period of 15 minutes. The mixture was stirred at 0° C. for 1 hr and then at room temperature overnight. The mixture was poured into Et$_2$O (200 mL) that was cooled at −70° C. The precipitate was collected by suction filtration and then purified by column chromatography on silica gel to give Compound No. 1 as dark red solid (120 mg). MS calcd for $C_{21}H_{20}N_3O_3S^+$ [M=H]$^+$ 394. found 394.

Example 13: Preparation of Dye No. 10

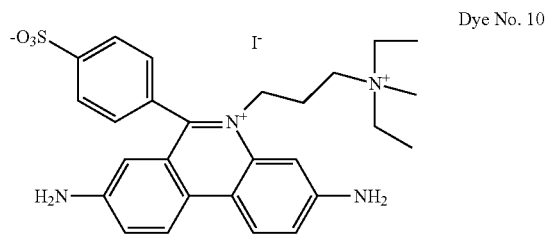

Dye No. 10

To 30% fuming sulfuric acid (5 mL) at 0° C. was add propidium iodide (0.5 g, 0.74 mmol)(Biotium cat#: 40016) portionwise over a period of 15 minutes. The mixture was stirred at 0° C. for 1 hr and then at room temperature overnight. The mixture was poured into Et$_2$O (200 mL) cooled at −70° C. The precipitate was collected by suction filtration and then purified by preparative reverse phase HPLC to give a red compound. The red compound was redissolved in 5 mL water and then added to 5 mL water containing 200 mg NaI. The resulting precipitate was collected by suction filtration and then dried under high vacuum to give the final product Dye No. 10 (210 mg). MS calcd for $C_{27}H_{33}N_4O_3S^+$[M]$^+$ 493. found 493.

Example 14: Preparation of 3,8-bis(carboethoxyamino)-5-(3-iodopropyl)-6-phenylphenanthridium, iodide

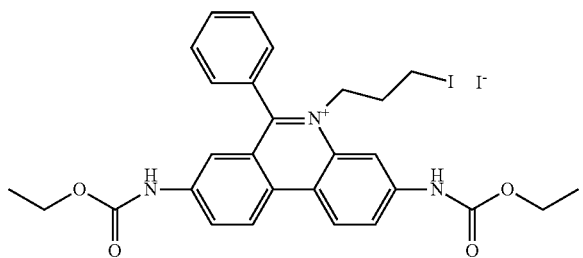 [SMILES: CCOC(=O)Nc1ccc2c(c1)c(-c1ccccc1)[n+](CCCI)c1cc(NC(=O)OCC)ccc21 ; [I-]]

A mixture of 3,8-bis(carboethoxyamino)-6-phenylphenanthridine (15.2 g, 35.4 mmol) (prepared according to J Chem Soc., 3059, 1952), 1,3-diiodopropane (41 mL, 354 mmol) and chlorobenzene (15 mL) was heated at 130° C. for 24 hours. After cooling down to 85° C., EtOAc (30 mL) was added and the suspension was refluxed gently for 1 hour. After cooling down to room temperature, the titled compound (21 g) was collected by suction filtration as yellow solid.

Example 15: 3,8-bis(carboethoxyamino)-6-phenyl-5-(3-(N,N,N-trimethylammoniumpropyl)-6-phenylphenanthridium, diiodide

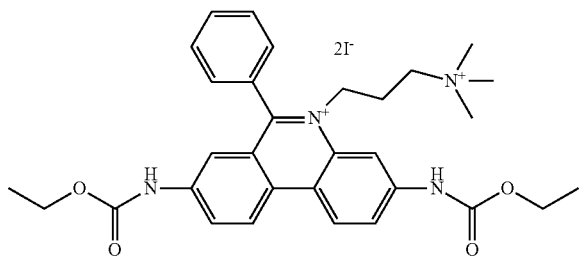

A mixture of 3,8-bis(carboethoxyamino)-5-(3-iodopropyl)-6-phenylphenanthridium, iodide from Example 14 (5 g) and 40% trimethylamine in methanol (100 mL) was stirred at 80° C. for 2 days. The solvent was removed by rotary evaporation. The crude product was recrystallized from methanol to give the titled compound (2 g).

Example 16: Preparation of 3,8-diamino-6-phenyl-5-(3-(N,N,N-trimethylammoniumpropyl)-6-phenyl-phenanthridium, dibromide

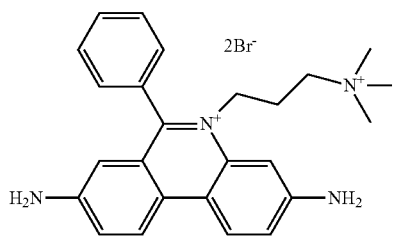 [SMILES: C[N+](C)(C)CCC[n+]1c(-c2ccccc2)c2cc(N)ccc2c2ccc(N)cc21]

A mixture of 3,8-bis(carboethoxyamino)-6-phenyl-5-(3-(N,N,N-trimethylammoniumpropyl)-6-phenylphenanthridium, diiodide (0.15 g, 0.22 mmol) in 48% aqueous hydrobromic acid (3 mL) was heated to 100° C. overnight. After cooling down to room temperature, the precipitate was collected by suction filtration. The precipitate was suspended in $CH_3CN$ (5 mL) and stirred at room temperature overnight. The titled compound (50 mg) was collected by suction filtration as yellow solid.

Example 17: Preparation of Dye No. 11

Dye No. 11

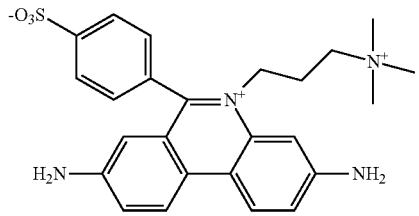

Dye No. 11 (15 mg) was synthesized from 3,8-diamino-6-phenyl-5-[3-(trimethylammonio)propyl phenanthridinium, diiodide (66 mg, 0.1 mmol) according to the procedure of Example 13. MS calcd for $C_{25}H_{29}N_4O_3S^+$ [M]$^+$ 465. Found 465.

Example 18: Preparation of Dye No. 9

Dye No. 9

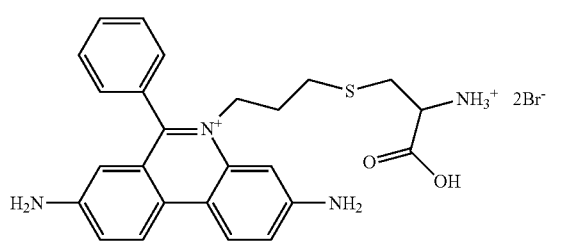

To a solution of 3,8-bis(ethoxycarbonylamino)-5-(3-iodopropyl)-6-phenyl-phenanthridinium, iodide (4.64 g, 7.76 mmol, Example 14) in DMF (150 mL) was added diisopropylethylamine (12 mL, 69 mmol) and cysteine hydrochloride (4 g, 23.3 mmol). The mixture was stirred at room temperature overnight and then concentrated to dryness in vacuo. To the residue was added water (350 mL) and the suspension was stirred at room temperature overnight. The precipitate (1 g) in 48% aqueous hydrobromic acid (10 mL) was heated to 100° C. overnight. After cooling down to room temperature, the precipitate was collected by suction filtration. The precipitate was suspended in $CH_3CN$ (15 mL) and stirred at room temperature overnight. Dye No. 9 (0.2 g) was collected by suction filtration as yellow solid. MS calcd for $C_{31}H_{35}N_4O_6S^+$ [M]$^+$ 591. found 591.

Example 19: Preparation of Dye No. 13

Dye No. 13

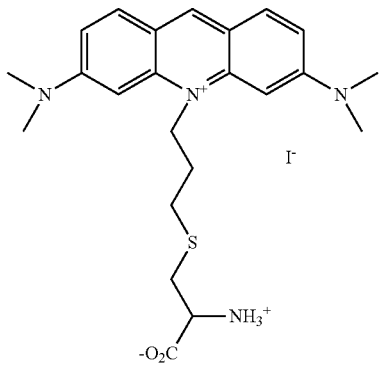

To a solution of 10-iodopropylacridinium, iodide (0.42 g, 0.75 mmol) (prepared according to U.S. Pat. No. 7,601,492) in DMF (20 mL) was added N,N-diisopropylethylamine (2 mL, 11 mmol) and cysteine hydrochloride (0.65 g, 3.75 mmol). The mixture was stirred at room temperature overnight and then concentrated to dryness in vacuo. To the residue was added water (50 mL) and the suspension was stirred at room temperature overnight. The precipitate was collected by suction filtration and purified by preparative reverse phase HPLC to give Dye No. 13 as orange solid (95 mg). MS calcd for $C_{23}H_{31}N_4O_2S^+$ [M]$^+$ 427. found 427.

Example 20: Preparation of Dye. No. 4

Dye No. 4

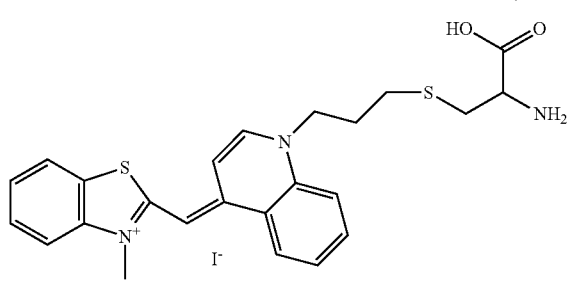

A mixture of 1-(3-iodopropyl)-4-[(3-methyl-2(3H)-benzothiazolylidene)methyl]quinolinium iodide (0.15 g, 0.26 mmol) (prepared according to J. Am. Chem. Soc., 64, 199(1942)), cysteine hydrochloride (0.22 g, 1.28 mmol) and sodium acetate (0.1 g, 1.28 mmol) in DMF (10 mL) was stirred at room temperature overnight. The mixture was concentrated to dryness in vacuo. Water (20 mL) was added to the residue and the suspension was stirred at room temperature overnight. The precipitate was collected by suction filtration and purified by preparative reverse phase HPLC to give Dye No. 4 as orange solid (10 mg). MS calcd for $C_{24}H_{26}N_3O_2S_2^+$ $[M]^+$ 452. found 452.

Example 21: Preparation of Dye No. 22

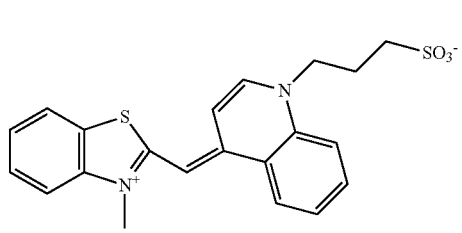

Dye No. 22

A mixture of 2,3-dimethylthiobenzothiazolinum tosylate (2.63 g, 7.17 mmol), 1-(3-sulfopropyl)quinolinium inner salt (2 g, 7.54 mmol, prepared by quarternizing quinoline with propane sultone) and triethylamine (1.05 mL, 7.54 mmol) in DMF (20 mL) was stirred at room temperature overnight. The precipitate was collected by suction filtration. The precipitate was suspended in $CH_3CN$ (50 mL) and stirred at room temperature overnight. The precipitate was collected by suction filtration to give Dye No. 22 as orange solid (2.3 g). calcd for $C_{21}H_{21}N_2O_2S_2^+$ $[M+H]^+$ 413. found 413.

Example 22: Preparation of Dye No. 25

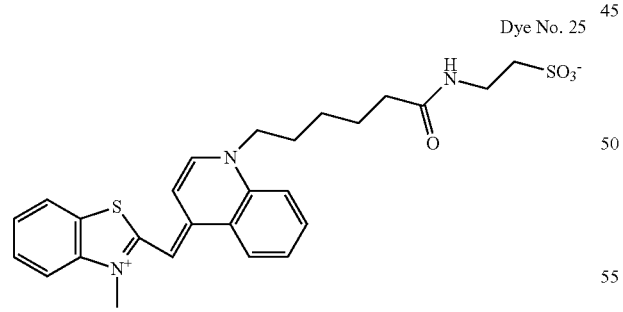

Dye No. 25

To a solution of 1-(5-carboxypentyl)-4-[(3-methyl-2 (3H)-benzothiazolylidene)methyl]quinolinium iodide (0.5 g, 0.94 mmol) (prepared according to Org. Lett. 6(4), 517(2004)) in DMF (5 mL) at room temperature was added diisopropylethylamine (0.82 mL, 4.7 mmol) and TSTU (0.3 g, 0.98 mmol). The mixture was stirred at room temperature for 15 minutes and then added to a solution of taurine (0.35 g, 2.82 mmol) in water (100 mL) at 0° C. The suspension was stirred at 0° C. for 3 hrs and the precipitate was collected by suction filtration to give Compound No. 9 as orange solid (0.65 g). MS calcd for $C_{26}H_{30}N_3O_4S_2^+$ $[M+H]^+$ 512. found 512.

Example 23: Preparation of 4-methyl-1-(3-(N,N,N-trimethylammonium)propylquinolinium dibromide

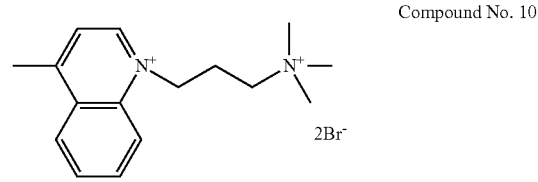

Compound No. 10

A mixture of lepidine (2.16 g, 15.3 mmol) and (3-bromopropyl)trimethylammonium bromide (2 g, 7.7 mmol) in DMF (20 mL) was heated at 100-110° C. for 7 hours. After cooling down to room temperature, the solution was concentrated to dryness in vacuo. EtOAc (50 mL) was added and the suspension was stirred at room temperature for 8 hours. The precipitate was collected by centrifugation and dried to a constant weight to give the title compound as an off-white solid (0.5 g).

Example 24: Preparation of 2-methylmercapto-3-sulfobutylbenzothiazolium

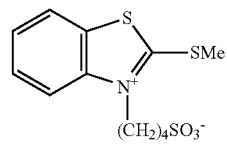

A mixture of 2-methylthiobenzothiazole (5 g, 27.6 mmol) and 1,4-butanesultone (3.4 mL, 33.1 mmol) in EtOAc (10 mL) was heated to reflux overnight. After cooling down to room temperature, the titled compound (3 g) was collected by suction filtration as white precipitate.

Example 25: Preparation of Dye No. 20

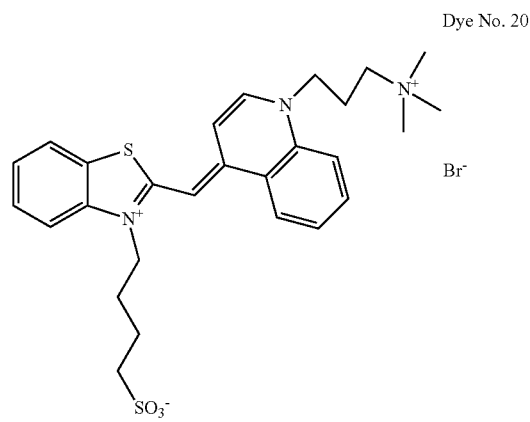

Dye No. 20

To a solution of 3-sulfobutyl-2-methylthiobenzothiazolinum inner salt (93 mg, 0.29 mmol) and triethylamine (136 µL, 1.0 mmol) in DMF (1.5 mL) was added a solution of Compound No. 10 (202 mg, 0.5 mmol) in DMF (2.5 mL). The reaction was stirred at room temperature for 4 hours. The reaction was concentrated under reduced pressure. The residue was washed several times with methanol and dried to a constant weight to give pure Compound No. 11 as orange solid (45 mg). MS calcd for $C_{27}H_{34}N_3O_3S_2^+$ $[M]^+$ 512. found 512.

Example 26: Preparation of 4-methyl-1-(4-sulfobutyl)quinolium

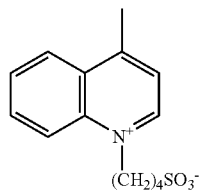

A mixture of lepidine (2.6 mL, 20 mmol) and 1,4-butane sultone (3.8 mL, 36.7 mmol) was heated at 100° C. for 2 hours. After cooling down to room temperature, EtOAc (35 mL) was added and the suspension was refluxed for 1 hour. The titled compound (4 g) was collected by suction filtration as white solid.

Example 27: Preparation of Dye No. 21

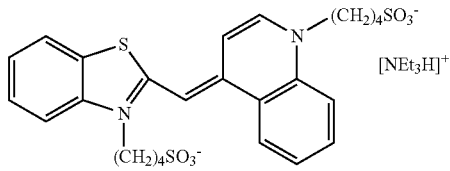

Dye No. 21

To a solution of 3-sulfobutyl-2-methylthiobenzothiazolinum inner salt (31 mg, 0.098 mmol) and triethylamine (68 µL, 0.49 mmol) in DMF (1.5 mL) was added 1-(3-sulfobutyl)-4-methylquinolinium inner salt (27.5 mg, 0.098 mmol). The reaction was stirred at room temperature for 2 hours then more DMF (2.0 mL) was added. The reaction was stirred at room temperature overnight. The product was collected by vacuum filtration and washed with acetonitrile. The solid was dried to a constant weight to give Dye No. 21 as an orange solid (20 mg).

Example 28: Preparation of Dye No. 23

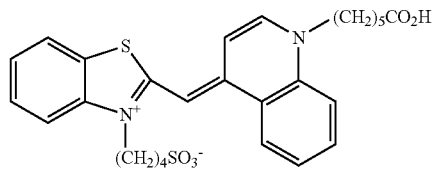

Dye No. 23

To a solution of Compound No. 11 (31 mg, 0.098 mmol) and triethylamine (68 µL, 0.49 mmol) in DMF (1.5 mL) was added 1-(5-carboxypentyl)-4-methylquinolinium bromide (33.0 mg, 0.098 mmol) (prepared according to Org. Lett. 6(4), 517, 2004). The reaction was stirred at room temperature overnight. The product was collected by vacuum filtration and washed with acetonitrile. The solid was dried to a constant weight to give Dye No. 23 as an orange solid (13 mg). $C_{27}H_{31}N_2O_5S_2^+$ $[M+H]^+$ 527. found 527.

Example 29: Preparation of Dye No. 24

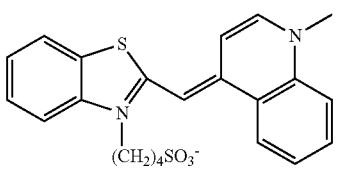

Dye No. 24

To a solution of 2-methylmercapto-3-sulfobutylbenzothiazolium (31 mg, 0.098 mmol) and triethylamine (68 µL, 0.49 mmol) in DMF (1.5 mL) was added 1,4-dimethylquinolinium tosylate (32.0 mg, 0.098 mmol). The reaction was stirred at room temperature overnight. The product was collected by vacuum filtration and washed with acetonitrile. The solid was dried to a constant weight to give Compound No. 16 as an orange solid (15 mg). $C_{22}H_{23}N_2O_3S_2^+$ $[M+11]^+$ 427. found 427.

Example 30: Determination of SYBR Safe 1× Dye Concentration

The 1× working concentration of SYBR Safe is not disclosed by the manufacturer. However, the dye's chemical structure has been determined to be an asymmetric cyanine dye, similar to Thiazole Orange (Evenson, et al. J Org Chem 77(23), 10967(2012)). The extinction coefficient of Thiazole Orange (Sigma-Aldrich) is determined to be ~70,000. Using this extinction coefficient and the optical density of SYBR Safe 1× solution, the concentration of the 1× was determined to be ~1.3 µM.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula B1:

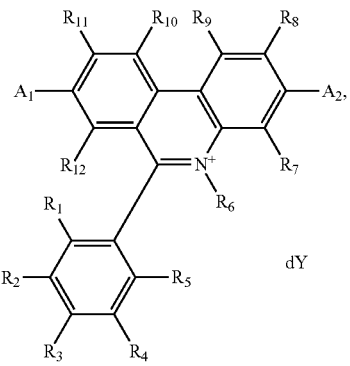

Formula B1 wherein:
$R_1$, $R_2$, $R_3$, $R_4$, and $R_5$ are each independently selected from the group consisting of H, halogen, —$NR_{21}R_{22}$, nitro (—$NO_2$), sulfonate (—$SO_3^-$), L-(Z), aryl, heteroaryl, and $C_1$-$C_6$ alkyl, wherein each aryl, heteroaryl, and $C_1$-$C_6$ alkyl is optionally substituted with halo, aryl, heteroaryl, —$NR_{21}R_{22}$, $OR_{23}$, $SR_{24}$, —$S(O)R_{25}$, —$S(O)_2R_{26}$, or —$PR_{27}R_{28}$;
each $R_{21}$, $R_{22}$, $R_{23}$, $R_{24}$, $R_{25}$, $R_{26}$, $R_{27}$, and $R_{28}$ is independently H or $C_1$-$C_3$ alkyl that is optionally substituted with halo or $C_1$-$C_3$ alkyl;
$R_6$ is -L-(Z)$_m$;
each m is independently 0, 1, 2, or 3;
$R_7$, $R_8$, $R_9$, $R_{10}$, $R_{11}$ and $R_{12}$ are each independently H or halogen;
$A_1$ and $A_2$ are each independently —$NR_{21}R_{22}$;
Y is a water soluble counter ion; and d is a number of Y sufficient for balancing the charge of Formula B1;
each L is a linker chain of 2-12 carbon atoms optionally comprising one or more N, O or S atoms;
each Z is independently —$NR_{31}R_{32}$ or —$N^+R_{33}R_{34}R_{35}$, or each Z is independently a group with a molecular weight of less than 450 and comprising one positive charge and one negative charge in neutral aqueous buffer;
each $R_{31}$, $R_{32}$, $R_{33}$, $R_{34}$, and $R_{35}$ is independently $C_1$-$C_7$ alkyl, aryl, or heteroaryl, wherein each aryl, heteroaryl, or $C_1$-$C_7$ alkyl is optionally substituted with halo, aryl, heteroaryl, —$NR_{21}R_{22}$, $OR_{23}$, $SR_{24}$, —$S(O)R_{25}$, —$S(O)_2R_{26}$, or —$PR_{27}R_{28}$ and wherein ($R_{31}$ and $R_{32}$) or ($R_{34}$ and $R_{35}$) optionally connect to form a 3-, 4-, 5-, 6-, or 7-membered ring; and
wherein at least one of $R_1$, $R_2$, $R_3$, $R_4$, and $R_5$ is —$SO_3$.

2. The compound of claim 1, wherein:
m is 1; and
Z is amine or quaternized nitrogen.

3. The compound of claim 1, wherein:
Z is a group with a molecular weight less than 450 comprising one positive charge and one negative charge in neutral aqueous buffer.

4. The compound of claim 1, having the structure of Formula B2:

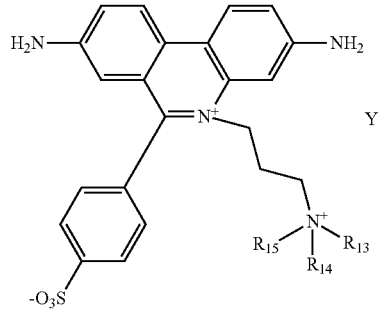

Formula B2 wherein $R_{13}$, $R_{14}$, and $R_{15}$ are each independently $C_1$-$C_4$ alkyl; and
Y is an anion.

5. The compound of claim 1, having the formula:

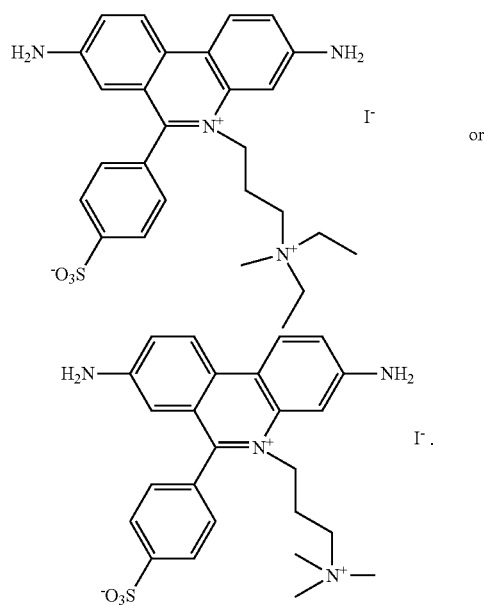

or

6. The compound of claim 1, wherein at least one of $R_1$, $R_2$, $R_3$, $R_4$, and $R_5$ is —$SO_3$, and the remaining are each independently H or —$SO_3^-$.

7. The compound of claim 6, wherein $R_1$, $R_2$, $R_4$, and $R_5$ are each H and $R_3$ is —$SO_3^-$.

8. The compound of claim 1, wherein $R_7$, $R_8$, $R_9$, $R_{10}$, $R_{11}$, and $R_{12}$ are each H.

9. The compound of claim 1, wherein $A_1$ and $A_2$ are each —$NH_2$.

10. The compound of claim 1, wherein each Z is independently —$NR_{31}R_{32}$ or —$N^+R_{33}R_{34}R_{35}$.

11. The compound of claim 10, wherein $R_{31}$, $R_{32}$, $R_{33}$, $R_{34}$, and $R_{35}$ are each independently $C_1$-$C_7$ alkyl.

12. The compound of claim 1, wherein m is 1.

13. The compound of claim 1, wherein -L(Z)$_m$ is selected from the group consisting of:

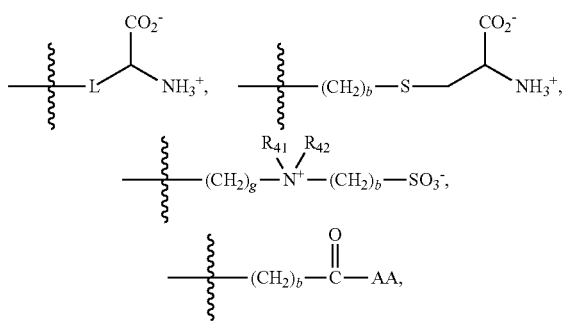

-L-NR$_{31}$R$_{32}$, and -L-N$^+$R$_{33}$R$_{34}$R$_{35}$,
wherein:
b and g are each independently 2, 3, 4, 5, 6, 7 or 8;
R$_{41}$ and R$_{42}$ are each independently H or C$_1$-C$_8$ alkyl; and
AA is an amino acid.

14. The compound of claim 4, wherein R$_{13}$, R$_{14}$, and R$_{15}$ are each independently methyl or ethyl.

15. A compound of Formula B1:

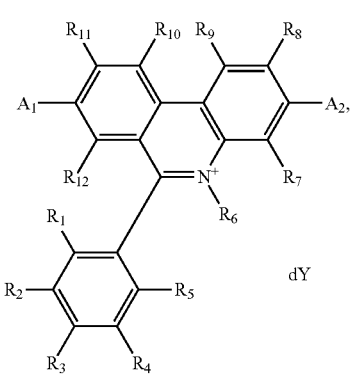

wherein:
R$_1$, R$_2$, R$_4$, and R$_5$ are each H;
R$_3$ is sulfonate (—SO$_3^-$);
R$_6$ is C$_1$-C$_{12}$ alkyl or -L-(Z)$_m$;
each m is independently 0, 1, 2, or 3;
R$_7$, R$_8$, R$_9$, R$_{10}$, R$_{11}$ and R$_{12}$ are each independently H or halogen;
A$_1$ and A$_2$ are each independently —NR$_{21}$R$_{22}$;
Y is a water soluble counter ion; and d is a number of Y sufficient for balancing the charge of Formula B1;
each L is a linker chain of 2-12 carbon atoms optionally comprising one or more N, O or S atoms;
each Z is independently —NR$_{31}$R$_{32}$ or —N$^+$R$_{33}$R$_{34}$R$_{35}$, or each Z is independently a group with a molecular weight of less than 450 and comprising one positive charge and one negative charge in neutral aqueous buffer;
each R$_{31}$, R$_{32}$, R$_{33}$, R$_{34}$, and R$_{35}$ is independently C$_1$-C$_7$ alkyl, aryl, or heteroaryl, wherein each aryl, heteroaryl, or C$_1$-C$_7$ alkyl is optionally substituted with halo, aryl, heteroaryl, —NR$_{21}$R$_{22}$, OR$_{23}$, SR$_{24}$, —S(O)R$_{25}$, —S(O)$_2$R$_{26}$, or —PR$_{27}$R$_{28}$ and wherein (R$_{31}$ and R$_{32}$) or (R$_{34}$ and R$_{35}$) optionally connect to form a 3-, 4-, 5-, 6-, or 7-membered ring; and
each R$_{21}$, R$_{22}$, R$_{23}$, R$_{24}$, R$_{25}$, R$_{26}$, R$_{27}$, and R$_{28}$ is independently H or C$_1$-C$_3$ alkyl that is optionally substituted with halo or C$_1$-C$_3$ alkyl.

16. A compound of Formula B1:

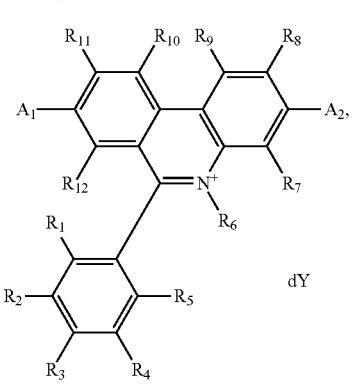

wherein:
R$_1$, R$_2$, R$_3$, R$_4$, and R$_5$ are each independently selected from the group consisting of H, halogen, —NR$_{21}$R$_{22}$, nitro (—NO$_2$), sulfonate (—SO$_3^-$), aryl, heteroaryl, and C$_1$-C$_6$ alkyl, wherein each aryl, heteroaryl, and C$_1$-C$_6$ alkyl is optionally substituted with halo, aryl, heteroaryl, —NR$_{21}$R$_{22}$, OR$_{23}$, SR$_{24}$, —S(O)R$_{25}$, —S(O)$_2$R$_{26}$,

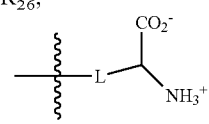

wherein L is a linker chain of 2-12 carbon atoms optionally comprising one or more N, O, or S atoms,

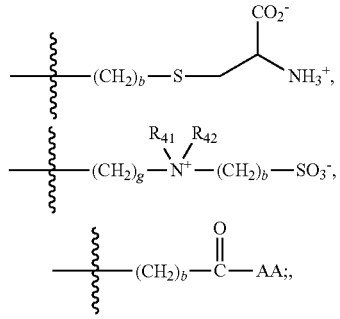

-L-NR$_{31}$R$_{32}$, and -L-N$^+$R$_{33}$R$_{34}$R$_{35}$, or —PR$_{27}$R$_{28}$;
each R$_{21}$, R$_{22}$, R$_{23}$, R$_{24}$, R$_{25}$, R$_{26}$, R$_{27}$, and R$_{28}$ is independently H or C$_1$-C$_3$ alkyl that is optionally substituted with halo or C$_1$-C$_3$ alkyl;
R$_7$, R$_8$, R$_9$, R$_{10}$, R$_{11}$ and R$_{12}$ are each independently H or halogen;
A$_1$ and A$_2$ are each independently —NR$_{21}$R$_{22}$;
Y is a water soluble counter ion; and d is a number of Y sufficient for balancing the charge of Formula B1;
R$_6$ is selected from the group consisting of:

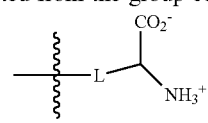

wherein L is a linker chain of 2-12 carbon atoms optionally comprising one or more N, O, or S atoms,

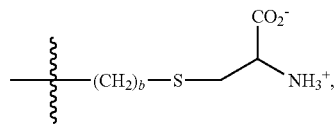

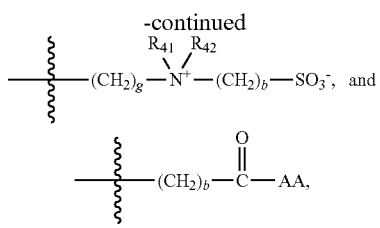

b and g are each independently 2, 3, 4, 5, 6, 7 or 8;
$R_{41}$ and $R_{42}$ are each independently H or $C_1$-$C_8$ alkyl;
AA is an amino acid; and
each $R_{31}$, $R_{32}$, $R_{33}$, $R_{34}$, and $R_{35}$ is independently $C_1$-$C_7$ alkyl, aryl, or heteroaryl, wherein each aryl, heteroaryl, or $C_1$-$C_7$ alkyl is optionally substituted with halo, aryl, heteroaryl, —$NR_{21}R_{22}$, $OR_{23}$, $SR_{24}$, —$S(O)R_{25}$, —$S(O)_2R_{26}$, or —$PR_{27}R_{28}$ and wherein ($R_{31}$ and $R_{32}$) or ($R_{34}$ and $R_{35}$) optionally connect to form a 3-, 4-, 5-, 6-, or 7-membered ring.

17. The compound of claim 16, having the formula:

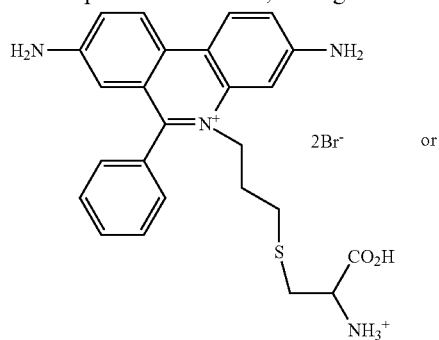

18. The compound of claim 16, wherein at least one of $R_1$, $R_2$, $R_3$, $R_4$, and $R_5$ is sulfonate (—$SO_3^-$).

19. The compound of claim 16, wherein $R_1$, $R_2$, $R_3$, $R_4$, and $R_5$ are each independently H or —$SO_3^-$.

20. The compound of claim 16, wherein $R_1$, $R_2$, $R_4$, and $R_5$ are each H and $R_3$ is —$SO_3^-$.

21. The compound of claim 16, wherein $R_7$, $R_8$, $R_9$, $R_{10}$, $R_{11}$, and $R_{12}$ are each H.

22. The compound of claim 16, wherein $A_1$ and $A_2$ are each —$NH_2$.

23. The compound of claim 16, wherein $R_{31}$, $R_{32}$, $R_{33}$, $R_{34}$, and $R_{35}$ are each independently $C_1$-$C_7$ alkyl.

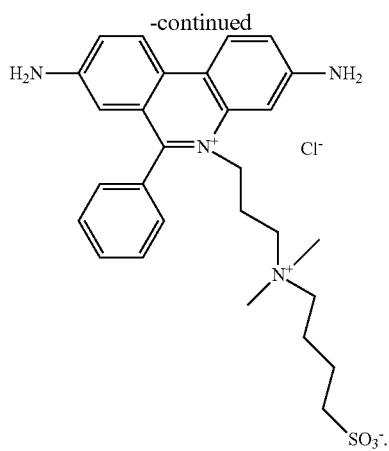

* * * * *

UNITED STATES PATENT AND TRADEMARK OFFICE
CERTIFICATE OF CORRECTION

PATENT NO. : 10,011,570 B2
APPLICATION NO. : 14/506496
DATED : July 3, 2018
INVENTOR(S) : Fei Mao et al.

Page 1 of 1

It is certified that error appears in the above-identified patent and that said Letters Patent is hereby corrected as shown below:

On the Title Page

Attorney, Agent, or Firm, item (74), delete "Wilson Sonsini Goodrich & Roasti" and insert -- Wilson Sonsini Goodrich & Rosati --.

In the Claims

Claim 1, Column 53, Line 29, delete "L-(Z)," and insert -- -L-(Z)$_m$, --.

Signed and Sealed this
Twelfth Day of February, 2019

Andrei Iancu
*Director of the United States Patent and Trademark Office*